(12) United States Patent
Jong et al.

(10) Patent No.: US 10,000,451 B2
(45) Date of Patent: Jun. 19, 2018

(54) MAP4K4 (HGK) INHIBITORS

(71) Applicant: SRI INTERNATIONAL, Menlo Park, CA (US)

(72) Inventors: Ling Jong, Menlo Park, CA (US); Chih-Tsung Chang, Menlo Park, CA (US); Jaehyeon Park, Menlo Park, CA (US)

(73) Assignee: SRI International, Menlo Park, CA (US)

(*) Notice: Subject to any disclaimer, the term of this patent is extended or adjusted under 35 U.S.C. 154(b) by 0 days. days.

(21) Appl. No.: 15/650,902

(22) Filed: Jul. 15, 2017

(65) Prior Publication Data

US 2017/0320824 A1 Nov. 9, 2017

Related U.S. Application Data

(63) Continuation of application No. PCT/US2015/036816, filed on Jun. 19, 2015.

(60) Provisional application No. 62/104,764, filed on Jan. 18, 2015.

(51) Int. Cl.
*C07D 403/02* (2006.01)
*A61K 31/404* (2006.01)
*C07D 209/14* (2006.01)
*C07D 209/12* (2006.01)
*C07D 405/02* (2006.01)

(52) U.S. Cl.
CPC .......... *C07D 209/14* (2013.01); *A61K 31/404* (2013.01); *C07D 209/12* (2013.01); *C07D 403/02* (2013.01); *C07D 405/02* (2013.01)

(58) Field of Classification Search
CPC ............................. C07D 403/02; A61K 31/404
See application file for complete search history.

(56) References Cited

U.S. PATENT DOCUMENTS

2002/0091124 A1* 7/2002 Beckers ............... A61K 31/404
514/228.2
2009/0142832 A1 6/2009 Dalton et al.

OTHER PUBLICATIONS

Mahboobi et al. (J. Med. Chem. 2001, 44, 4535-4553).*
Brancale et al. (Medicinal Research Reviews, v. 27(2), p. 209-238 (2007)).*
Lai et al. (European Journal of Medicinal Chemistry 46 (2011) 3623-3629).*
SID 217988847, AKos Consulting & Solutions, Oct. 20, 2014.
ISR-WO PCT/US15/66519.
Teller et al. Bis(1 H-2-indolyl)-1-methanones as inhibitors of the hematopoietic tyrosine kinase 1-9 Flt3. Leukemia 16: 1528-1534, 2002. entire document.
Beckers et al. 2-Aroylindoles, a Novel Class of Potent, Orally Active Small Molecule Tubulin Inhibitors, Cancer Research 62: 3113-3119, 2002. entire document.

* cited by examiner

*Primary Examiner* — Robert Havlin
(74) *Attorney, Agent, or Firm* — Ballard Spahr LLP

(57) ABSTRACT

The invention provides mitogen-activated protein kinase kinase kinase kinase 4 (MAP4K4) inhibitors, and pharmaceutically acceptable salts, hydrides and stereoisomers thereof. The compounds are employed in pharmaceutical compositions, and methods of making and use, including treating a person in need thereof with an effective amount of the compound or composition, and detecting a resultant diminution of tumor cell growth, cancer or metastasis.

20 Claims, No Drawings

MAP4K4 (HGK) INHIBITORS

This application is a continuation of PCT/US15/36816, filed: Jun. 19, 2015, which claims priority to Ser No. 62/104,764, filed Jan. 18, 2015, both incorporated by reference in their entirety for all purposes.

This invention was made with government support under Department of Defense, Army Medical Research Acquisition Activity contract no. W81XWH-09-1-0589. The government has certain rights in the invention.

INTRODUCTION

MAP4K4 (also called HGK) is also a pro-migratory protein involved in mammalian development and increases tumor cell motility likely through c-Jun N-terminal kinase (JNK). Increased MAP4K4 was significantly associated with time to biochemical failure. MAP4K4 is similarly incorporated in numerous independent gene expression signatures which are predictive of survival in colorectal cancer and recurrence in prostate cancer. Additionally, MAP4K4 is an independent prognostic factor for hepatocellular carcinoma and lung adenocarcinoma. Xenograft tumor growth in mice using a hepatocellular cell line is substantially inhibited by RNA interference of MAP4K4, indicating a potential therapeutic target for treatment of cancer. There are no drugs currently in the clinic that are known to specifically target MAP4K4 for cancer therapy. See Rizzardi et al., BMC Cancer. 2014; 14: 244.

We presented a poster at the 105th Annual American Association for Cancer Research (AACR) meeting in San Diego in April 2014 reporting that we had developed highly potent and selective MAP4K4 (HGK) inhibitors for cancer therapy. Here we disclose those inhibitors.

Related compounds were reported over ten years ago as intermediaries in the synthesis of 2,3'-diindolylmethanes and substituted indolo[3,2-b]carbazoles, Wahlstroem, Niklas; Stensland, Birgitta; Bergman, Jan, Synthesis (2004), (8), 1187-1194.

SUMMARY OF THE INVENTION

The invention provides methods and compositions for treating conditions like tumor cell growth, treat cancer, and inhibit metastasis.

1. In one aspect the invention is a compound of formula I:

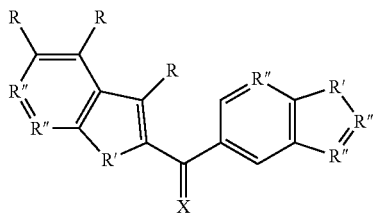

wherein:
X is O or NOH;
each R' is independently substituted or unsubstituted amine (NH, NMe) or O;
each R" is independently N or CR; and
each R is independently H, halo, OH, or C1-C9 alkyl, alkyl amine or alkyl ether, each of which is substituted or unsubstituted and comprises 0-3 heteroatoms, or a pharmaceutically acceptable salt, hydride or stereoisomer thereof.

2. In embodiments the compound is also of formula II:

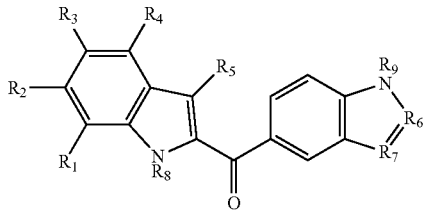

meeting 1, 2 or 3 of the criteria:
R1-R5 and R10 are independently H, halo, OH, or C1-C9 alkyl, alkyl amine or alkyl ether, each of which is substituted or unsubstituted and comprises 0-3 heteroatoms selected from N, O, S and P;
R6-R7 are independently N or CR10; and
R8-R9 are independently H or Me, or a pharmaceutically acceptable salt, hydride or stereoisomer thereof.

3. In embodiments the compound meets 1, 2, 3 or 4 of the criteria:
R1, R2, R4 and R5 are H;
R3 is OH, or C1-C6 or alkyl ether, which is substituted or unsubstituted and comprises 0-3 heteroatoms selected from N, O, S and P;
R7 is CR10; and
R8 and R9 are H, or a pharmaceutically acceptable salt, hydride or stereoisomer thereof.

Some exemplified substituents include Cl, F, Me, Et, CF3, CH2NMe2, OH, OMe, OCH2CH2NMe2, O-phenyl, C-morpholine, and N-morpholine. All possible combinations are encompassed as though each was expressly recited; hence, the aspects and embodiments include, for example, the combination wherein R1, R2, R4 and R5 are H; R3 is OMe; R7 is CR10; R8 and R9 are H, and R10 is H, halo, OH, Me or Et.

Representative examples of such compounds have been demonstrated to be mitogen-activated protein kinase kinase kinase kinase 4 (MAP4K4) inhibitors.

4. In embodiments the compound is a diindolylmethanone or indol-2-yl, indol-6-yl-methanone, or a pharmaceutically acceptable salt, hydride or stereoisomer thereof.

5. In embodiments the compound is a specifically recited compound herein, such as of Table I, or a pharmaceutically acceptable salt, hydride or stereoisomer thereof.

6. In another aspect the invention is a pharmaceutical composition suitable for administration to a human and comprising subject compound, or a pharmaceutically acceptable salt, hydride or stereoisomer thereof, in unit dosage.

7. In embodiments the composition is copackaged or coformulated with a second, different medicament for inhibiting tumor cell growth, treating cancer, or inhibiting metastasis.

8. In another aspect the invention provide a method or use of a subject compound or composition in a person in need thereof, to inhibit tumor cell growth, treat cancer, or inhibit metastasis.

9. In embodiments the use or method further comprises the antecedent step of diagnosing the tumor cell growth, cancer, or metastasis, and/or the subsequent step of detecting a resultant diminution of the tumor cell growth, cancer or metastasis.

The invention encompasses all combination of the particular embodiments recited herein.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results. The invention provides myriad embodiments.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3)alkyl is shorthand for a recitation of all C1-C3 alkyls: methyl, ethyl and propyl, including isomers thereof.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2$—$CH_2$—$CH_2$—$CH_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$.

Similarly, the term "heteroalkylene," by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR'=O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO2R', —NR'—C(O)NR"R'", —NR'—SO$_2$NR"R'", —NH—C(NH2)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alko-xy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O) R', —OC(O)NR'R", —NR"C(O)R', —S(O)R', —SO$_2$R', —SO$_2$NR'R", —NR"SO$_2$R, —N$_3$, —CH(Ph)$_2$, perfluoro (C1-C4)alkoxy and perfluoro(C1-C4)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4) alkoxy and perfluoro(C1-C4)alkyl.

The substituent —CO$_2$H, as used herein, includes bioisosteric replacements therefore; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula-T-C(O)—(CH$_2$)q-U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R in —NR'— and —S(O)$_2$NR'— is selected from hydrogen or unsubstituted (C1-C6)alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, diastereomers, geometric isomers and individual isomers are all intended to be encompassed within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the compounds may be advantageously used in conjunction with other therapeutic agents as described herein or otherwise known in the art, particularly other anti-cancer agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

We have successfully developed orally active, highly effective and selective MAP4K4 inhibitors with potent in vitro and in vivo anticancer activity. Exemplified inhibitors are more potent than Paclitaxel (Taxol) against most of the breast cancer cell lines tested and exhibit more potent activities against triple negative (MDA-MB-231, BT549 and Hs578T) than estrogen-dependent (T47D and MCF-7) breast cancer cell lines. Generally, their potency is positively correlated with MAP4K4 expression in cancer cell lines.

TABLE 1

$IC_{50}$ (µM) Paclitaxel and SRI inhibitors against breast cancer cell lines

|  |  | Paclitaxel | #18 | #17 | #15 | #23 |
|---|---|---|---|---|---|---|
| Triple | MDA-MB-231 | 0.153 | 0.014 | 0.01 | 0.021 | 0.028 |
| Negative | HS578T | 0.148 | 0.013 | 0.01 | 0.016 | 0.029 |
|  | BT549 | 0.151 | 0.012 | 0.009 | 0.017 | 0.023 |
| ER | T47D | 0.152 | 0.029 | 0.017 | 0.03 | 0.044 |
| (+) | MCF-7 | 0.156 | 0.083 | 0.053 | 0.123 | 0.114 |

The inhibitors are more potent than Docetaxel against prostate cancer cell lines. The inhibitors are more potent than Docetaxel, the current first-line treatment for metastatic castration resistant prostate cancer, against both androgen-dependent (LNCaP) and -independent (PC-3 and DU-145) prostate cancer cell lines. The dose-response curves of cell growth inhibition were consistent.

TABLE 2

IC$_{50}$ (μM) Docetaxel and SRI inhibitors
against prostate cancer cell lines

|  | Docetaxel | #18 | #17 | #15 | #23 |
|---|---|---|---|---|---|
| PC-3 | 0.095 | 0.011 | 0.006 | 0.017 | 0.020 |
| DU-145 | 0.072 | 0.023 | 0.014 | 0.035 | 0.053 |
| LNCaP | 0.031 | 0.016 | 0.009 | 0.021 | 0.028 |

In vivo pharmacokinetic (PK) studies; oral bioavailability. We conducted pre-formulation studies and selected different oral formulations for mice PK studies to explore the effect of formulation on drug absorption.

TABLE 3

Two oral formulations for PK studies in mice

| Excipient | Solubility Tested (visual) |
|---|---|
| 0.5% aqueous hydroxypropylcellulose (HPC) | Suspension |
| PEG400/Transcutol HP/Tween 80/Water (PTTW; 6:4:1:9) | Up to 10 mg/mL |

The inhibitors exhibit oral bioavailability in mice. The PK profiles of representative compounds (60 mg/kg) were determined in different oral formulations (HPC and PTTW) with groups of three mice per time point. Our data indicate that representative compounds are orally bioavailable anticancer agents and have a reasonable half-life.

TABLE 4

Effect of formulation on plasma drug levels

| Time points | Cmpd 18 (60 mg/kg) in 0.5% HPC | Cmpd 18 (60 mg/kg) in PTTW |
|---|---|---|
|  | Plasma concentration (ng/ml) | |
| 0.5 h | 319.1 ± 105.8 | 797.8 ± 203.9 |
| 4 h | 33.0 ± 21.0 | 75.5 ± 19.3 |
| 8 h | 34.7 ± 18.8 | 21.7 ± 11.1 |
| 24 h | 1.3 ± 2.3 | 15.4 ± 7.2 |

The compounds are experimentally predicted to have a longer half-life in humans. We conducted metabolic stability studies in human and mouse liver microsomes. Metabolic stability in pooled human or mouse liver microsomes, in the presence of NADPH, was measured with 10 μM compound over 60 min. Representative compounds had a lower metabolic rate in human liver microsomes than in mouse liver microsomes during the 60 min incubation.

TABLE 5

In Vitro Metabolic Stability of Using
Human and Mouse Liver Microsomes

| Test Article | Time (min) | % of Parent Compound Remaining vs T = 0 min[a] | |
|---|---|---|---|
|  |  | Human | Mouse |
| Cmpd 18 | 15 | 72.9 | 31.6 |
|  | 30 | 63.1 | 9.9 |
|  | 60 | 53.0 | 1.0 |

[a]% of test article remaining at T = 0 min is assumed to be 100%.

In vivo efficacy studies: antitumor and antimetastatic effects against androgen-insensitive prostate cancer. Antitumor activity was tested in nude mice bearing aggressive, androgen-independent PC-3 prostate cancer xenografts. Docetaxel, a standard treatment for metastatic prostate cancer, was included in the study as a positive control. Docetaxel was administered at its maximum tolerated dose (MTD) via intraperitoneal (IP) (Q3Dx2; Monday, Friday). Mice were orally treated with compound in 0.5% HPC with 4 different treatment regimens. The control group was treated with vehicle (0.5% HPC) only. Treatment was initiated when average tumor volume reached 100 mm$^3$ (10 mice per group).

The compounds show a significant dose-dependent growth inhibition of prostate tumor. Docetaxel at its MTD (7.5 mg/kg; Q3Dx2) produces only 10-15% growth inhibition. In fact, mice died on Day 13 due to lethal toxicity after receiving the 4$^{th}$ IP injection of docetaxel. Treatment with representative compounds (12.5, 25 and 50 mg/kg/day) caused a significant dose-dependent growth reduction of PC-3 tumors. Tumor regression was observed in mice treated with 60 mg/kg (twice a week; Monday, Thursday) with the greatest inhibition of ~100%. Our results show that representative compounds are more potent than Docetaxel against prostate cancer both in vitro and in vivo.

Non-GLP toxicology studies. Prior to the efficacy study in nude mice, we routinely conducted a 14-day repeat dose toxicity study using the same species of mouse. Mice were administered compounds by oral gavage in 0.5% HPC or PTTW. Compounds with favorable safety profiles were advanced to tumor xenograft studies. Our toxicology studies show that the MTDs of representative compounds are greater than 100 mg/kg in nude mice. No significant weight loss was seen after two weeks of oral administration (12.5, 25 and 50 mg/kg/day).

Efficacy-related endpoints. We conducted an in-depth mechanism of action study in androgen-sensitive (LNCaP) and -insensitive (PC-3 and DU-145) prostate cancer cell lines. Tested compounds potently inhibited cell proliferation, suppressed cell invasion, induced apoptosis and caused cell cycle arrest at M phase.

Cell proliferation assays. Cell viability dose-response curves for PC-3, DU-145 and LNCaP prostate cancer cells exposed to docetaxel and representative compounds for 72 hours demonstrate that all tested candidates are more potent than docetaxel against all three prostate cancer cell lines tested.

Apoptosis assay. The Caspase-Glo® 3/7 Assay (Promega), a homogeneous, luminescent assay that measures caspase-3 and -7 activities, was used to access apoptosis induction. Representative compounds induced dose- and time-dependent apoptosis. For example, cmpd 18 at a concentration of 20 nM significantly induced apoptosis after 24 hours treatment, and produced a more profound apoptotic effect after 48 hours treatment.

Cell cycle analysis. Representative compounds (0.1 μM) were able to block cell progression after 6 hours treatment, and significantly arrested cell cycle at the G2/M phase after 16 hours treatment. Cmpd-induced G2/M phase cell cycle arrest was demonstrated in a time-dependent manner, and observed in all three prostate cancer cell lines.

Fluorescence-activated cell sorting (FACS) analysis of M-Phase arrest. Anti-phospho-Histone 3 (pH3) antibody was used to identify cells in M phase. FACS analysis of pH3 staining cells showed that compounds induced significant M phase cell cycle arrest after 16 hours treatment in all three prostate cancer cell lines.

Boyden chamber invasion assay. Metastatic castration-resistant prostate cancer (mCRPC) remains incurable, and the demand for novel therapies continues. We evaluated compound anti-invasive effect using aggressive, androgen-nonresponsive PC-3 cells. Representative data show inhibition of PC-3 cells invasion by 83% at 0.1 µM concentration after 16 h treatment.

Signaling pathways mediating anticancer activity. Kinase screening and profiling of a panel of 456 kinases, followed by kinase inhibition assays and in vitro pharmacology studies, indicated that the compounds are potent, highly selective MAP4K4 inhibitors. We established the MAP4K4 kinase assay in-house and confirmed that the compounds are indeed potent MAP4K4 inhibitors. The SRI compounds inhibited MAP4K4 activity in a dose-response manner.

TABLE 6

MAP4K4 activity

| Cmpd # | IC50 (M) |
|---|---|
| 1 | 1.60E−07 |
| 4 | 3.80E−07 |
| 5 | 3.00E−07 |
| 9 | 1.70E−06 |
| 12 | 1.00E−06 |
| 17 | 2.60E−07 |
| 18 | 1.40E−07 |
| 19 | 9.00E−09 |
| 20 | 3.10E−07 |
| 21 | 1.00E−07 |
| 22 | 2.10E−05 |
| 23 | 4.10E−07 |
| 24 | 1.20E−05 |
| 28 | 6.50E−07 |
| 29 | 6.50E−07 |
| 31 | 1.30E−08 |
| 33 | 4.60E−08 |
| 35 | 7.50E−06 |
| 36 | 5.70E−07 |

MAP4K4 belongs to the mammalian STE20/MAP4K family, is frequently overexpressed in many types of human cancers, and appears to play important roles in transformation, invasiveness, adhesion, and cell migration. Comparison of MAP4K4 expression in prostatic intraepithelial neoplasia (PIN) and metastatic prostate cancer samples suggested that MAP4K4 levels correlate with the progression and metastasis of the tumors. SRI's first-in-class MAP4K4 inhibitors, which display potent in vitro and in vivo antitumor activity, have great potential to treat metastatic castration-resistant prostate cancer.

These compounds demonstrated in vitro anticancer activity and are more potent than docetaxel against androgen-sensitive and -insensitive prostate cancer cell lines. Our compounds at 60 mg/kg dose level (administered twice weekly) completely inhibit prostate tumor growth and are more potent than Docetaxel (administered at its maximum tolerated dose) in PC-3 tumor xenografts. Tumor regression was observed in >50% of compound-treated mice. Pharmacokinetic studies demonstrate good oral bioavailability. Toxicology results from a 14-day repeat dose study in mice were favorable.

Our compounds are MAP4K4 (HGK) inhibitors, and hence are generally useful in treating pathogenic conditions associated with MAP4K4 overexpression. In particular many cancers are associated with MAP4K4 overexpression, and we have consistently demonstrated efficacy with representative compounds against panels of diverse cancer cells with MAP4K4 overexpression. Exemplary data is shown below.

TABLE 7

Acticities against various cancer cell lines.

| Cell Line | IC50 | | |
|---|---|---|---|
| | Doxorubicin | #1 | #37 |
| A498 | 6.5E−07 | 5.2E−08 | 3.30E−07 |
| ACHN | 5.4E−07 | 5.7E−09 | 7.60E−07 |
| CCRFCEM | 8.7E−08 | 6.2E−08 | 1.80E−07 |
| LOXIMVI | 2.6E−07 | 1.4E−08 | 4.40E−07 |
| M14 | 8.1E−07 | 3.8E−08 | 1.10E−07 |
| MDAMB435 | 9.7E−07 | 2.1E−08 | 6.60E−08 |
| MOLT4 | 7.5E−08 | 5.3E−08 | 1.20E−07 |
| OVCAR8 | 8.8E−07 | 6.7E−08 | 5.60E−07 |
| SF295 | 4.3E−07 | 5.4E−08 | 2.50E−07 |
| SF539 | 3.9E−07 | 3.9E−08 | 1.70E−07 |
| SKMEL2 | 6.8E−07 | 6.3E−08 | 5.80E−07 |
| SKMEL5 | 3.9E−07 | 3.3E−08 | 2.10E−07 |
| UO31 | 2.50E−06 | 6.6E−08 | 6.90E−07 |
| HCT15 | 1.30E−06 | 2.70E−08 | 6.80E−08 |
| HL60 | 1.50E−07 | 3.50E−08 | 8.10E−08 |
| MCF7 | 4.10E−07 | 5.90E−08 | 8.50E−08 |
| OVCAR4 | 1.90E−06 | 9.00E−08 | 1.50E−07 |
| RXF393 | 1.00E−06 | 3.80E−08 | 1.40E−07 |
| SNB75 | 6.10E−07 | 4.20E−08 | 1.10E−07 |
| ADRRES | 1.10E−05 | 2.70E−08 | 6.40E−08 |
| CAKI1 | 1.80E−07 | 2.30E−08 | 6.70E−08 |
| CCRFCEM | 4.70E−08 | 2.90E−08 | 8.70E−08 |
| HL60 | 1.30E−07 | 2.40E−08 | 7.80E−08 |
| NCIH522 | 5.00E−07 | 3.20E−08 | 1.00E−07 |
| OVCAR4 | 1.50E−06 | 5.60E−08 | 1.10E−07 |
| OVCAR8 | 3.30E−07 | 5.30E−08 | 1.60E−07 |
| SNB75 | 5.80E−07 | 3.40E−08 | 1.10E−07 |

TABLE I

Compound List

| # | Structure | # | Structure |
|---|---|---|---|
| 1 | [MeO-substituted indole connected via carbonyl to indole] | 21 | [MeO-substituted indole connected via carbonyl to fluoro-indazole] |

TABLE I-continued
Compound List
| # | Structure | # | Structure |
|---|---|---|---|
| 2 | 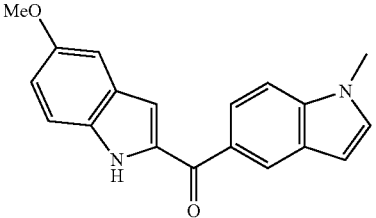 [SMILES: COc1ccc2[nH]c(C(=O)c3ccc4c(ccn4C)c3)cc2c1] | 22 | 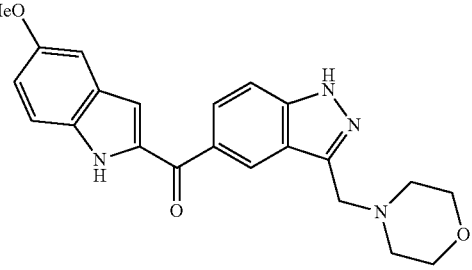 |
| 3 | 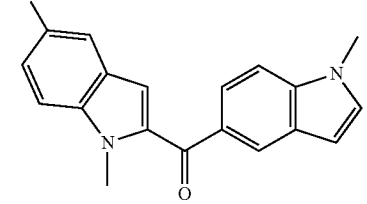 | 23 | 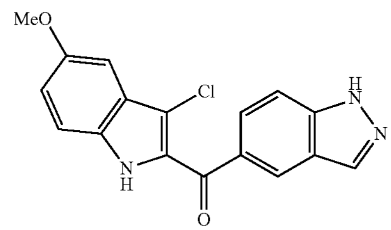 [SMILES: COc1ccc2[nH]c(C(=O)c3ccc4[nH]ncc4c3)c(Cl)c2c1] |
| 4 | 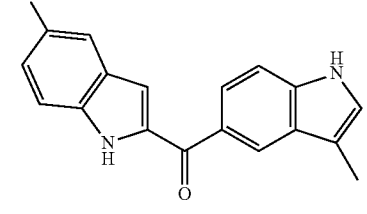 | 24 | 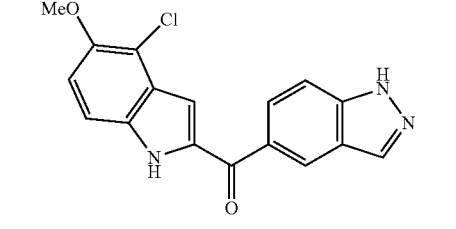 [SMILES: COc1ccc2[nH]c(C(=O)c3ccc4[nH]ncc4c3)cc2c1Cl] |
| 5 | 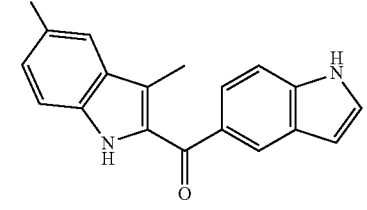 | 25 | 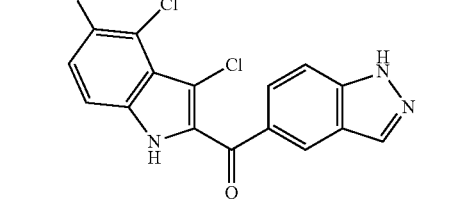 |
| 6 | 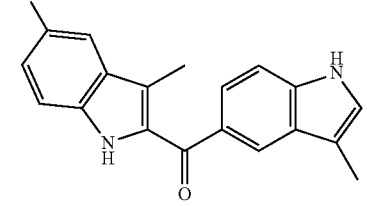 | 26 | 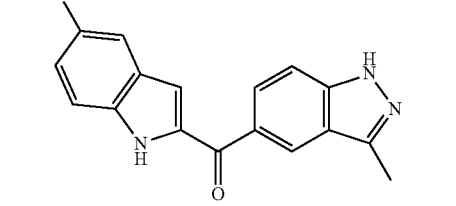 |
| 7 | 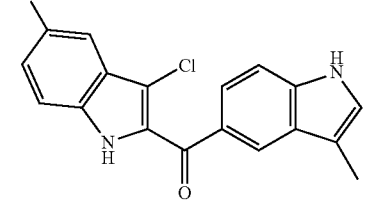 | 27 | 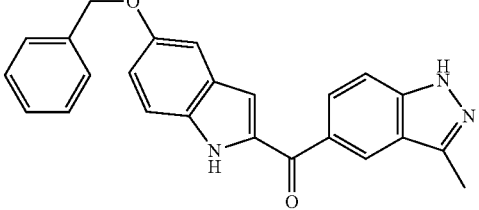 |

TABLE I-continued

Compound List

| # | Structure | # | Structure |
|---|---|---|---|
| 8 | 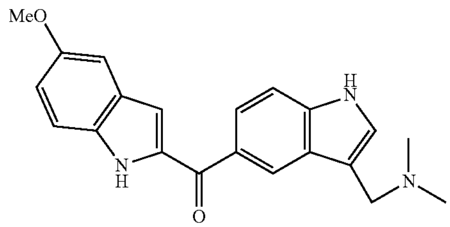 [SMILES: COc1ccc2[nH]c(C(=O)c3ccc4[nH]cc(CN(C)C)c4c3)cc2c1] | 28 | 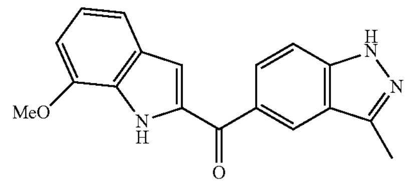 [SMILES: COc1cccc2cc(C(=O)c3ccc4[nH]nc(C)c4c3)[nH]c12] |
| 9 | 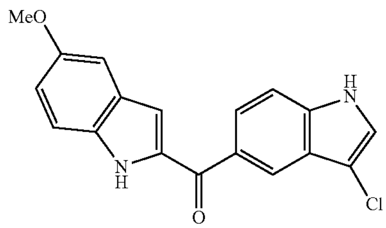 [SMILES: COc1ccc2[nH]c(C(=O)c3ccc4[nH]cc(Cl)c4c3)cc2c1] | 29 | 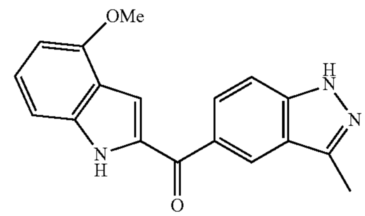 [SMILES: COc1cccc2[nH]c(C(=O)c3ccc4[nH]nc(C)c4c3)cc12] |
| 10a | 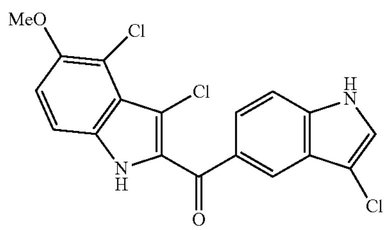 [SMILES: COc1ccc2[nH]c(C(=O)c3ccc4[nH]cc(Cl)c4c3)c(Cl)c2c1Cl] | 30 | 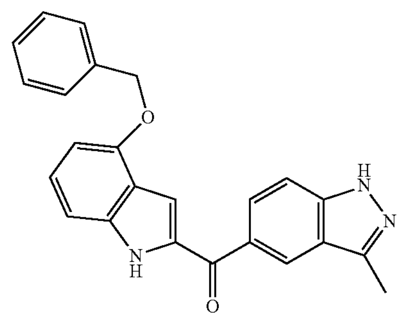 [SMILES: Cc1n[nH]c2ccc(C(=O)c3cc4c(OCc5ccccc5)cccc4[nH]3)cc12] |
| 10b | 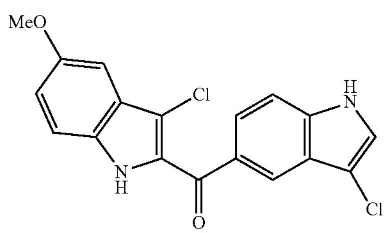 [SMILES: COc1ccc2[nH]c(C(=O)c3ccc4[nH]cc(Cl)c4c3)c(Cl)c2c1] | 31 | 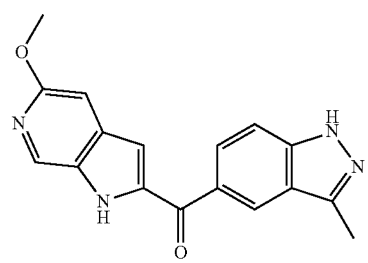 [SMILES: COc1cc2cc(C(=O)c3ccc4[nH]nc(C)c4c3)[nH]c2cn1] |
| 11 | 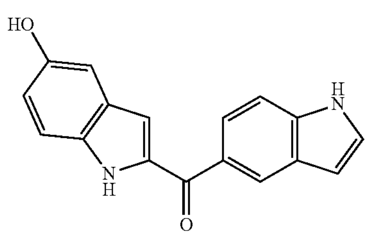 [SMILES: O=C(c1ccc2[nH]ccc2c1)c1cc2cc(O)ccc2[nH]1] | 32 | 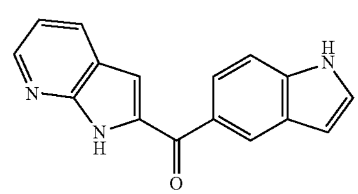 [SMILES: O=C(c1ccc2[nH]ccc2c1)c1cc2cccnc2[nH]1] |
| 12 | 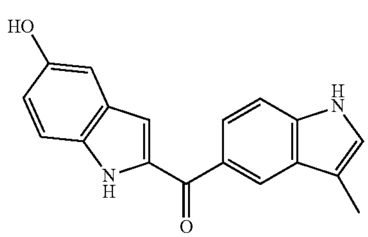 [SMILES: Cc1c[nH]c2ccc(C(=O)c3cc4cc(O)ccc4[nH]3)cc12] | 33 | 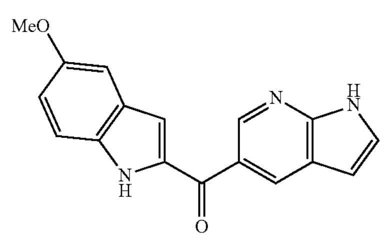 [SMILES: COc1ccc2[nH]c(C(=O)c3cnc4[nH]ccc4c3)cc2c1] |

TABLE I-continued

Compound List

| # | Structure | # | Structure |
|---|---|---|---|
| 13 | (structure) | 34 | (structure) |
| 14 | (structure) | 35 | (structure) |
| 15 | (structure) | 36 | (structure) |
| 16 | (structure) | 37 | (structure) |
| 17 | (structure) | 38 | (structure) |
| 18 | (structure) | 39 | (structure) |

TABLE I-continued

Compound List

| # | Structure | # | Structure |
|---|---|---|---|
| 19 | 5-methoxy-indol-2-yl 3-ethyl-1H-indazol-5-yl methanone | 40 | 5-methoxy-indol-2-yl benzofuran-5-yl methanone |
| 20 | 5-methoxy-indol-2-yl 3-chloro-1H-indazol-5-yl methanone | 41 | 5-methoxy-indol-2-yl 1H-indol-6-yl methanone |

Compound Preparation

Example 1

(1H-indol-5-yl)(5-methoxy-1H-indol-2-yl)methanone

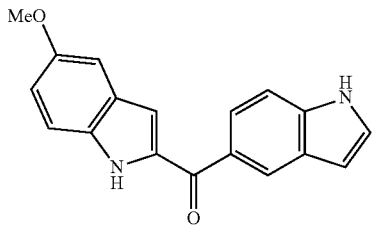

1. To solution of 5-methoxy-1H-indole (15 g, 67.9 mmol) in 300 mL of THF, was added sodium hydride (60 wt % dispersion, 5.1 g, 84.9 mmol) at 0° C. After 1 hr RT, phenylsulfonylchloride (16.35 mL, 84.93 mmol) was added. After overnight, the reaction was quenched with saturated ammonium chloride solution at 0° C., and extracted with EtOAc (×3). The combined organic extracts were dried (MgSO$_4$), filtered, and concentrated. The residue was trituration from MeOH to give 5-methoxy-1-(phenylsulfonyl)-1H-indole (28.7 g, 98%) as a white solid. $^1$H NMR (400 MHz, CDCl$_3$) δ ppm: 7.87 (d, J=9.2, Hz, 1H), 7.83 (d, J=7.2 Hz, 2H), 7.53-7.47 (m, 2H), 7.40 (t, J=8 Hz, 2H), 6.95 (d, J=2.4 Hz, 1H), 6.91 (dd, J=9.2, 2.4 Hz, 1H), 6.57 (d, J=3.6 Hz, 1H).

2. To a solution of 5-bromo-1H-indole (3.5 g, 17.85 mmol) in 100 mL of ethyl ether, was added 52.5 mL of t-BuLi solution in pentane (1.7 M) at −78° C. After 1 hr at −78° C., the reaction mixture was added DMF (25 mL). After 2 hr at 0° C., the reaction was quenched with saturated ammonium chloride, and extracted with EtOAc (×3). The combined organic extracts were washed with water, brine, dried (MgSO$_4$), filtered, and concentrated to give crude 1H-indole-5-carbaldehyde (quant.).

The mixture of 1H-indole-5-carbaldehyde (1.77 g, 12.25 mmol), phenylsulfonylchloride (1.89 mL, 14.7 mmol), diisopropylethylamine (10.7 mL, 61.3 mmol), and DMAP (149 mg, 1.22 mmol) in 60 mL of dichloromethane was stirred at RT for 18 hr, diluted with dichloromethane, washed with water, was dried (MgSO$_4$), and concentrated. The residue was purified by chromatography (50% EtOAc/Hexanes) to give 1-(phenylsulfonyl)-1H-indole-5-carbaldehyde (3.33 g, 95%). $^1$H NMR (400 MHz, CDCl$_3$) δ ppm: 9.89 (s, 1H), 8.06 (d, J=8.4 Hz, 1H), 8.05 (d, J=1.6 Hz, 1H), 7.84 (dd, J=8.4, 1.2 Hz 2H), 7.80 (dd, J=8.4, 1.6 Hz, 1H), 7.62 (d, J=3.6 Hz, 1H), 7.51 (t, J=7.6 Hz, 1H), 7.41 (t, J=8.0 Hz, 2H), 6.73 (d, J=4.0 Hz, 1H).

3. To a solution of 5-methoxy-1-(phenylsulfonyl)-1H-indole (1.5 g, 5.22 mmol) in 30 mL of THF, was added 2.19 mL of n-BuLi solution in hexanes (2.5 M) at −78° C. After 1 hr, a solution of 1-(phenylsulfonyl)-1H-indole-5-carbaldehyde (1.5 g, 5.22 mmol) in 15 mL of THF was added slowly. The reaction mixture was allowed to warm up to RT slowly. After 1.5 hr, the reaction was quenched with saturated ammonium chloride solution, and extracted with EtOAc (×3). The combined organic extracts were dried (MgSO$_4$), filtered, and concentrated. Flash chromatography (50% EtOAc/Hexanes) gave (5-methoxy-1-(phenylsulfonyl)-1H-indol-2-yl)(1-(phenylsulfonyl)-1H-indol-5-yl)methanol (2.2 g, 74%). $^1$H NMR (400 MHz, CDCl$_3$) δ ppm: 7.99 (d, J=8.8 Hz 1H), 7.95 (d, J=8.8 Hz, 1H), 7.90 (d, J=7.2 Hz, 2H), 7.62 (d, J=7.2 Hz, 2H), 7.59-7.53 (m, 3H), 7.45 (t, J=8.4 Hz, 3H), 7.31 (dd, J=8.8, 2.0 Hz, 1H), 7.27 (t, J=8.8 Hz, 2H), 6.91 (dd, J=9.2, 2.4 Hz, 1H), 6.81 (d, J=2.8 Hz, 1H), 6.61 (d, J=3.6 Hz, 1H), 6.40 (d, J=4.8 Hz, 1H), 6.15 (s, 1H), 3.77 (s, 3H), 3.52 (d, J=4.4 Hz, 1H).

4. The mixture of (5-methoxy-1-(phenylsulfonyl)-1H-indol-2-yl)(1-(phenylsulfonyl)-1H-indol-5-yl)methanol (2.2 g, 3.84 mmol), and MnO$_2$ (6.7 g, 76.87 mmol) in 60 mL of dichloromethane was stirred overnight at RT, diluted with dichloromethane, filtered through a pad of Celite, and concentrated to give (5-methoxy-1-(phenylsulfonyl)-1H-indol-2-yl)(1-(phenylsulfonyl)-1H-indol-5-yl)methanone (1.96 g, 89.5%). $^1$H NMR (400 MHz, CDCl$_3$) δ ppm: 8.14 (s, 1H), 8.09 (d, J=8.8 Hz, 1H), 8.04-7.97 (m, 4H), 7.92 (d, J=7.2 Hz, 2H), 7.65 (d, J=3.6 Hz, 1H), 7.62-7.53 (m, 2H), 7.52-7.43

(m, 4H), 7.07 (dd, J=9.2, 2.4 Hz, 1H), 6.97 (d, J=2.4 Hz, 1H), 6.84 (s, 1H), 6.74 (d, J=3.6 Hz, 1H), 3.82 (s, 3H).

5. To a solution of (5-methoxy-1-(phenylsulfonyl)-1H-indol-2-yl)(1-(phenylsulfonyl)-1H-indol-5-yl)methanone (435 mg, 0.76 mmol) in 9 mL of THF, was added tetra-butylammonium fluoride trihydrate. (2.05 g, 7.84 mmol). The reaction mixture was heated to reflux overnight. After cooled to RT, the reaction mixture was poured into water, and extracted with EtOAc (×3). The combined organic extracts were washed with water (×2), dried (MgSO$_4$), filtered, and concentrated. Flash chromatography (60% EtOAc/Hexanes) gave (1H-indol-5-yl)(5-methoxy-1H-indol-2-yl)methanone (161 mg, 73%). $^1$H NMR (400 MHz, DMSO-d$_6$) δ ppm: 11.70 (s, 1H), 11.46 (s, 1H), 8.24 (s, 1H), 7.70 (dd, J=8.8, 2.0 Hz, 1H), 7.52 (d, J=8.4 Hz, 1H), 7.47 (t, J=2.4 Hz, 1H), 7.37 (d, J=8.8 Hz, 1H), 7.14 (d, J=2.4 Hz, 1H), 7.01 (d, J=2.0 Hz, 1H), 6.92 (dd, J=8.8, 1.6 Hz, 1H), 6.61 (s, 1H), 3.74 (s, 3H). MS: 291.15 (M+H+)

Example 2

(5-methoxy-1H-indol-2-yl)(1-methyl-1H-indol-5-yl)methanone

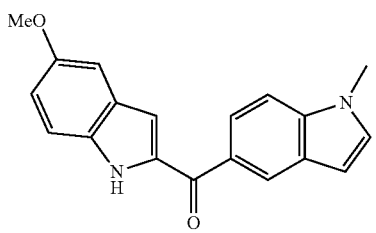 [SMILES: COc1ccc2[nH]c(C(=O)c3ccc4c(ccn4C)c3)cc2c1]

To a solution of (5-methoxy-1-(phenylsulfonyl)-1H-indol-2-yl)(1-methyl-1H-indol-5-yl)methanone (996.6 mg, 2.24 mmol) in 35 mL of THF, was added Tetra-butylammonium fluoride trihydrate (5.86 g, 22.4 mmol). The reaction mixture was refluxed for overnight. After cooled to RT, the reaction mixture was poured into water, and extracted with EtOAc (×3). The combined organic extracts were washed with water (×2), dried (MgSO$_4$), filtered, and concentrated. Flash chromatography (50% EtOAc/Hexanes) gave (5-methoxy-1H-indol-2-yl)(1-methyl-1H-indol-5-yl)methanone (195 mg, 29%). $^1$H NMR (400 MHz, CDCl$_3$) δ ppm: 9.18 (s, 1H), 8.39 (s, 1H), 7.93 (dd, J=8.4, 1.6 Hz, 1H), 7.44 (d, J=8.4 Hz, 1H), 7.39 (d, J=8.8 Hz, 1H), 7.16 (d, J=3.2 Hz, 1H), 7.14 (d, J=2.4 Hz, 1H), 7.12 (d, J=2.4 Hz, 1H), 7.05 (dd, J=9.2, 2.4 Hz, 1H), 6.65 (d, J=3.2 Hz, 1H), 3.87 (s, 3H), 3.86 (s, 3H).

Example 3

(5-methoxy-1-methyl-1H-indol-2-yl)(1-methyl-1H-indol-5-yl)methanone

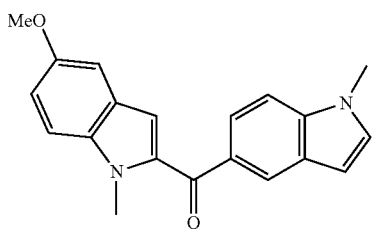 [SMILES: COc1ccc2c(c1)cc(C(=O)c1ccc3c(ccn3C)c1)n2C]

To solution of (5-methoxy-1-(phenylsulfonyl)-1H-indol-2-yl)(1-methyl-1H-indol-5-yl)methanone (60 mg, 0.197 mmol) in 2 mL of DMF, was added sodium hydride (60 wt % dispersion, 11 mg, 0.256 mmol) at 0° C. After 30 min, iodomethane (19 µL, 0.297 mmol) was added. The reaction mixture was stirred at 0° C. for 30 min, then at RT for 10 min. The reaction was quenched with water at 0° C., filtered, and concentrated. Flash chromatography (10% EtOAc/Hexanes) gave 5-methoxy-1-methyl-1H-indol-2-yl)(1-methyl-1H-indol-5-yl)methanone (50.5 mg, 80.4%). $^1$H NMR (400 MHz, CDCl$_3$) δ ppm: 8.30 (s, 1H), 7.91 (dd, J=8.4, 1.2 Hz, 1H), 7.42 (d, J=8.4 Hz, 1H), 7.36 (d, J=9.6 Hz, 1H), 7.15 (d, J=3.2 Hz, 1H), 7.08 (s, 1H), 7.06 (dd, J=7.6, 2.4 Hz, 1H), 6.93 (s, 1H), 6.62 (d, J=3.2 Hz, 1H), 4.08 (s, 1H), 3.86 (s, 3H), 3.85 (s, 3H).

Example 4

(5-methoxy-1H-indol-2-yl)(3-methyl-1H-indol-5-yl)methanone

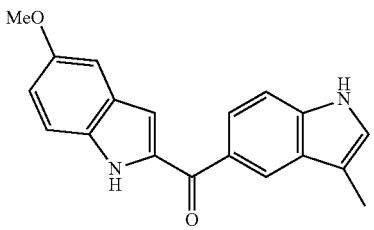 [SMILES: COc1ccc2[nH]c(C(=O)c3ccc4[nH]cc(C)c4c3)cc2c1]

1. To a solution of 5-methoxy-1-(phenylsulfonyl)-1H-indole (384 mg, 1.34 mmol) in 8 mL of THF, was added 0.562 mL of n-BuLi solution in hexanes (2.5 M) at −78° C. After 1 hr, a solution of 3-methyl-1-(phenylsulfonyl)-1H-indole-5-carbaldehyde (400 mg, 1.34 mmol) in 5 mL of THF was added slowly. The reaction mixture was allowed to warm up to RT slowly. After 1.5 hr, the reaction was quenched with saturated ammonium chloride solution, and extracted with EtOAc (×3). The combined organic extracts were dried (MgSO$_4$), filtered, and concentrated. Flash chromatography (50% EtOAc/Hexanes) gave (5-methoxy-1-(phenylsulfonyl)-1H-indol-2-yl)(3-methyl-1-(phenylsulfonyl)-1H-indol-5-yl)methanol (648 mg, 83%). $^1$H NMR (400 MHz, CDCl$_3$) δ ppm: 8.00 (d, J=8.8 Hz, 1H), 7.94 (d, J=8.4 Hz, 1H), 7.88 (d, J=7.2 Hz, 2H), 7.64 (dd, J=8.4, 1.2 Hz, 2H), 7.57-7.41 (m, 5H), 7.33 (s, 1H), 7.31 (m, 3H), 6.91 (dd, J=9.2, 2.4 Hz, 1H), 6.81 (d, J=2.8 Hz 1H), 6.41 (d, J=4.4 Hz, 1H), 6.11 (s, 1H), 3.77 (s, 3H), 3.54 (d, J=4.8 Hz, 1H), 2.19 (s, 3H).

2. The mixture of (5-methoxy-1-(phenylsulfonyl)-1H-indol-2-yl)(3-methyl-1-(phenylsulfonyl)-1H-indol-5-yl)methanol (648 mg, 1.1 mmol), and MnO$_2$ (1.9 g, 21.9 mmol) in 20 mL of dichloromethane was stirred overnight at RT, diluted with dichloromethane, filtered through a pad of Celite, and concentrated to give (5-methoxy-1-(phenylsulfonyl)-1H-indol-2-yl)(3-methyl-1-(phenylsulfonyl)-1H-indol-5-yl)methanone (597.5 mg, 92%). $^1$H NMR (400 MHz, CDCl$_3$) δ ppm: 8.11 (d, J=1.6 Hz, 1H), 8.08-8.00 (m, 4H), 7.95 (dd, J=8.8, 1.6 Hz, 1H), 7.89 (d, J=7.2 Hz, 2H), 7.57 (t, J=7.2 Hz, 2H), 7.47 (t, J=7.2 Hz, 4H), 7.40 (d, J=1.2 Hz, 1H), 7.08 (dd, J=8.8, 2.4 Hz 1H), 6.98 (d, J=2.8 Hz, 1H), 6.84 (s, 1H), 3.83 (s, 3H), 2.26 (s, 3H).

3. To a solution of (5-methoxy-1-(phenylsulfonyl)-1H-indol-2-yl)(3-methyl-1-(phenylsulfonyl)-1H-indol-5-yl)

methanone (597 mg, 1.02 mmol) in 10 mL of THF, was added Tetra-butylammonium fluoride trihydrate (2.68 g, 10.25 mmol). The reaction mixture was heated to reflux for 6 hr. After cooled to RT, the reaction mixture was poured into water, and extracted with EtOAc (×3). The combined organic extracts were washed with water, dried ($MgSO_4$), filtered, and concentrated. Flash chromatography (55% EtOAc/Hexanes) gave (1H-indol-5-yl)(5-methoxy-1H-indol-3-yl)methanone (247 mg, 79%). $^1$H NMR (400 MHz, DMSO-$d_6$) δ ppm: 11.73 (s, 1H), 11.16 (s, 1H), 8.16 (s, 1H), 7.72 (dd, J=8.8, 2.0 Hz, 1H), 7.48 (d, J=8.8 Hz, 1H), 7.39 (d, J=8.8 Hz, 1H), 7.25 (s, 1H), 7.16 (d, J=2.4 Hz, 1H), 7.04 (s, 1H), 6.94 (dd, J=9.2, 2.4 Hz, 1H), 3.76 (s, 3H), 2.31 (s, 3H).

Example 5

(1H-indol-5-yl)(5-methoxy-3-methyl-1H-indol-2-yl)methanone

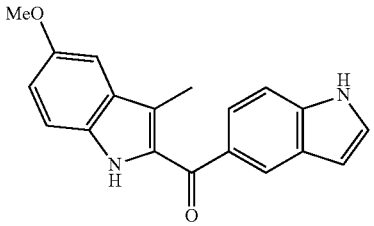 [SMILES: COc1ccc2[nH]c(C(=O)c3ccc4[nH]ccc4c3)c(C)c2c1]

1. To a cooled solution of 5-methoxy-3-methyl-1-(phenylsulfonyl)-1H-indole (2.20 g, 7.30 mmol) in 19 mL of THF, was added sodium hydride (60 wt % dispersion, 298 mg, 7.45 mmol) at 0° C. After 18 hr, phenylsulfonylchloride (0.96 mL, 7.45 mmol) was added. After 1 hr, the reaction was quenched with saturated sodium bicarbonate solution, and extracted with ethyl ether. The organic layer was dried ($MgSO_4$), and concentrated. Chromatography over 100 g $SiO_2$ (60% EtOAc/Hexanes) gave 5-methoxy-3-methyl-1-(phenylsulfonyl)-1H-indole (1.37 g, 2.34 mmol, 32%) as a colorless oil. $^1$H NMR (399 MHz, CHLOROFORM-d) δ ppm 7.86 (1H, d, J=9.0 Hz), 7.73-7.83 (2H, m), 7.44-7.52 (1H, m), 7.33-7.40 (2H, m), 7.23-7.25 (1H, m), 6.90 (1H, dd, J=9.0, 2.3 Hz), 6.85 (1H, d, J=2.3 Hz), 3.81 (3H, s), 2.19 (3H, d, J=1.2 Hz)

2. To a solution of 5-methoxy-3-methyl-1-(phenylsulfonyl)-1H-indole (301 mg, 1.00 mmol) in 5 mL of THF, was added 0.48 mL of n-BuLi solution in hexanes (2.5 M) at −78° C. After 1 hr, a solution of 1-(phenylsulfonyl)-1H-indole-5-carbaldehyde (314 mg, 1.10 mmol) in 3 mL of THF was added slowly. After 2 hr, the reaction mixture was allowed to warm up to RT slowly, quenched with saturated ammonium chloride solution, and extracted with EtOAc. The organic layer was dried ($MgSO_4$), and concentrated. Chromatography over 50 g $SiO_2$ (60% EtOAc/Hexanes) gave (5-methoxy-3-methyl-1-(phenylsulfonyl)-1H-indol-2-yl)(1-(phenylsulfonyl)-1H-indol-5-yl)methanol (315 mg, 0.537 mmol, 54%) as a brownish oil. $^1$H NMR (399 MHz, CHLOROFORM-d) δ ppm 7.95-8.06 (1H, m), 7.74-7.95 (3H, m), 7.48-7.61 (3H, m), 7.34-7.48 (2H, m), 7.28-7.34 (1H, m), 7.23-7.28 (1H, m), 7.19 (3H, d, J=7.0 Hz), 6.77-6.99 (4H, m), 6.38-6.56 (2H, m), 3.78-3.87 (3H, s), 2.11-2.20 (3H, m)

3. The mixture of (5-methoxy-3-methyl-1-(phenylsulfonyl)-1H-indol-2-yl)(1-(phenylsulfonyl)-1H-indol-5-yl)methanol and $MnO_2$ (933 mg, 10.7 mmol) in 6 mL of dichloromethane was stirred overnight at RT, diluted with dichloromethane, filtered through a pad of Celite, and concentrated. Chromatography over 25 g $SiO_2$ (80% EtOAc/Hexanes) gave (5-methoxy-3-methyl-1-(phenylsulfonyl)-1H-indol-2-yl)(1-(phenylsulfonyl)-1H-indol-5-yl)methanone (187 mg, 0.320 mmol, 60%) as an off white solid. $^1$H NMR (399 MHz, CHLOROFORM-d) δ ppm 8.01-8.10 (2H, m), 7.83-8.00 (3H, m), 7.70-7.79 (2H, m), 7.52-7.65 (2H, m), 7.41-7.52 (4H, m), 7.28-7.38 (2H, m), 7.02 (1H, dd, J=9.2, 2.5 Hz), 6.86 (1H, d, J=2.3 Hz), 6.70 (1H, d, J=3.5 Hz), 3.82 (3H, s), 2.10 (3H, s)

4. To a solution of (5-methoxy-3-methyl-1-(phenylsulfonyl)-1H-indol-2-yl)(1-(phenylsulfonyl)-1H-indol-5-yl)methanone (187 mg, 0.320 mmol) in 6 mL of THF, was added 1.6 mL of TBAF solution in THF (1 M). The reaction mixture was heated to reflux overnight, cooled to RT, diluted with EtOAc, washed with brine (×2), dried ($MgSO_4$), and concentrated. Chromatography over 10 g $SiO_2$ (80% EtOAc/Hexanes) gave (1H-indol-5-yl)(5-methoxy-3-methyl-1H-indol-2-yl)methanone (84 mg, 0.28 mmol, 86%) as an off white solid. $^1$H NMR (399 MHz, DMSO-$d_6$) δ ppm 11.46 (1H, br. s.), 11.21 (1H, s), 8.00 (1H, s), 7.43-7.60 (3H, m), 7.29 (1H, d, J=9.0 Hz), 7.05 (1H, d, J=2.3 Hz), 6.89 (1H, dd, J=8.8, 2.5 Hz), 6.58 (1H, t, J=2.2 Hz), 3.77 (3H, s), 2.23 (3H, s); MS (ESI) m/z Calculated 304.12 Found 305.11 (M+H)+.

Example 6

(5-methoxy-3-methyl-1H-indol-2-yl)(3-methyl-1H-indol-5-yl)methanone

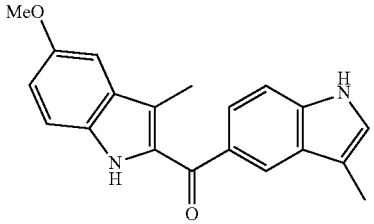 [SMILES: COc1ccc2[nH]c(C(=O)c3ccc4[nH]cc(C)c4c3)c(C)c2c1]

1. To a solution of 5-bromo-3-methyl-1H-indole (2.10 g, 10.0 mmol) in 50 mL of ethyl ether, was added 29 mL of t-BuLi solution in pentane (1.7 M) at −78° C. After 1 hr, the reaction mixture was DMF (7.7 mL) was added. After 2 hr at 0° C., the reaction was quenched with saturated ammonium chloride, and extracted with EtOAc. The organic layer was dried ($MgSO_4$), and concentrated to crude 3-methyl-1H-indole-5-carbaldehyde (quant.) as a yellow oil, which was used for the next step without further purification. To a solution of 3-methyl-1H-indole-5-carbaldehyde in 40 mL of dichloromethane, were added phenylsulfonylchloride (1.9 mL, 15.0 mmol), diisopropylethylamine (8.7 mL, 50.0 mmol), and DMAP (122 mg, 1.00 mmol). The reaction mixture was stirred at RT for 18 hr, diluted with dichloromethane, washed with saturated ammonium chloride, dried ($MgSO_4$), and concentrated. The residue was purified over 100 g $SiO_2$ (45% EtOAc/Hexanes) to give 3-methyl-1-(phenylsulfonyl)-1H-indole-5-carbaldehyde (1.60 g, 5.59 mmol, 56%) as an off white solid. $^1$H NMR (399 MHz, CHLOROFORM-d) δ ppm 10.04 (1H, s), 8.10 (1H, d, J=8.2 Hz), 8.00 (1H, d, J=1.6 Hz), 7.78-7.91 (3H, m), 7.49-7.59 (1H, m), 7.37-7.48 (3H, m), 2.29 (3H, d, J=1.2 Hz)

2. To a solution of 5-methoxy-3-methyl-1-(phenylsulfonyl)-1H-indole (190 mg, 0.632 mmol) in 3 mL of THF, was added 0.3 mL of n-BuLi solution in hexanes (2.5 M) at −78° C. After 1 hr, a solution of 3-methyl-1-(phenylsulfonyl)-1H-indole-5-carbaldehyde (199 mg, 0.695 mmol) in 2 mL of THF was added slowly. After 2 hr, the reaction mixture was allowed to warm up to RT slowly, quenched with saturated ammonium chloride solution, and extracted with EtOAc. The organic layer was dried (MgSO$_4$), and concentrated. Chromatography over 10 g SiO$_2$ (60% EtOAc/Hexanes) gave (5-methoxy-3-methyl-1-(phenylsulfonyl)-1H-indol-2-yl)(3-methyl-1-(phenylsulfonyl)-1H-indol-5-yl)methanol (45 mg, 0.075 mmol, 12%) as a brownish oil. $^1$H NMR (399 MHz, CHLOROFORM-d) δ ppm 8.04 (1H, d, J=9.0 Hz), 7.82-7.89 (2H, m), 7.79 (1H, d, J=8.6 Hz), 7.46-7.54 (1H, m), 7.35-7.46 (2H, m), 7.25-7.30 (2H, m), 7.10-7.23 (3H, m), 6.85-6.98 (4H, m), 6.48 (1H, d, J=9.8 Hz), 3.85 (3H, s), 2.11-2.16 (3H, s), 2.08 (3H, s)

3. The mixture of (5-methoxy-3-methyl-1-(phenylsulfonyl)-1H-indol-2-yl)(3-methyl-1-(phenylsulfonyl)-1H-indol-5-yl)methanol and MnO$_2$ (130 mg, 1.50 mmol) in 5 mL of dichloromethane was stirred overnight at RT, diluted with dichloromethane, filtered through a pad of Celite, and concentrated to give (5-methoxy-3-methyl-1-(phenylsulfonyl)-1H-indol-2-yl)(3-methyl-1-(phenylsulfonyl)-1H-indol-5-yl)methanone (44 mg, 0.075 mmol, 100%) as an off white solid. $^1$H NMR (399 MHz, CHLOROFORM-d) δ ppm 8.07 (1H, d, J=1.6 Hz), 8.01 (1H, d, J=8.6 Hz), 7.97 (1H, d, J=9.0 Hz), 7.82-7.90 (3H, m), 7.74-7.80 (2H, m), 7.51-7.58 (1H, m), 7.41-7.50 (3H, m), 7.30-7.40 (3H, m), 7.02 (1H, dd, J=9.0, 2.7 Hz), 6.87 (1H, d, J=2.3 Hz), 3.83 (3H, s), 2.24 (3H, d, J=1.6 Hz), 2.10 (3H, s)

4. To a solution of (5-methoxy-3-methyl-1-(phenylsulfonyl)-1H-indol-2-yl)(3-methyl-1-(phenylsulfonyl)-1H-indol-5-yl)methanone (44 mg, 0.075 mmol) in 5 mL of THF, was added 0.38 mL of TBAF solution in THF (1 M). The reaction mixture was heated to reflux overnight, cooled to RT, diluted with EtOAc, washed with brine (×2), dried (MgSO$_4$), and concentrated. Chromatography over 10 g SiO$_2$ (80% EtOAc/Hexanes) gave (5-methoxy-3-methyl-1H-indol-2-yl)(3-methyl-1H-indol-5-yl)methanone (19 mg, 0.060 mmol, 80%) as an off white solid. $^1$H NMR (399 MHz, DMSO-d$_6$) δ ppm 11.24 (1H, s), 11.14 (1H, br. s.), 7.94 (1H, s), 7.53 (1H, dd, J=8.6, 1.6 Hz), 7.43 (1H, d, J=8.6 Hz), 7.30 (1H, d, J=8.6 Hz), 7.22 (1H, s), 7.05 (1H, d, J=2.3 Hz), 6.89 (1H, dd, J=9.0, 2.3 Hz), 3.77 (3H, s), 2.25 (3H, d, J=1.2 Hz), 2.22 (3H, s); MS (ESI) m/z Calculated 318.14 Found 319.11 (M+H)+.

Example 7

(3-chloro-5-methoxy-1H-indol-2-yl)(3-methyl-1H-indol-5-yl)methanone

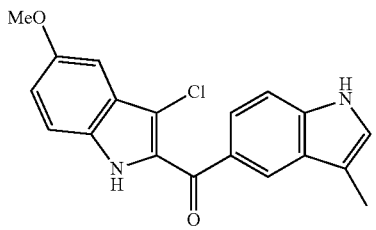 [SMILES: COc1ccc2[nH]c(C(=O)c3ccc4[nH]cc(C)c4c3)c(Cl)c2c1]

To a solution of (5-methoxy-1H-indol-2-yl)(3-methyl-1H-indol-5-yl)methanone (106 mg, 0.348 mmol) in 3 mL of DMF, were added N-Chlorosuccinimide (49 mg, 0.37 mmol). The reaction mixture was stirred at RT for 16 hr, and partitioned between EtOAc and brine. The organic layer was washed with brine (×2), dried (MgSO$_4$), and concentrated. Chromatography over 10 g SiO$_2$ (60% EtOAc/Hexanes) gave (3-chloro-5-methoxy-1H-indol-2-yl)(3-methyl-1H-indol-5-yl)methanone (44 mg, 0.13 mmol, 37%) as an off white solid. $^1$H NMR (399 MHz, DMSO-d$_6$) δ ppm 12.03 (1H, s), 11.76 (1H, s), 8.11 (1H, d, J=1.6 Hz), 7.74 (1H, dd, J=8.4, 1.8 Hz), 7.42 (1H, d, J=9.0 Hz), 7.39 (1H, d, J=8.6 Hz), 7.16 (1H, d, J=2.7 Hz), 7.04 (1H, d, J=1.2 Hz), 6.87-6.96 (1H, m), 3.76 (3H, s), 2.26 (3H, s); MS (ESI) m/z Calculated 338.08 Found 339.14 (M+H)+.

Example 8

(3-((dimethylamino)methyl)-1H-indol-5-yl)(5-methoxy-1H-indol-2-yl)methanone

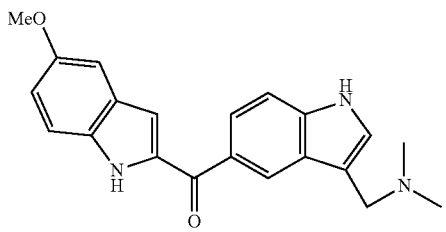 [SMILES: COc1ccc2[nH]c(C(=O)c3ccc4[nH]cc(CN(C)C)c4c3)cc2c1]

1. To round bottom flask was charged sequentially with 1,4-dioxane (52 mL), acetic acid (52 mL), 37% wt. aqueous formaldehyde (4 mL, 54 mmol), and H$_2$O (4 mL). Then, 40% wt. aqueous dimethyl amine (7.1 mL, 56 mmol) was added at 0° C. To this cooled solution was added a solution of 5-bromo-1H-indole (10 g, 51 mmol) in 1,4-dioxane (52 mL) slowly. After 2 hr at 0° C., the reaction mixture was stirred at RT for overnight. The reaction mixture was diluted with H$_2$O (640 mL) and 2M NaOH (500 mL). The resulting precipitate was filtered, and washed with H$_2$O (3×200 mL), Hexanes (200 mL). The collected solid was dried under vacuum to give 1-(5-bromo-1H-indol-3-yl)-N,N-dimethylmethanamine (12.5 g, 97%). $^1$H NMR (400 MHz, DMSO-d$_6$) δ ppm: 11.12 (s, 1H), 7.72 (s, 1H), 7.30 (d, J=8.4 Hz, 1H), 7.24 (s, 1H), 7.15 (dd, J=8.8, 2.0 Hz, 1H), 3.46 (s, 2H), 2.10 (s, 6H).

2. To a solution of 1-(5-bromo-1H-indol-3-yl)-N,N-dimethylmethanamine (2.5 g, 9.88 mmol) in 55 mL of THF, was added sodium hydride (60 wt % dispersion, 475 mg, 11.9 mmol) at 0° C. After 30 min, the reaction was added 9.4 mL of n-BuLi solution in hexanes (2.5 M) at −10° C. After 1 hr, DMF (7.7 mL) was added and allowed to warm to RT. After 2 hr, the reaction was quenched with water, and extracted with EtOAc (×3). The combined organic extracts were washed with water (×3), dried (MgSO$_4$), and concentrated to give 3-((dimethylamino)methyl)-1H-indole-5-carbaldehyde (1.4 g, 70%). $^1$H NMR (400 MHz, DMSO-d$_6$) δ ppm: 11.42 (s, 1H), 9.95 (s, 1H), 8.21 (s, 1H), 7.61 (dd, J=8.4, 1.6 Hz, 1H), 7.48 (d, J=8.4 Hz, 1H), 7.37 (d, J=2.0 Hz, 1H) 3.56 (s, 2H), 2.14 (s, 6H).

3. The mixture of 3-((dimethylamino)methyl)-1H-indole-5-carbaldehyde (1.38 g, 6.8 mmol), Di-tert-butyl dicarbonate (1.94 g, 8.8 mmol), and DMAP (58.5 mg, 0.478 mmol) in 30 mL of THF was stirred at RT for overnight. The reaction mixture was poured into water, and extracted with EtOAc (×3). The combined organic extracts were dried (MgSO$_4$), filtered, and concentrated. Flash chromatography (CH$_2$Cl$_2$/(MeOH/10% NH$_4$OH):100/0-95/5) gave tert-butyl 3-((dimethylamino)methyl)-5-formyl-1H-indole-1-carboxylate (1.1 g, 53%). $^1$H NMR (400 MHz, CDCl$_3$) δ ppm: 10.06 (s, 1H), 8.26 (d, J=8.4 Hz, 1H), 8.21 (s, 1H), 7.85 (dd, J=8.8, 1.6 Hz, 1H), 7.56 (s, 1H), 3.56 (s, 2H), 2.28 (s, 6H), 1.66 (s, 9H).

4. The mixture of tert-butyl 3-((dimethylamino)methyl)-5-(hydroxy(5-methoxy-1-(phenylsulfonyl)-1H-indol-2-yl)methyl)-1H-indole-1-carboxylate (1.72 g, 2.90 mmol), and MnO$_2$ (9 g, 103 mmol) in 60 mL of dichloromethane was stirred overnight at RT, diluted with dichloromethane, filtered through a pad of Celite, and concentrated. Flash chromatography (CH$_2$Cl$_2$/(MeOH/10% NH$_4$OH):100/0-95/5) gave tert-butyl 3-((dimethylamino)methyl)-5-(5-methoxy-1-(phenylsulfonyl)-1H-indole-2-carbonyl)-1H-indole-1-carboxylate (1.4 g, 81%). $^1$H NMR (400 MHz, CDCl$_3$) δ ppm: 8.35 (s, 1H), 8.20 (d, J=8.4 Hz, 1H), 8.05-7.99 (m, 3H), 7.90 (dd, J=8.8, 2.0 Hz, 1H), 7.57 (s, 1H), 7.54 (t, J=7.2 Hz, 1H), 7.45 (t, J=7.6 Hz, 2H), 7.06 (dd, J=9.2, 2.4 Hz, 1H), 6.97 (d, J=2.4 Hz, 1H), 6.85 (s, 1H), 3.81 (s, 3H), 3.56 (s, 2H), 2.27 (s, 6H), 1.66 (s, 9H).

5. To a solution of 5-methoxy-1-(phenylsulfonyl)-1H-indole (1.5 g, 5.21 mmol) in 20 mL of THF, was added 2.19 mL of n-BuLi solution in hexanes (2.5 M) at −78° C. After 1 hr, a solution of tert-butyl 3-((dimethylamino)methyl)-5-formyl-1H-indole-1-carboxylate (1.57 g, 5.21 mmol) in 20 mL of THF was added slowly. The reaction mixture was allowed to warm up to 0° C. slowly. After 1 hr, the reaction was quenched with water, and extracted with EtOAc (×3). The combined organic extracts were dried (MgSO$_4$), filtered, and concentrated. Flash chromatography (CH$_2$Cl$_2$/(MeOH/10% NH$_4$OH):97/3-97/10) gave tert-butyl 3-((dimethylamino)methyl)-5-(hydroxy(5-methoxy-1H-indol-2-yl)methyl)-1H-indole-1-carboxylate (140 mg, 6%) as minor product and tert-butyl 3-((dimethylamino)methyl)-5-(hydroxy(5-methoxy-1-(phenylsulfonyl)-1H-indol-2-yl)methyl)-1H-indole-1-carboxylate (1.72 g, 56%) as major product. $^1$H NMR (400 MHz, CDCl$_3$) δ ppm: 8.46 (s, 1H), 8.07 (d, J=7.2 Hz, 1H), 7.88 (s, 1H), 7.48 (s, 1H), 7.32 (dd, J=8.8, 1.6 Hz, 1H), 7.10 (d, J=8.4 Hz, 1H), 6.96 (d, J=2.4 Hz, 1H), 6.75 (dd, J=9.2, 2.8 Hz, 1H), 6.22 (s, 1H), 6.09 (s, 1H), 3.79 (s, 3H), 3.51 (q, J=8.8 Hz, 2H), 2.25 (s, 7H), 1.64 (s, 9H).

6. The mixture of tert-butyl 3-((dimethylamino)methyl)-5-(hydroxy(5-methoxy-1H-indol-2-yl)methyl)-1H-indole-1-carboxylate (140 mg, 0.312 mmol), and MnO$_2$ (542 mg, 6.23 mmol) in 9 mL of dichloromethane was stirred overnight at RT, diluted with dichloromethane, filtered through a pad of Celite, and concentrated to give tert-butyl 3-((dimethylamino)methyl)-5-(5-methoxy-1H-indole-2-carbonyl)-1H-indole-1-carboxylate (126.4 mg, 91%). $^1$H NMR (400 MHz, CDCl$_3$) δ ppm: 9.19 (s, 1H), 8.34 (s, 1H), 8.25 (d, J=8.4 Hz, 1H), 7.97 (dd, J=8.4, 1.6 Hz, 1H), 7.59 (s, 1H), 7.37 (d, J=8.8 Hz, 1H), 7.12-7.07 (m, 2H), 7.04 (dd, J=9.2, 2.8 Hz, 1H), 3.85 (s, 3H), 3.60 (s, 2H), 2.30 (s, 6H), 1.68 (s, 9H).

7. The mixture of tert-butyl 3-((dimethylamino)methyl)-5-(5-methoxy-1H-indole-2-carbonyl)-1H-indole-1-carboxylate (127 mg, 0.282 mmol), and TFA (0.9 mL, 12.7 mmol) in 4 mL of dichloromethane was stirred 6 hr at RT, diluted with dichloromethane, and concentrated. The reaction mixture was dissolved with EtOAc, and poured into saturated sodium bicarbonate, extracted with EtOAc (×3). The combined organic extracts were dried (MgSO$_4$), filtered, and concentrated. Flash chromatography (CH$_2$Cl$_2$/(MeOH/10% NH$_4$OH):97/3-97/10) gave (3-((dimethylamino)methyl)-1H-indol-5-yl)(5-methoxy-1H-indol-2-yl)methanone (94 mg, 98%). $^1$H NMR (400 MHz, DMSO-d$_6$) δ ppm: 11.72 (s, 1H), 11.30 (s, 1H), 8.28 (s, 1H), 7.71 (dd, J=8.4, 1.6 Hz, 1H), 7.48 (d, J=8.4 Hz, 1H), 7.38 (d, J=9.2 Hz, 1H), 7.35 (d, J=2.0 Hz, 1H), 7.13 (d, J=2.4 Hz, 1H), 6.98 (d, J=1.2 Hz, 1H), 6.93 (dd, J=8.8, 2.4 Hz, 1H), 3.74 (s, 3H), 3.57 (s, 2H), 2.14 (s, 6H).

Example 9

(3-chloro-1H-indol-5-yl)(5-methoxy-1H-indol-2-yl)methanone

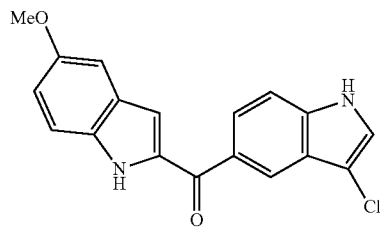 [SMILES: COc1ccc2[nH]c(C(=O)c3ccc4[nH]cc(Cl)c4c3)cc2c1]

1. To a solution of 1H-indole-5-carbaldehyde (1.45 g, 10.0 mmol) in 100 mL of 1,4-dioxane, were added N-Chlorosuccinimide (1.47 g, 11.0 mmol). The reaction mixture was stirred at RT for 18 hr, and concentrated. The residue was purified over 100 g SiO$_2$ (80% EtOAc/Hexanes) to give 3-chloro-1H-indole-5-carbaldehyde (0.585 g, 3.26 mmol, 33%) as a brown solid. $^1$H NMR (399 MHz, DMSO-d$_6$) δ ppm 11.85 (1H, br. s.), 10.00 (1H, s), 8.03-8.13 (1H, m), 7.63-7.71 (2H, m), 7.55 (1H, d, J=8.6 Hz)

2. To a cooled solution of 3-chloro-1H-indole-5-carbaldehyde (0.585 g, 3.26 mmol) in 10 mL of THF, was added sodium hydride (60 wt % dispersion, 0.133 g, 3.33 mmol) at 0° C. After 1 hr, phenylsulfonylchloride (0.43 mL, 3.33 mmol) was added. After 1 hr, the reaction was quenched with saturated sodium bicarbonate solution, and extracted with EtOAc. The organic layer was dried (MgSO$_4$), and concentrated. The residue was purified over 50 g SiO$_2$ (50% EtOAc/Hexanes) to give 3-chloro-1-(phenylsulfonyl)-1H-indole-5-carbaldehyde (0.755 g, 2.36 mmol, 72%) as a brown solid. $^1$H NMR (399 MHz, CHLOROFORM-d) δ ppm 10.07 (1H, s), 8.14 (1H, d, J=8.6 Hz), 8.08-8.11 (1H, m), 8.02-8.08 (1H, m), 7.88-7.99 (2H, m), 7.75 (1H, t, J=7.4 Hz), 7.55-7.70 (2H, m), 7.45-7.55 (1H, m)

3. To a solution of 5-methoxy-1-(phenylsulfonyl)-1H-indole (261 mg, 0.91 mmol) in 6 mL of THF, was added 0.76 mL of n-BuLi solution in hexanes (1.8 M) at −78° C. After 1 hr, a solution of 3-chloro-1-(phenylsulfonyl)-1H-indole-5-carbaldehyde (320 mg, 1.00 mmol) in 2 mL of THF was added slowly. After 4 hr, the reaction mixture was allowed to warm up to RT slowly, quenched with saturated ammonium chloride solution, and extracted with EtOAc. The organic layer was dried (MgSO$_4$), and concentrated. Chromatography over 50 g SiO$_2$ (60% EtOAc/Hexanes) gave (3-chloro-1-(phenylsulfonyl)-1H-indol-5-yl)(5-methoxy-1-(phenylsulfonyl)-1H-indol-2-yl)methanol (298 mg, 0.491 mmol, 54%) as a brownish oil. $^1$H NMR (399 MHz, CHLOROFORM-d) δ ppm 7.96 (1H, d, J=8.6 Hz), 7.99 (1H, d, J=9.0 Hz), 7.84-7.95 (2H, m), 7.61-7.68 (3H, m), 7.54-7.61 (2H, m), 7.44-7.53 (4H, m), 7.39 (1H, dd, J=8.8, 1.8 Hz), 7.30 (2H, t, J=7.8 Hz), 6.91 (1H, dd, J=9.2, 2.5 Hz), 6.81 (1H, d, J=2.7 Hz), 6.42 (1H, d, J=4.7 Hz), 6.10 (1H, s), 3.68-3.81 (3H, m)

4. The mixture of (3-chloro-1-(phenylsulfonyl)-1H-indol-5-yl)(5-methoxy-1-(phenylsulfonyl)-1H-indol-2-yl)methanol and MnO₂ (854 mg, 9.82 mmol) in 20 mL of dichloromethane was stirred overnight at RT, diluted with dichloromethane, filtered through a pad of Celite, and concentrated to give (3-chloro-1-(phenylsulfonyl)-1H-indol-5-yl)(5-methoxy-1-(phenylsulfonyl)-1H-indol-2-yl)methanone (297 mg, quant.) as a dark brown solid. ¹H NMR (399 MHz, CHLOROFORM-d) δ ppm 8.15-8.20 (1H, m), 8.07-8.12 (1H, m), 7.96-8.05 (4H, m), 7.86-7.96 (2H, m), 7.41-7.70 (7H, m), 7.09 (1H, dd, J=9.2, 2.5 Hz), 6.99 (1H, d, J=2.3 Hz), 6.88 (1H, s), 3.83 (3H, s)

5. To a solution (3-chloro-1-(phenylsulfonyl)-1H-indol-5-yl)(5-methoxy-1-(phenylsulfonyl)-1H-indol-2-yl)methanone in 5 mL of THF, was added 2.5 mL of TBAF solution in THF (1 M). The reaction mixture was heated to reflux overnight, cooled to RT, diluted with EtOAc, washed with brine (×2), dried (MgSO₄), and concentrated. Chromatography over 25 g SiO₂ (80% EtOAc/Hexanes) gave (3-chloro-1H-indol-5-yl)(5-methoxy-1H-indol-2-yl)methanone (71 mg, 0.219 mmol, 45%) as a bright brown solid. ¹H NMR (399 MHz, DMSO-d₆) δ 11.80 (1H, s), 11.78 (1H, s), 8.07-8.14 (1H, m), 7.80 (1H, dd, J=8.6, 1.6 Hz), 7.70 (1H, d, J=2.7 Hz), 7.59 (1H, d, J=8.6 Hz), 7.39 (1H, d, J=9.0 Hz), 7.18 (1H, d, J=2.3 Hz), 7.03 (1H, d, J=1.6 Hz), 6.95 (1H, dd, J=8.8, 2.5 Hz), 3.76 (3H, s); MS (ESI) m/z Calculated 324.07 Found 325.00 (M+H)+.

Example 10

(3-chloro-1H-indol-5-yl)(3,4-dichloro-5-methoxy-1H-indol-2-yl)methanone and (3-chloro-1H-indol-5-yl)(3-chloro-5-methoxy-1H-indol-2-yl)methanone

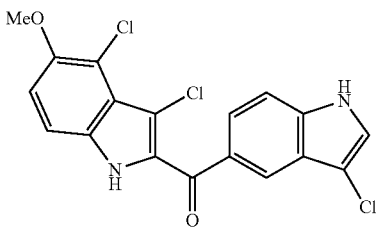

To a solution of (1H-indol-5-yl)(5-methoxy-1H-indol-2-yl)methanone (250 mg, 0.86 mmol) in DMF (7 mL) at 0° C. was added N-Chlorosuccinimide (298 mg, 2.23 mmol). The reaction mixture was stirred at RT for 3 hr. The reaction mixture was poured into brine, and extracted with EtOAc (×3). The combined organic extracts were washed with water (×2), filtered (MgSO₄), filtered, and concentrated. Flash chromatography (EtOAc/DCM/Hexanes:25%/20%/55%) gave (3-chloro-1H-indol-5-yl)(3,4-dichloro-5-methoxy-1H-indol-2-yl)methanone (48 mg, 14.2%) and (3-chloro-1H-indol-5-yl)(3-chloro-5-methoxy-1H-indol-2-yl)methanone (202 mg, 65.3%). (3-chloro-1H-indol-5-yl)(3-chloro-5-methoxy-1H-indol-2-yl)methanone: ¹H NMR (400 MHz, DMSO-d₆) δ ppm: 12.00 (s, 1H), 11.81 (s, 1H), 7.99 (s, 1H), 7.71-7.67 (m, 2H), 7.58 (d, J=8.4 Hz, 1H), 7.42 (d, J=8.8 Hz, 1H), 7.04-6.98 (m, 2H), 3.81 (s, 3H). (3-chloro-1H-indol-5-yl)(3,4-dichloro-5-methoxy-1H-indol-2-yl)methanone: ¹H NMR (400 MHz, DMSO-d₆) δ ppm: 12.78 (s, 1H), 12.02 (s, 1H), 7.93 (s, 1H), 7.72 (dd, J=8.8, 1.6 Hz, 1H), 7.53 (d, J=8.4 Hz, 1H), 7.42 (d, J=9.6 Hz, 1H), 7.03 (dd, J=8.8, 2.4 Hz, 1H), 6.99 (d, J=2.4 Hz, 1H), 3.80 (s, 3H). MS: 393.06, 395.07 (M+H+).

Example 11

(5-hydroxy-1H-indol-2-yl)(1H-indol-5-yl)methanone

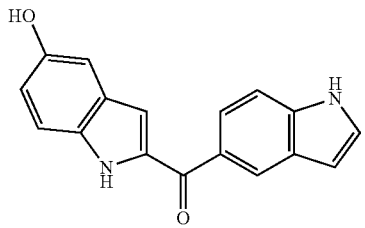 [SMILES: O=C(c1ccc2[nH]ccc2c1)c1cc2cc(O)ccc2[nH]1]

To a solution of (1H-indol-5-yl)(5-methoxy-1H-indol-2-yl)methanone (100 mg, 0.344 mmol) in dichloromethane 18 mL was added 2 mL of BBr₃ (1.0 M in methylene chloride) at 0° C. The reaction mixture was stirred at RT for overnight. After overnight, another 2 mL of BBr₃ (1.0 M in methylene chloride) was added to reaction mixture at 0° C., and stirred at RT for 5 hr. The reaction mixture was poured into water, and extracted with EtOAc (×3). The combined organic extracts were washed with water (×2), dried (MgSO₄), filtered, and concentrated. Flash chromatography (60% EtOAc/Hexanes) gave (5-hydroxy-1H-indol-2-yl)(3-methyl-1H-indol-5-yl)methanone (16.4 mg, 17.2%). ¹H NMR (400 MHz, DMSO-d₆) δ ppm: 11.56 (s, 1H), 11.46 (s, 1H), 8.92 (s, 1H), 8.24 (s, 1H), 7.70 (dd, J=8.4, 1.6 Hz, 1H), 7.53 (d, J=8.8 Hz, 1H), 7.47 (t, J=2.8 Hz, 1H), 7.31 (d, J=9.2 Hz, 1H), 6.95 (dd, J=7.2, 1.6 Hz, 2H), 6.83 (dd, J=8.8, 2.4 Hz, 1H), 6.63 (s, 1H).

Example 12

(5-hydroxy-1H-indol-2-yl)(3-methyl-1H-indol-5-yl)methanone

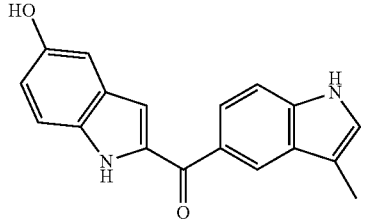 [SMILES: Cc1c[nH]c2ccc(C(=O)c3cc4cc(O)ccc4[nH]3)cc12]

To a solution of (5-methoxy-1H-indol-2-yl)(3-methyl-1H-indol-5-yl)methanone (55 mg, 0.181 mmol) in dichloromethane 20 mL was added 1 mL of BBr₃ (1.0 M in methylene chloride) at 0° C. The reaction mixture was stirred at RT for overnight. The reaction mixture was poured into water, and extracted with EtOAc (×3). The combined organic extracts were washed with water (×2), dried (MgSO$_4$), filtered, and concentrated. Flash chromatography (60% EtOAc/Hexanes) gave (5-hydroxy-1H-indol-2-yl)(3-methyl-1H-indol-5-yl)methanone (45.9 mg, 88%). $^1$H NMR (400 MHz, DMSO-d$_6$) δ ppm: 11.57 (s, 1H), 11.14 (s, 1H), 8.92 (s, 1H), 8.14 (s, 1H), 7.71 (dd, J=8.4, 1.6 Hz, 1H), 7.46 (d, J=8.8 Hz, 1H), 7.31 (d, J=9.2 Hz, 1H), 7.24 (s, 1H), 6.95 (dd, J=7.2, 1.6 Hz, 2H), 6.83 (dd, J=8.8, 2.4 Hz, 1H), 2.31 (s, 3H). MS: 291.07 (M+H+).

Example 13

(5-(2-(dimethylamino)ethoxy)-1H-indol-2-yl)(3-methyl-1H-indol-5-yl)methanone hydrochloride

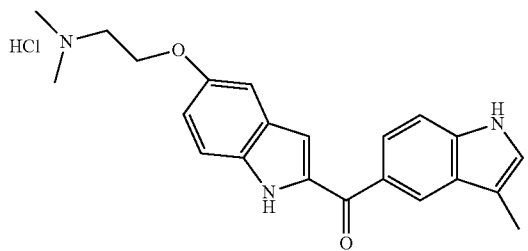 [SMILES: Cl ; Cc1c[nH]c2ccc(C(=O)c3cc4cc(OCCN(C)C)ccc4[nH]3)cc12]

1. The mixture of (5-hydroxy-1H-indol-2-yl)(3-methyl-1H-indol-5-yl)methanone (108 mg, 3.74 mmol), Di-tert-butyl dicarbonate (326.9 mg, 1.5 mmol), and DMAP (4.6 mg, 0.37 mmol) in 5 mL of THF was stirred at RT for over weekend. The reaction mixture was poured into water, and extracted with EtOAc (×3). The combined organic extracts were dried (MgSO$_4$), filtered, and concentrated to give crude tert-butyl 2-(1-(tert-butoxycarbonyl)-3-methyl-1H-indole-5-carbonyl)-5-((tert-butoxycarbonyl)oxy)-1H-indole-1-carboxylate (215.6 mg). The mixture of crude tert-butyl 2-(1-(tert-butoxycarbonyl)-3-methyl-1H-indole-5-carbonyl)-5-((tert-butoxycarbonyl)oxy)-1H-indole-1-carboxylate (215.6 mg) and morpholine (0.959 mL, 10.96 mmol) in dichloromethane (2.5 mL) was stirred at RT for over weekend. The reaction mixture was poured into water, and extracted with EtOAc (×3). The combined organic extracts were dried (MgSO$_4$), filtered, and concentrated. Flash chromatography (20% EtOAc/Hexanes) gave tert-butyl 2-(1-(tert-butoxycarbonyl)-3-methyl-1H-indole-5-carbonyl)-5-hydroxy-1H-indole-1-carboxylate (167.8 mg) contained tert-butyl morpholine-4-carboxylate as by product. (1:1 ratio). The material was used without farther purification. $^1$H NMR (400 MHz, CDCl$_3$) δ ppm: 9.28 (s, 1H), 8.25 (d, J=8.4 Hz, 1H), 8.17 (s, 1H), 7.99 (dd, J=8.4, 1.6 Hz, 1H), 7.53 (s, 1H), 7.47 (d, J=8.8 Hz, 1H), 7.47 (d, J=8.8 Hz, 1H), 7.45 (s, 1H), 7.20 (dd, J=9.2, 2.4 Hz, 1H), 7.16 (s, 1H), 2.33 (s, 3H), 1.69 (s, 9H), 1.58 (s, 9H).

2. The mixture of tert-butyl 2-(1-(tert-butoxycarbonyl)-3-methyl-1H-indole-5-carbonyl)-5-hydroxy-1H-indole-1-carboxylate contained tert-butyl morpholine-4-carboxylate (167.8 mg), 2-Chloro-N,N-dimethylethylamine hydrochloride (94 mg, 0.65 mmol), and CsCO$_3$ (423 mg, 1.30 mmol) in 5 mL of DMF was stirred at 50° C. overnight. The reaction mixture was poured into water, and extracted with EtOAc (×3). The combined organic extracts were washed with water (×2), dried (MgSO$_4$), filtered, and concentrated. The crude material was dissolved with dichloromethane (6.5 mL), and was added Di-tert-butyl dicarbonate (177 mg, 0.81 mmol) followed by DMAP (15 mg, 0.37 mmol). The reaction mixture was stirred at RT for overnight, and poured into water, and extracted with EtOAc (×3). The combined organic extracts were dried (MgSO$_4$), filtered, and concentrated. Flash chromatography (CH$_2$Cl$_2$/(MeOH/10% NH$_4$OH):100/0-95/5) gave tert-butyl 2-(1-(tert-butoxycarbonyl)-3-methyl-1H-indole-5-carbonyl)-5-(2-(dimethylamino)ethoxy)-1H-indole-1-carboxylate (100 mg, 48% for three step). $^1$H NMR (400 MHz, CDCl$_3$) δ ppm: 8.20 (d, J=8.4 Hz, 1H), 8.10 (s, 1H), 7.91 (dd, J=8.8, 1.6 Hz, 1H), 7.49-7.42 (m, 3H), 7.20 (dd, J=9.2, 2.4 Hz, 1H), 6.92 (s, 1H), 4.64 (t, J=6.8 Hz, 2H), 2.69 (t, J=6.8 Hz, 2H), 2.30 (s, 3H), 2.27 (s, 6H), 1.68 (s, 9H), 1.46 (s, 9H).

3. The mixture of tert-butyl 2-(1-(tert-butoxycarbonyl)-3-methyl-1H-indole-5-carbonyl)-5-(2-(dimethylamino)ethoxy)-1H-indole-1-carboxylate (100 mg, 0.178 mmol) and TFA (0.962 mL, 12.9 mmol) in 9 mL of dichloromethane was stirred overnight at RT, diluted with dichloromethane, and concentrated to ~10 mL. The reaction mixture was poured into H$_2$O/sat. NaHCO$_3$ (1/1), and the precipitate was filtered, washed with water, Hexanes, dried under vacuum (51.2 mg, 80%). $^1$H NMR (400 MHz, Acetone-d$_6$) δ ppm: 8.20 (s, 1H), 7.96 (br.s, 1H), 7.78 (dd, J=8.8, 2.0 Hz, 1H), 7.50 (d, J=8.8 Hz, 1H), 7.46 (d, J=8.8 Hz, 1H), 7.24 (s, 1H), 7.06 (d, J=2.4 Hz, 1H), 6.99 (dd, J=9.2, 2.4 Hz, 1H), 6.78 (s, 1H), 4.64 (t, J=6.8 Hz, 2H), 2.61 (t, J=6.8 Hz, 2H), 2.34 (s, 3H), 2.16 (s, 6H). MS: 362.18 (M+H+).

4. To a solution of (5-(2-(dimethylamino)ethoxy)-1H-indol-2-yl)(3-methyl-1H-indol-5-yl) methanone (13.2 mg) in 2.5 ml MeOH was added 73 µl of HCl solution in ethyl ether (2 M). The solvent was evaporated, and dried under vacuum to give (5-(2-(dimethylamino)ethoxy)-1H-indol-2-yl)(3-methyl-1H-indol-5-yl)methanone hydrochloride (14 mg, 96%). $^1$H NMR (400 MHz, DMSO-d$_6$) δ ppm: 11.20 (s, 1H), 10.44 (br.s, 1H), 9.14 (s, 1H), 8.08 (s, 1H), 7.67 (d, J=8.8 Hz, 1H), 7.61 (d, J=8.8 Hz, 1H), 7.45 (d, J=8.4 Hz, 1H), 7.24 (s, 1H), 6.99 (s, 1H), 6.95 (dd, J=8.8, 2.0 Hz, 1H), 6.89 (s, 1H), 4.77 (t, J=7.6 Hz, 2H), 3.45 (t, J=8.4 Hz, 2H), 2.85 (s, 6H), 2.26 (s, 3H).

Example 14

(1H-indol-5-yl)(5-morpholino-1H-indol-2-yl)methanone

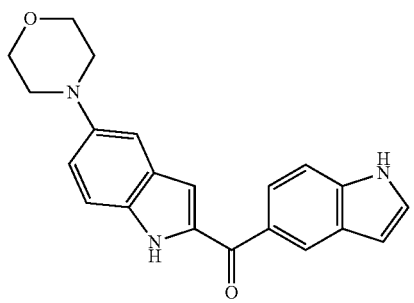 [SMILES: O=C(c1ccc2[nH]ccc2c1)c1cc2cc(N3CCOCC3)ccc2[nH]1]

1. To a cooled solution of 5-bromo-1H-indole (1.96 g, 10.0 mmol) in 14 mL of THF, was added sodium hydride (60 wt % dispersion, 408 mg, 10.2 mmol) at 0° C. After 1 hr, phenylsulfonylchloride (1.3 mL, 10.2 mmol) was added. After 1 hr, the reaction was quenched with saturated sodium bicarbonate solution, and extracted with ethyl ether. The organic layer was dried (MgSO$_4$), and concentrated. The residue was recrystallized from EtOH to give 5-bromo-1-(phenylsulfonyl)-1H-indole (2.38 g, 7.08 mmol, 71%) as a white solid. $^1$H NMR (399 MHz, CHLOROFORM-d) δ ppm 7.81-7.91 (3H, m), 7.66 (1H, d, J=1.6 Hz), 7.50-7.59 (2H, m), 7.34-7.49 (3H, m), 6.60 (1H, d, J=4.3 Hz)

2. To a slurry of 5-bromo-1-(phenylsulfonyl)-1H-indole (336 mg, 1.00 mmol), CuI (38 mg, 0.20 mmol), potassium carbonate (415 mg, 3.00 mmol), and DL-proline (46 mg, 0.40 mmol) in 5 mL of THF, was added morpholine (0.18 mL, 2.00 mmol). The reaction mixture was stirred overnight at 120° C., cooled to RT, diluted with EtOAc, and washed with water. The aqueous layer was extracted with EtOAc. The combined organic layer was dried (MgSO$_4$), and concentrated. Chromatography over 10 g SiO$_2$ (60% EtOAc/Hexanes) gave 4-(1-(phenylsulfonyl)-1H-indol-5-yl)morpholine (151 mg, 0.441 mmol, 44%) as a colorless oil. $^1$H NMR (399 MHz, CHLOROFORM-d) δ ppm 7.89 (1H, d, J=8.8 Hz), 7.82-7.87 (2H, m), 7.48-7.52 (2H, m), 7.39-7.44 (2H, m), 6.99-7.01 (2H, m), 6.57 (1H, d, J=4.0 Hz), 3.86 (4H, t, J=4.8 Hz), 3.12 (4H, t, J=4.8 Hz)

3. To a solution of 4-(1-(phenylsulfonyl)-1H-indol-5-yl) morpholine (150 mg, 0.438 mmol) in 3 mL of THF, was added 0.19 mL of n-BuLi solution in hexanes (2.5 M) at −78° C. After 1 hr, a solution of 1-(phenylsulfonyl)-1H-indole-5-carbaldehyde (527 mg, 1.85 mmol) in 6 mL of THF was added slowly. After 1 hr, the reaction mixture was allowed to warm up to RT slowly, quenched with saturated ammonium chloride solution, and extracted with EtOAc. The organic layer was dried (MgSO$_4$), and concentrated. Chromatography over 10 g SiO$_2$ (100% EtOAc/Hexanes) gave (5-morpholino-1-(phenylsulfonyl)-1H-indol-2-yl)(1-(phenylsulfonyl)-1H-indol-5-yl)methanol (54 mg, 0.086 mmol, 20%) as an oil, which was solidified later $^1$H NMR (399 MHz, CHLOROFORM-d) δ ppm 7.82-8.03 (4H, m), 7.49-7.67 (4H, m), 7.35-7.49 (3H, m), 7.26-7.32 (4H, m), 6.97 (1H, dd, J=9.2, 2.5 Hz), 6.82 (1H, d, J=2.3 Hz), 6.61 (1H, d, J=3.5 Hz), 6.39 (1H, s), 6.14 (1H, s), 3.74-3.98 (3H, m), 2.97-3.25 (3H, m)

4. The mixture of (5-morpholino-1-(phenylsulfonyl)-1H-indol-2-yl)(1-phenylsulfonyl)-1H-indol-5-yl)methanol and MnO$_2$ (447 mg, 5.14 mmol) in 6 mL of dichloromethane was stirred overnight at RT, diluted with dichloromethane, filtered through a pad of Celite, and concentrated to give (5-morpholino-1-(phenylsulfonyl)-1H-indol-2-yl)(1-(phenylsulfonyl)-1H-indol-5-yl)methanone (20 mg, 0.032 mmol, 37%) as an oil. $^1$H NMR (399 MHz, CHLOROFORM-d) δ ppm 7.96-8.14 (5H, m), 7.86-7.95 (3H, m), 7.65 (1H, d, J=3.5 Hz), 7.51-7.61 (2H, m), 7.41-7.51 (4H, m), 7.14 (1H, dd, J=9.2, 2.5 Hz), 6.92-7.02 (1H, m), 6.83 (1H, s), 6.73 (1H, d, J=3.1 Hz), 3.79-3.96 (4H, m), 3.05-3.24 (4H, m)

5. To a solution (5-morpholino-1-(phenylsulfonyl)-1H-indol-2-yl)(1-phenylsulfonyl)-1H-indol-5-yl)methanone (20 mg, 0.032 mmol) in 3 mL of THF, was added 0.32 mL of TBAF solution in THF (1 M). The reaction mixture was heated at 70° C. overnight, cooled to RT, diluted with EtOAc, washed with brine (×2), dried (MgSO$_4$), and concentrated. Chromatography over 10 g SiO$_2$ (80% EtOAc/Hexanes) gave (1H-indol-5-yl)(5-morpholino-1H-indol-2-yl)methanone (5 mg, 0.015 mmol, 45%) as an off white solid. $^1$H NMR (399 MHz, DMSO-d$_6$) δ ppm 12.06 (1H, s), 11.51 (1H, br. s.), 8.24-8.31 (1H, m), 7.78 (1H, d, J=2.0 Hz), 7.73 (1H, dd, J=8.6, 1.6 Hz), 7.55 (1H, d, J=8.6 Hz), 7.46-7.52 (2H, m), 7.28 (1H, dd, J=8.6, 2.0 Hz), 7.10-7.14 (1H, m), 6.64 (1H, t, J=2.0 Hz); MS (ESI) m/z Calculated 345.15 Found 346.17 (M+H)+.

Example 15

(5,6-dimethoxy-1H-indol-2-yl)(1H-indol-5-yl)methanone

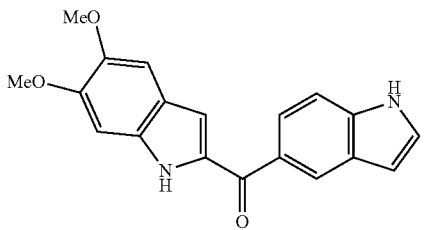 [SMILES: COc1cc2cc(C(=O)c3ccc4[nH]ccc4c3)[nH]c2cc1OC]

1. To a solution of ethyl 5,6-dimethoxy-1H-indole-2-carboxylate (935 mg, 3.75 mmol) in 20 mL of THF, was added LiAlH$_4$ (229 mg, 6.02 mmol) at 0° C. After 2 hr at RT, the reaction mixture was quenched with saturated ammonium chloride solution (~5 mL) at 0° C., filtered, and concentrated to give crude (5,6-dimethoxy-1H-indol-2-yl) methanol.

The mixture of crude (5,6-dimethoxy-1H-indol-2-yl) methanol and MnO$_2$ (3.26 g, 37.5 mmol) in 25 mL of THF was stirred over weekend at RT. The reaction mixture was filtered through a pad of Celite, and concentrated. Flash chromatograph (50% EtOAc/Hexanes) gave 5,6-dimethoxy-1H-indole-2-carbaldehyde (618 mg, 80% for two step). $^1$H NMR (400 MHz, CDCl$_3$) δ ppm: 6.96 (s, 1H), 8.95 (br.s, 1H), 7.15 (s, 1H), 7.07 (s, 1H), 6.84 (s, 1H), 3.96 (s, 3H), 3.93 (s, 3H).

2. The mixture of 5,6-dimethoxy-1H-indole-2-carbaldehyde (618 mg, 3 mmol), phenylsulfonylchloride (0.423 mL, 3.31 mmol), diisopropylethylamine (2.62 mL, 15.05 mmol), and DMAP (37 mg, 0.30 mmol) in 25 mL of dichloromethane was stirred at RT for overnight, diluted with dichloromethane, washed with water, was dried (MgSO$_4$), and concentrated. The residue was purified by chromatography (EtOAc/DCM/Hexanes:30%/25%/45%)) to give 5,6-dimethoxy-1-(phenylsulfonyl)-1H-indole-2-carbaldehyde (667 mg, 64%). $^1$H NMR (400 MHz, CDCl$_3$) δ ppm: 10.40 (s, 1H), 7.73 (s, 1H), 7.71 (d, J=6.4 Hz, 2H), 7.53 (t, J=7.2 Hz, 1H), 7.43-7.37 (m, 3H), 6.94 (s, 1H), 4.02 (s, 3H), 3.88 (s, 3H).

3. To a solution of 5-bromo-1H-indole (120 mg, 0.608 mmol) in 4 mL of ethyl ether, was added 1.07 mL of t-BuLi solution in pentane (1.7 M) at −78° C. After 1 hr at −78° C., a solution of 5,6-dimethoxy-1-(phenylsulfonyl)-1H-indole-2-carbaldehyde (200 mg, 0.58 mmol) in 20 mL of THF was added slowly. After 0.5 hr at −78° C., the reaction mixture was allowed to warm up to RT, and stirred for another 2 hr. The reaction mixture was quenched with saturated sodium bicarbonate, and extracted with EtOAc (×3). The combined organic extracts were dried (MgSO$_4$), filtered, and concentrated to give crude (5,6-dimethoxy-1-(phenylsulfonyl)-1H-indol-2-yl)(1H-indol-5-yl)methanol. The mixture of crude (5,6-dimethoxy-1-(phenylsulfonyl)-1H-indol-2-yl)(1H-indol-5-yl)methanol and MnO$_2$ (2.12 g, 24.32 mmol) in 35 mL of dichloromethane was stirred overnight at 37° C. The reaction mixture was filtered through a pad of Celite, and concentrated. Flash chromatograph (EtOAc/Hexanes) gave (5,6-dimethoxy-1-(phenylsulfonyl)-1H-indol-2-yl)(1H-indol-5-yl)methanone (92.2 mg, 34% for two step). $^1$H NMR (400 MHz, CDCl$_3$) δ ppm: 8.44 (s, 1H), 8.24 (s, 1H), 8.00 (d, J=8.4 Hz, 1H), 7.89 (d, J=8.4 Hz, 1H), 7.70 (s, 1H), 7.54

(t, J=6.8 Hz, 1H), 7.48-7.41 (m, 3H), 7.27 (t, J=2.8 Hz 1H), 6.93 (s, 1H), 6.86 (s, 1H), 6.62 (s, 1H), 4.02 (s, 3H), 3.88 (s, 3H).

4. To a solution of (5,6-dimethoxy-1-(phenylsulfonyl)-1H-indol-2-yl)(1H-indol-5-yl)methanone (92.2 mg, 0.2 mmol) in 1 mL of THF, was added 3 mL of TBAF solution in THF (1 M). The reaction mixture was refluxed for overnight. After cooled to RT, the reaction mixture was poured into water, and extracted with EtOAc (×3). The combined organic extracts were washed with water, dried (MgSO$_4$), filtered, and concentrated. Flash chromatography (EtOAc/Hexanes) gave (5,6-dimethoxy-1H-indol-2-yl)(1H-indol-5-yl)methanone (54.1 mg, 84%). $^1$H NMR (400 MHz, DMSO-d$_6$) δ ppm: 11.57 (s, 1H), 11.42 (s, 1H), 8.19 (s, 1H), 7.66 (d, J=8.4 Hz, 1H), 7.51 (d, J=8.8 Hz, 1H), 7.45 (t, J=2.8 Hz, 1H), 7.12 (s, 1H), 6.98 (s, 1H), 6.90 (s, 1H), 6.56 (s, 1H), 3.78 (s, 3H), 3.73 (s, 3H).

Example 16

(5-chloro-1H-indol-2-yl)(1H-indol-5-yl)methanone

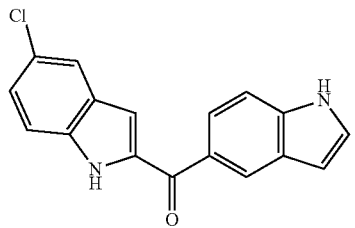 [SMILES: O=C(c1ccc2[nH]ccc2c1)c1cc2cc(Cl)ccc2[nH]1]

1. The mixture of 5-chloro-1H-indole (5.00 g, 33.0 mmol), phenylsulfonylchloride (4.5 mL, 35.3 mmol), diisopropylethylamine (28.7 mL, 165 mmol), and DMAP (403 mg, 3.3 mmol) in 220 mL of dichloromethane was stirred at RT for 18 hr, diluted with dichloromethane, washed with water, was dried (MgSO$_4$), and concentrated. The residue was purified over 100 g SiO$_2$ (50% EtOAc/Hexanes) to give 5-chloro-1-(phenylsulfonyl)-1H-indole (9.81 g, quant.) as an off white solid. $^1$H NMR (399 MHz, CHLOROFORM-d) δ ppm 7.92 (1H, d, J=8.6 Hz), 7.82-7.88 (2H, m), 7.56-7.59 (1H, m), 7.52-7.56 (1H, m), 7.50 (1H, d, J=2.0 Hz), 7.41-7.48 (2H, m), 7.25-7.29 (1H, m), 6.57-6.63 (1H, m)

2. To a solution of 5-chloro-1-(phenylsulfonyl)-1H-indole (490 mg, 1.68 mmol) in 10 mL of THF, was added 0.74 mL of n-BuLi solution in hexanes (2.5 M) at −78° C. After 1 hr, a solution of 1-(phenylsulfonyl)-1H-indole-5-carbaldehyde (527 mg, 1.85 mmol) in 6 mL of THF was added slowly. After 1 hr, the reaction mixture was allowed to warm up to RT slowly, quenched with saturated ammonium chloride solution, and extracted with EtOAc. The organic layer was dried (MgSO$_4$), and concentrated. Chromatography over 25 g SiO$_2$ (50% EtOAc/Hexanes) gave (5-chloro-1-(phenylsulfonyl)-1H-indol-2-yl)(1-(phenylsulfonyl)-1H-indol-5-yl)methanol (282 mg, 0.489 mmol, 29%) as a yellow oil. $^1$H NMR (399 MHz, CHLOROFORM-d) δ ppm 8.02 (1H, d, J=9.0 Hz), 7.85-7.99 (3H, m), 7.53-7.70 (5H, m), 7.41-7.53 (3H, m), 7.27-7.39 (4H, m), 7.22-7.26 (1H, m), 6.62 (1H, d, J=3.5 Hz), 6.43 (1H, d, J=4.3 Hz), 6.21 (1H, s)

3. The mixture of (5-chloro-1-(phenylsulfonyl)-1H-indol-2-yl)(1-(phenylsulfonyl)-1H-indol-5-yl)methanol and MnO$_2$ (850 mg, 9.78 mmol) in 6 mL of dichloromethane was stirred overnight at RT, diluted with dichloromethane, filtered through a pad of Celite, and concentrated to give (5-chloro-1-(phenylsulfonyl)-1H-indol-2-yl)(1-(phenylsulfonyl)-1H-indol-5-yl)methanone (281 mg, 0.489 mmol, 100%) as a yellow solid. $^1$H NMR (399 MHz, CHLOROFORM-d) δ ppm 8.02-8.15 (4H, m), 7.99 (1H, dd, J=8.6, 1.6 Hz), 7.87-7.95 (2H, m), 7.67 (1H, d, J=3.5 Hz), 7.56-7.63 (2H, m), 7.45-7.56 (5H, m), 7.41 (1H, dd, J=9.0, 2.0 Hz), 6.82 (1H, s), 6.74 (1H, d, J=3.5 Hz)

4. To a solution 5-chloro-1-(phenylsulfonyl)-1H-indol-2-yl)(1-(phenylsulfonyl)-1H-indol-5-yl)methanone (281 mg, 0.489 mmol) in 10 mL of THF, was added 2.5 mL of TBAF solution in THF (1 M). The reaction mixture was heated to reflux overnight, cooled to RT, diluted with EtOAc, washed with brine (×2), dried (MgSO$_4$), and concentrated. Chromatography over 10 g SiO$_2$ (60% EtOAc/Hexanes) gave (1H-indol-6-yl)(5-methoxy-1H-indol-2-yl)methanone (101 mg, 0.343 mmol, 70%) as an orange solid. $^1$H NMR (399 MHz, DMSO-d$_6$) δ ppm 12.06 (1H, s), 11.51 (1H, br. s.), 8.24-8.31 (1H, m), 7.78 (1H, d, J=2.0 Hz), 7.73 (1H, dd, J=8.6, 2.0 Hz), 7.55 (1H, d, J=8.6 Hz), 7.46-7.52 (2H, m), 7.28 (1H, dd, J=8.6, 2.0 Hz), 7.10-7.14 (1H, m), 6.64 (1H, t, J=2.0 Hz); MS (ESI) m/z Calculated 294.06 Found 295.04 (M+H)+.

Example 17

(1H-indazol-5-yl)(5-methoxy-1H-indol-2-yl)methanone

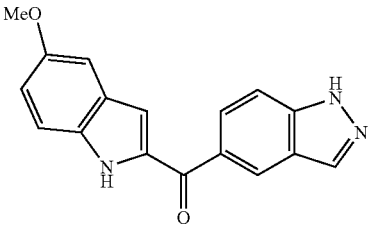 [SMILES: COc1ccc2[nH]c(C(=O)c3ccc4[nH]ncc4c3)cc2c1]

1. To a solution of 1H-indazole-5-carbaldehyde (500 mg, 3.42 mmol) in 23 mL of dichloromethane, were added phenylsulfonylchloride (0.47 mL, 3.66 mmol), diisopropylethylamine (3.0 mL, 17.1 mmol), and DMAP (42 mg, 0.34 mmol). The reaction mixture was stirred at RT for 18 hr, diluted with dichloromethane, washed with saturated ammonium chloride, dried (MgSO$_4$), and concentrated. The residue was purified over 50 g SiO$_2$ (60% EtOAc/Hexanes) to give 1-(phenylsulfonyl)-1H-indazole-5-carbaldehyde (0.815 g, 2.85 mmol, 83%) as a white solid. $^1$H NMR (399 MHz, CHLOROFORM-d) δ ppm 10.07 (1H, s), 8.87 (1H, d, J=0.8 Hz), 8.28-8.48 (1H, m), 8.18-8.25 (1H, m), 8.08-8.18 (1H, m), 7.95-8.06 (1H, m), 7.63-7.74 (1H, m), 7.53-7.63 (1H, m), 7.42-7.53 (1H, m)

2. To a solution of 5-methoxy-1-(phenylsulfonyl)-1H-indole (288 mg, 1.00 mmol) in 4 mL of THF, was added 0.48 mL of n-BuLi solution in hexanes (2.5 M) at −78° C. After 1 hr, a solution of 1-(phenylsulfonyl)-1H-indazole-5-carbaldehyde (315 mg, 1.10 mmol) in 2 mL of THF was added slowly. After 2 hr, the reaction mixture was allowed to warm up to RT slowly, quenched with saturated ammonium chloride solution, and extracted with EtOAc. The organic layer was dried (MgSO$_4$), and concentrated. Chromatography over 10 g SiO$_2$ (80% EtOAc/Hexanes) gave (5-methoxy-1-(phenylsulfonyl)-1H-indol-2-yl)(1-(phenylsulfonyl)-1H-indazol-5-yl)methanol (150 mg, 0.261 mmol, 26%) as a brownish oil. $^1$H NMR (399 MHz, CHLOROFORM-d) δ ppm 8.05-8.20 (2H, m), 7.89-8.05 (3H, m), 7.75 (1H, s), 7.40-7.70 (7H, m), 7.26-7.35 (2H, m), 6.90 (1H, dd, J=9.2, 2.5 Hz), 6.81 (1H, d, J=2.3 Hz), 6.43 (1H, s), 6.11 (1H, s), 3.75 (3H, s)

3. The mixture of (5-methoxy-1-(phenylsulfonyl)-1H-indol-2-yl)(1-(phenylsulfonyl)-1H-indazol-5-yl)methanol and MnO$_2$ (454 mg, 5.22 mmol) in 5 mL of dichloromethane was stirred overnight at RT, diluted with dichloromethane, filtered through a pad of Celite, and concentrated to give (5-methoxy-1-(phenylsulfonyl)-1H-indol-2-yl)(1-(phenylsulfonyl)-1H-indazol-5-yl)methanone (149 mg, quant.) as an off white solid. $^1$H NMR (399 MHz, CHLOROFORM-d) δ ppm 8.15-8.35 (4H, m), 7.97-8.06 (3H, m), 7.86-7.97 (3H, m), 7.40-7.64 (7H, m), 7.07 (1H, dd, J=9.2, 2.5 Hz), 6.96 (1H, d, J=2.7 Hz), 6.89 (1H, s), 3.81 (3H, s)

4. To a solution (5-methoxy-1-(phenylsulfonyl)-1H-indol-2-yl)(1-(phenylsulfonyl)-1H-indazol-5-yl)methanone in 5 mL of THF, was added 1.3 mL of TBAF solution in THF (1 M). The reaction mixture was heated to reflux overnight, cooled to RT, diluted with EtOAc, washed with brine (×2), dried (MgSO$_4$), and concentrated. Chromatography over 25 g SiO$_2$ (80% EtOAc/Hexanes) gave (1H-indazol-5-yl)(5-methoxy-1H-indol-2-yl)methanone (46 mg, 0.158 mmol, 61%) as a yellow solid. $^1$H NMR (399 MHz, DMSO-d$_6$) δ ppm 13.41 (1H, s), 11.80 (1H, s), 8.48 (1H, s), 8.29 (1H, s), 7.90 (1H, dd, J=8.8, 1.4 Hz), 7.68 (1H, d, J=8.8 Hz), 7.39 (1H, d, J=9.0 Hz), 7.15 (1H, d, J=2.7 Hz), 7.08 (1H, d, J=1.6 Hz), 6.96 (1H, dd, J=9.0, 2.3 Hz), 3.75 (3H, s); MS (ESI) m/z Calculated 291.10 Found 292.29 (M+H)+.

Example 18

(5-methoxy-1H-indol-2-yl)(3-methyl-1H-indazol-5-yl)methanone

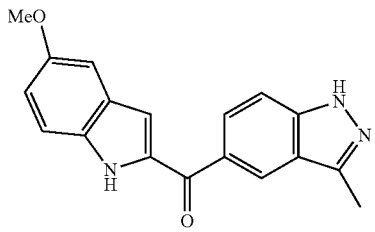

1. To a solution of 5-methoxy-1-(phenylsulfonyl)-1H-indole (8 g, 27.85 mmol) in 140 mL of THF, was added 17.6 mL (28.13 mmol) of n-BuLi solution in hexanes (1.6 M) at −78° C. After 1 hr at −78° C., the reaction mixture was added DMF (10 mL). After 2 hr at RT, the reaction was quenched with saturated sodium bicarbonate, and extracted with EtOAc (×3). The combined organic extracts were dried (MgSO$_4$), filtered, and concentrated. Flash chromatography (20% EtOAc/Hexanes) gave 5-methoxy-1-(phenylsulfonyl)-1H-indole-2-carbaldehyde (6.8 g, 78%). $^1$H NMR (400 MHz, CDCl$_3$) δ ppm: 10.49 (s, 1H), 8.12 (d, J=9.2 Hz, 1H), 7.73 (d, J=8.8 Hz, 2H), 7.52 (t, J=7.2 Hz, 1H), 7.38 (t, J=7.6, Hz, 3H), 7.14 (dd, J=9.2, 2.4 Hz, 1H), 6.97 (d, J=2.4 Hz, 1H), 3.81 (s, 3H).

2. To a solution of 5-bromo-3-methyl-1H-indazole (2 g, 9.47 mmol) in 60 mL of THF, was added 5.92 mL of n-BuLi solution in hexanes (1.6 M) at −78° C. After 10 min, 16.72 mL of t-BuLi solution in pentane (1.7 M) was added. After 1 hr at −78° C., a solution of 5-methoxy-1-(phenylsulfonyl)-1H-indole-2-carbaldehyde (5.9 g, 35 mmol) in 35 mL of THF was added slowly. After 2 hr at −78° C., the reaction mixture was allowed to warm up to −30° C. slowly, and stirred for another 1 hr. The reaction mixture was quenched with saturated sodium bicarbonate, and extracted with EtOAc (×3). The combined organic extracts were dried (MgSO$_4$), filtered, and concentrated. Flash chromatography (EtOAc/Hexanes) gave (5-methoxy-1-(phenylsulfonyl)-1H-indol-2-yl)(3-methyl-1H-indazol-5-yl)methanol (3.1 g, 73%). $^1$H NMR (400 MHz, DMSO-d$_6$) δ ppm: 12.56 (s, 1H), 7.83 (d, J=9.2 Hz, 1H), 7.67 (d, J=7.6 Hz, 2H), 7.57-7.52 (m, 2H), 7.41-7.33 (m, 3H), 7.27 (dd, J=8.8, 1.6 Hz, 1H), 7.03 (d, J=2.8 Hz, 1H), 6.85 (dd, J=9.2, 2.8 Hz, 1H), 6.57 (s, 1H), 6.43 (d, J=5.6 Hz, 1H), 6.11 (d, J=5.6 Hz, 1H), 3.68 (s, 3H), 2.38 (s, 3H).

3. The mixture of (5-methoxy-1-(phenylsulfonyl)-1H-indol-2-yl)(3-methyl-1H-indazol-5-yl)methanol (1.7 g, 3.8 mmol) and MnO$_2$ (9.3 g, 107 mmol) in 120 mL of THF and 80 mL dichloromethane was stirred overnight at RT. The reaction mixture was filtered through a pad of Celite, and concentrated to give crude (5-methoxy-1-(phenylsulfonyl)-1H-indol-2-yl)(3-methyl-1H-indazol-5-yl)methanone.

To a crude (5-methoxy-1-(phenylsulfonyl)-1H-indol-2-yl)(3-methyl-1H-indazol-5-yl)methanone was added 35 mL of TBAF solution in THF (1 M). The reaction mixture was stirred at 60° C. for overnight. After cooled to RT, the reaction mixture was poured into water, and extracted with EtOAc (×3). The combined organic extracts were washed with water (×2), dried (MgSO$_4$), filtered, and concentrated. Flash chromatography (EtOAc/Hexanes) gave (5-methoxy-1H-indol-2-yl)(3-methyl-1H-indazol-5-yl)methanone (892 mg, 77% for two step). $^1$H NMR (400 MHz, DMSO-d$_6$) δ ppm: 12.99 (s, 1H), 11.78 (s, 1H), 8.36 (s, 1H), 7.90 (dd, J=8.8, 1.2 Hz, 1H), 7.60 (d, J=8.8 Hz, 1H), 7.40 (d, J=8.8 Hz, 1H), 7.16 (d, J=2.4 Hz, 1H), 7.09 (d, J=1.6 Hz, 1H), 6.96 (dd, J=9.2, 2.8 Hz, 1H), 3.75 (s, 3H), 2.55 (s, 3H). MS: 306.23 (M+H+).

Example 19

(3-ethyl-1H-indazol-5-yl)(5-methoxy-1H-indol-2-yl)methanone

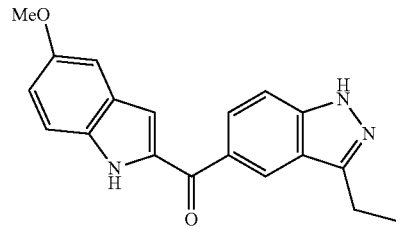 [SMILES: CCc1n[nH]c2ccc(C(=O)c3cc4cc(OC)ccc4[nH]3)cc12]

1. 1-(5-bromo-2-fluorophenyl)propan-1-ol (2.43 g, 10.4 mmol), which was prepared by known procedure (WO2009144554), was dissolved in 250 mL of DCM. To this solution was added PCC (4.48 g, 20.8 mmol). The reaction mixture was stirred overnight at RT, diluted with DCM, and filtered through a pad of SiO$_2$. The filtrate was concentrated to give crude 1-(5-bromo-2-fluorophenyl)propan-1-one (2.20 g, 9.52 mmol, 92%) as an oil. $^1$H NMR (399 MHz, CHLOROFORM-d) δ ppm 7.97 (1H, dd, J=6.5, 2.7 Hz), 7.59 (1H, ddd, J=8.6, 4.3, 2.7 Hz), 7.03 (1H, dd, J=10.4, 8.8 Hz), 2.98 (2H, d, J=7.2 Hz), 1.20 (3H, t, J=7.2 Hz)

2. The mixture of 1-(5-bromo-2-fluorophenyl)propan-1-one (2.20 g, 9.52 mmol) and 20 mL of hydrazine monohydrate was heated to reflux overnight, cooled to RT, and concentrated to the dryness. The residue was diluted with EtOAc, and washed with water and brine, dried (MgSO$_4$), and concentrated to give crude 5-bromo-3-ethyl-1H-indazole (2.14 g, 9.52 mmol, 100%) as a sticky solid. $^1$H NMR (399 MHz, CHLOROFORM-d) δ ppm 7.86 (1H, d, J=1.6 Hz), 7.44 (1H, dd, J=8.6, 1.6 Hz), 7.32 (1H, d, J=8.6 Hz), 2.98 (2H, d, J=7.4 Hz), 1.41 (3H, t, J=7.4 Hz)

3. To a solution of 5-bromo-3-ethyl-1H-indazole (256 mg, 1.14 mmol) in 11 mL of THF, was added 0.71 mL of n-BuLi solution in hexane (1.6 M) at −78° C. After 10 minutes, 2.0 mL of t-BuLi solution in pentane (1.7 M) was added at the same temperature. After 1 hr, a solution of 5-methoxy-1-(phenylsulfonyl)-1H-indole-2-carbaldehyde (717 mg, 2.27 mmol) in 5 mL of THF was added slowly. After 1 hr, the reaction mixture was stirred at −40° C. for 1 hour, then quenched with saturated sodium bicarbonate solution, and extracted with EtOAc. The organic layer was washed with water and brine, dried (MgSO$_4$), and concentrated. Chromatography over 50 g SiO$_2$ (80% EtOAc/Hexanes) gave (3-ethyl-1H-indazol-5-yl)(5-methoxy-1-(phenylsulfonyl)-1H-indol-2-yl)methanol (142 mg, 0.308 mmol, 27%) as an oil. $^1$H NMR (399 MHz, CHLOROFORM-d) δ ppm 8.00 (1H, d, J=9.4 Hz), 7.80 (1H, br. s.), 7.71 (2H, d, J=7.8 Hz), 7.50 (1H, d, J=7.0 Hz), 7.28-7.44 (4H, m), 6.92 (1H, br. s.), 6.82 (1H, br. s.), 6.47 (1H, br. s.), 6.14 (1H, s), 3.77 (3H, s), 2.99 (2H, d, J=7.4 Hz), 1.61 (3H, t, d, J=7.4 Hz)

4. The mixture of (3-ethyl-1H-indazol-5-yl)(5-methoxy-1-(phenylsulfonyl)-1H-indol-2-yl)methanol and MnO$_2$ (1.07 g, 12.3 mmol) in 25 mL of dichloromethane was stirred overnight at RT, diluted with EtOAc, filtered through a pad of Celite, and concentrated to give (3-ethyl-1H-indazol-5-yl)(5-methoxy-1-(phenylsulfonyl)-1H-indol-2-yl) methanone (63 mg, 0.137 mmol, 45%) as a yellow solid. $^1$H NMR (399 MHz, CHLOROFORM-d) δ ppm 8.38 (1H, s), 7.97-8.11 (3H, m), 7.56 (1H, d, J=7.4 Hz), 7.41-7.53 (4H, m), 7.08 (1H, dd, J=9.0, 2.7 Hz), 7.00 (1H, d, J=2.7 Hz), 6.89 (1H, s), 3.84 (3H, s), 3.02 (2H, q, J=7.7 Hz), 1.35-1.45 (3H, t, d, J=7.7 Hz)

5. To a solution of (3-ethyl-1H-indazol-5-yl)(5-methoxy-1-(phenylsulfonyl)-1H-indol-2-yl)methanone in 5 mL of THF, was added 1.4 mL of TBAF solution in THF (1 M). The reaction mixture was stirred at 50° C. overnight, cooled to RT, diluted with EtOAc, washed with brine (×2), dried (MgSO$_4$), and concentrated. Chromatography over 10 g SiO$_2$ (80% EtOAc/Hexanes) gave (3-ethyl-1H-indazol-5-yl)(5-methoxy-1H-indol-2-yl)methanone (31 mg, 0.097 mmol, 71%) as a yellow solid. $^1$H NMR (399 MHz, DMSO-d$_6$) δ ppm 12.99 (1H, s), 11.79 (1H, s), 8.39 (1H, s), 7.90 (1H, dd, J=8.8, 1.4 Hz), 7.60 (1H, d, J=9.0 Hz), 7.39 (1H, d, J=8.6 Hz), 7.16 (1H, d, J=2.0 Hz), 7.07 (1H, d, J=2.0 Hz), 6.95 (1H, dd, J=9.0, 2.7 Hz), 3.76 (3H, s), 3.00 (2H, q, J=7.6 Hz), 1.34 (2H, t, J=7.6 Hz)

Example 20

(3-chloro-1H-indazol-5-yl)(5-methoxy-1H-indol-2-yl)methanone

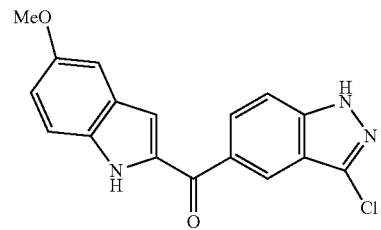 [SMILES: COc1ccc2[nH]c(C(=O)c3ccc4[nH]nc(Cl)c4c3)cc2c1]

1. 3-chloro-1H-indazole-5-carbaldehyde was prepared by following reported procedure (WO 2009149837). To a solution of 3-chloro-1H-indazole-5-carbaldehyde (0.660 g, 3.65 mmol) in 50 mL of dichloromethane, were added phenylsulfonylchloride (2.6 mL, 18 mmol), triethylamine (2.6 mL, 18.3 mmol), and DMAP (45 mg, 0.37 mmol). The reaction mixture was stirred at RT for 18 hr, concentrated, diluted with EtOAc, washed with saturated solution of ammonium chloride and brine, dried (MgSO$_4$), and concentrated. The residue was purified over 50 g SiO$_2$ (40% EtOAc/Hexanes) to give 3-chloro-1-(phenylsulfonyl)-1H-indazole-5-carbaldehyde (0.810 g, 2.53 mmol, 69%) as an off white solid. $^1$H NMR (300 MHz, CHLOROFORM-d) δ ppm 8.15 (1H, d, J=8.5 Hz), 7.92-8.06 (3H, m), 7.55-7.76 (5H, m), 7.45-7.55 (3H, m), 7.30-7.41 (2H, m), 6.93 (1H, dd, J=9.1, 2.6 Hz), 6.83 (1H, d, J=2.6 Hz), 6.46 (1H, d, J=4.7 Hz), 6.10 (1H, s), 3.70-3.83 (3H, m)

2. To a solution of 5-methoxy-1-(phenylsulfonyl)-1H-indole (287 mg, 1.00 mmol) in 5 mL of THF, was added 0.75 mL of n-BuLi solution in pentane (1.6 M) at −78° C. After 1 hr, a solution of 3-chloro-1-(phenylsulfonyl)-1H-indazole-5-carbaldehyde (353 mg, 1.10 mmol) in 5 mL of THF was added slowly. After 1 hr, the reaction mixture was allowed to warm up to RT slowly, quenched with saturated ammonium chloride solution, and extracted with EtOAc. The organic layer was washed with brine, dried (MgSO$_4$), and concentrated. Chromatography over 25 g SiO$_2$ (80% EtOAc/Hexanes) gave (3-chloro-1-(phenylsulfonyl)-1H-indazol-5-yl)(5-methoxy-1-(phenylsulfonyl)-1H-indol-2-yl)methanol (449 mg, 0.738 mmol, 74%) as a sticky solid, which was dissolved in 10 mL of dichloromethane and 40 mL of THF, and reacted with MnO$_2$ (1.28 g, 14.8 mmol) overnight at RT. The reaction mixture was diluted with dichloromethane and THF, filtered through a pad of Celite, and concentrated to give crude product. $^1$H NMR (300 MHz, CHLOROFORM-d) δ ppm 8.16-8.36 (3H, m), 7.87-8.09 (5H, m), 7.38-7.75 (6H, m), 7.10 (1H, dd, J=9.2, 2.5 Hz), 6.83-7.02 (2H, m), 3.80 (3H, s)

3. To a solution of crude (3-chloro-1-(phenylsulfonyl)-1H-indazol-5-yl)(5-methoxy-1-(phenylsulfonyl)-1H-indol-2-yl)methanone (367 mg, 0.606 mmol) in 6 mL of THF, was added 6.0 mL of TBAF solution in THF (1 M). The reaction mixture was heated to reflux overnight, cooled to RT, diluted with EtOAc, washed with brine (×2), dried (MgSO$_4$), and concentrated. Chromatography over 25 g SiO$_2$ (80% EtOAc/ hexanes) gave (3-chloro-1H-indazol-5-yl)(5-methoxy-1H-indol-2-yl)methanone (105 mg, 0.322 mmol, 53%) as a yellow solid. ¹H NMR (399 MHz, DMSO-d₆) δ ppm 13.65 (1H, s), 11.85 (1H, s), 8.24 (1H, s), 7.99 (1H, dd, J=8.7, 1.2 Hz), 7.73 (1H, d, J=8.7 Hz), 7.40 (1H, d, J=9.0 Hz), 7.18 (1H, d, J=2.7 Hz), 7.08-7.10 (1H, m), 6.97 (1H, dd, J=9.0, 2.7 Hz), 3.76 (3H, s); MS (ESI) m/z Calculated 325.06 Found 326.15 (M+H)+.

Example 21

(3-fluoro-1H-indazol-5-yl)(5-methoxy-1H-indol-2-yl)methanone

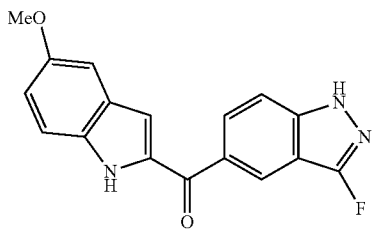

1. The mixture of 1H-indazole-5-carbaldehyde (146 mg, 1.00 mmol) and Selectfluor (709 mg, 2.00 mmol) in 4 mL of acetonitrile was stirred at 90° C. for 6 hr, cooled to RT, concentrated, diluted with dichloromethane, filtered, and washed with dichloromethane. The filtrate was concentrated to give crude 3-fluoro-1H-indazole-5-carbaldehyde (107 mg, 0.652 mmol, 65%) as a bright brownish solid. ¹H NMR (399 MHz, DMSO-d₆) δ ppm 13.04 (1H, br. s.), 10.02 (1H, s), 8.39 (1H, s), 7.87 (1H, dd, J=8.8, 1.4 Hz), 7.60 (1H, dd, J=9.0, 2.3 Hz)

2. To a solution of 3-fluoro-1H-indazole-5-carbaldehyde in 6 mL of THF and 6 mL of dichloromethane, were added phenylsulfonylchloride (0.092 mL, 0.717 mmol), triethylamine (0.45 mL, 3.26 mmol), and DMAP (8 mg, 0.065 mmol). The reaction mixture was stirred at RT for 18 hr, concentrated, diluted with EtOAc, washed with saturated solution of ammonium chloride and brine, dried (MgSO₄), and concentrated. The residue was purified over 10 g SiO₂ (50% EtOAc/Hexanes) to give 3-fluoro-1-(phenylsulfonyl)-1H-indazole-5-carbaldehyde (128 mg, 0.421 mmol, 65%) as an off white solid. ¹H NMR (399 MHz, CHLOROFORM-d) δ ppm 10.07 (1H, s), 8.32 (1H, dd, J=9.4, 2.0 Hz), 8.15-8.18 (2H, m), 7.93-8.02 (2H, m), 7.59-7.67 (1H, m), 7.44-7.53 (2H, m)

3. To a solution of 5-methoxy-1-(phenylsulfonyl)-1H-indole (112 mg, 0.389 mmol) in 4 mL of THF, was added 0.29 mL of n-BuLi solution in hexanes (1.6 M) at −78° C. After 1 hr, a solution of 3-fluoro-1-(phenylsulfonyl)-1H-indazole-5-carbaldehyde (128 mg, 0.421 mmol) in 3 mL of THF was added slowly. After 1 hr, the reaction mixture was allowed to warm up to RT slowly, quenched with saturated ammonium chloride solution, and extracted with EtOAc. The organic layer was washed with brine, dried (MgSO₄), and concentrated. Chromatography over 10 g SiO₂ (60% EtOAc/Hexanes) gave (3-fluoro-1-(phenylsulfonyl)-1H-indazol-5-yl)(5-methoxy-1-(phenylsulfonyl)-1H-indol-2-yl) methanol (89 mg, 0.15 mmol, 39%) as an oil, which was dissolved in 3 mL of dichloromethane, and reacted with MnO₂ (261 mg, 3.00 mmol) overnight at RT. The reaction mixture was diluted with dichloromethane, filtered through a pad of Celite, and concentrated to give crude (3-fluoro-1-(phenylsulfonyl)-1H-indazol-5-yl)(5-methoxy-1-(phenylsulfonyl)-1H-indol-2-yl)methanone (76 mg, 0.13 mmol, 86%). ¹H NMR (399 MHz, CHLOROFORM-d) δ ppm 8.28 (1H, d, J=1.2 Hz), 8.07-8.25 (1H, m), 7.95-8.07 (3H, m), 7.77-7.95 (2H, m), 7.41-7.65 (4H, m), 7.37 (1H, dd, J=8.4, 1.0 Hz), 7.03-7.18 (2H, m), 6.94-7.03 (1H, m), 6.91 (1H, s), 6.81 (1H, d, J=2.7 Hz), 3.72-3.88 (3H, s)

4. To a solution of crude (3-fluoro-1-(phenylsulfonyl)-1H-indazol-5-yl)(5-methoxy-1-(phenylsulfonyl)-1H-indol-2-yl)methanone in 4 mL of THF, was added 1.3 mL of TBAF solution in THF (1 M). The reaction mixture was heated to reflux overnight, cooled to RT, diluted with EtOAc, washed with brine (×2), dried (MgSO₄), and concentrated. Chromatography over 10 g SiO₂ (80% EtOAc/hexanes) gave (3-fluoro-1H-indazol-5-yl)(5-methoxy-1H-indol-2-yl)methanone (22 mg, 0.071 mmol, 55%) as a yellow solid. ¹H NMR (399 MHz, DMSO-d₆) δ ppm 12.93 (1H, br. s.), 11.81 (1H, br. s.), 8.31 (1H, s), 7.94 (1H, m, J=9.0 Hz), 7.63 (1H, m, J=9.0 Hz), 7.38 (1H, d, J=9.0 Hz), 7.14 (1H, d, J=2.3 Hz), 7.09 (1H, d, J=1.6 Hz), 6.95 (1H, dd, J=9.0, 2.3 Hz), 3.74 (2H, s); MS (ESI) m/z Calculated 309.09 Found 310.27 (M+H)+.

Example 22

(5-methoxy-1H-indol-2-yl)(3-(morpholinomethyl)-1H-indazol-5-yl)methanone

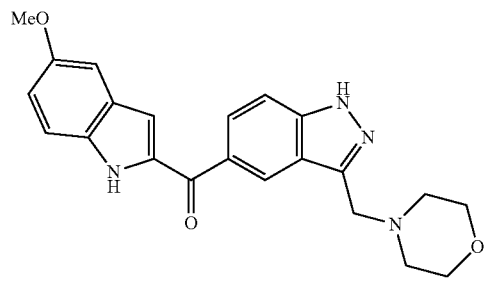 [SMILES: COc1ccc2[nH]c(C(=O)c3ccc4[nH]nc(CN5CCOCC5)c4c3)cc2c1]

To a solution of (5-methoxy-1-(phenylsulfonyl)-1H-indol-2-yl)(3-(morpholinomethyl)-1H-indazol-5-yl)methanone (29 mg, 0.055 mmol) in 3 mL of THF, was added 1.1 mL of TBAF solution in THF (1 M). The reaction mixture was stirred at 50° C. overnight, cooled to RT, diluted with EtOAc, washed with brine (×2), dried (MgSO₄), and concentrated. Chromatography over 10 g SiO₂ (80% EtOAc/Hexanes) gave (5-methoxy-1H-indol-2-yl)(3-(morpholinomethyl)-1H-indazol-5-yl)methanone (11 mg, 0.028 mmol, 51%) as a yellow solid. ¹H NMR (399 MHz, CHLOROFORM-d) δ ppm 9.21 (2H, brs), 8.70 (1H, s), 8.07 (1H, d, J=8.2 Hz), 7.57 (1H, d, J=9.0 Hz), 7.41 (1H, d, J=8.6 Hz), 7.03-7.16 (3H, m), 3.99 (2H, br. s.), 3.87 (3H, s), 3.77 (4H, br. s.), 2.59 (4H, br. s.)

Example 23

(3-chloro-5-methoxy-1H-indol-2-yl)(1H-indazol-5-yl)methanone

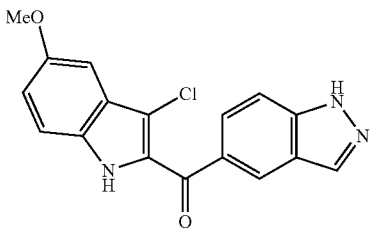 [SMILES: COc1ccc2[nH]c(C(=O)c3ccc4[nH]ncc4c3)c(Cl)c2c1]

To a solution of (1H-indazol-5-yl)(5-methoxy-1H-indol-2-yl)methanone (23 mg, 0.079 mmol) in 2 mL of DMF, were added N-Chlorosuccinimide (11 mg, 0.083 mmol). The reaction mixture was stirred at RT for 18 hr, and partitioned between EtOAc and brine. The organic layer was washed with brine (×2), dried (MgSO$_4$), and concentrated. Chromatography over 10 g SiO$_2$ (80% EtOAc/Hexanes) gave an impure (3-chloro-5-methoxy-1H-indol-2-yl)(1H-indazol-5-yl)methanone (22 mg, 0.068 mmol, 85%) as an off white solid. $^1$H NMR (399 MHz, DMSO-d$_6$) δ ppm 13.38-13.52 (1H, m), 12.01 (1H, s), 11.80 (1H, br. s.), 8.46-8.53 (1H, m), 8.20-8.37 (2H, m), 7.90 (1H, d, J=7.4 Hz), 7.75-7.86 (1H, m), 7.65-7.75 (1H, m), 7.36-7.42 (1H, m), 7.15 (1H, d, J=2.7 Hz), 6.89-7.04 (2H, m), 3.81 (2H, s), 3.75 (1H, s; MS (ESI) m/z Calculated 325.06 Found 326.21 (M+H)+.

Example 24

(4-chloro-5-methoxy-1H-indol-2-yl)(1H-indazol-5-yl)methanone

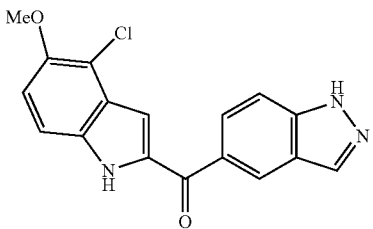 [SMILES: COc1ccc2[nH]c(C(=O)c3ccc4[nH]ncc4c3)cc2c1Cl]

1. To a solution of 5-methoxy-1-(phenylsulfonyl)-1H-indole-2-carbaldehyde (276 mg, 0.876 mmol) in 9 mL of DMF, was added N-Chlorosuccinimide (140 mg, 1.05 mmol). The reaction mixture was stirred at 80° C. for 2 hr, cooled to RT, diluted with EtOAc, washed with 1N NaOH solution and brine, dried (MgSO$_4$), and concentrated. Chromatography over 25 g SiO$_2$ (30% EtOAc/Hexanes) gave 4-chloro-5-methoxy-1-(phenylsulfonyl)-1H-indole-2-carbaldehyde (250 mg, 0.715 mmol, 82%) as an off white solid. $^1$H NMR (300 MHz, CHLOROFORM-d) δ ppm 8.05 (1H, s), 7.98 (1H, d, J=8.8 Hz), 7.81 (1H, s), 7.66 (2H, d, J=7.6 Hz), 7.47 (2H, m), 7.42 (2H, m), 7.30-7.38 (2H, m), 6.96 (1H, d, J=8.5 Hz), 6.50 (1H, s), 6.39 (1H, s), 3.88 (3H, s)

2. To a solution of 5-bromo-1H-indazole (77 mg, 0.39 mmol) in 4 mL of THF, was added 0.76 mL of t-BuLi solution in pentane (1.7 M) at −78° C. After 2 hr, a solution of 4-chloro-5-methoxy-1-(phenylsulfonyl)-1H-indole-2-carbaldehyde (150 mg, 0.429 mmol) in 2 mL of THF was added slowly. After 1 hr, the reaction mixture was allowed to warm up to RT slowly, quenched with saturated ammonium chloride solution, and extracted with EtOAc. The organic layer was washed with brine, dried (MgSO$_4$), and concentrated. Chromatography over 10 g SiO$_2$ (80% EtOAc/Hexanes) gave (4-chloro-5-methoxy-1-(phenylsulfonyl)-1H-indol-2-yl)(1H-indazol-5-yl)methanol (109 mg, 0.233 mmol, 60%) as an off white solid, which was dissolved in 10 mL of dichloromethane, and reacted with MnO$_2$ (405 mg, 4.66 mmol) overnight at RT. The reaction mixture was diluted with dichloromethane and THF, filtered through a pad of Celite, and concentrated to give crude product. $^1$H NMR (300 MHz, CHLOROFORM-d) δ ppm 8.38 (1H, s), 8.20 (1H, s), 8.14 (1H, dd, J=8.9, 1.6 Hz), 7.96-8.07 (3H, m), 7.59 (2H, dd, J=8.2, 4.4 Hz), 7.41-7.54 (2H, m), 7.13 (1H, d, J=9.1 Hz), 7.02 (1H, d, J=0.6 Hz), 3.88 (3H, s)

3. To a solution of crude (4-chloro-5-methoxy-1-(phenylsulfonyl)-1H-indol-2-yl)(1H-indazol-5-yl)methanone (79 mg, 0.17 mmol) in 5 mL of THF, was added 0.85 mL of TBAF solution in THF (1 M). The reaction mixture was heated to reflux overnight, cooled to RT, diluted with EtOAc, washed with brine (×2), dried (MgSO$_4$), and concentrated. Chromatography over 10 g SiO$_2$ (80% EtOAc/hexanes) gave (4-chloro-5-methoxy-1H-indol-2-yl)(1H-indazol-5-yl)methanone (48 mg, 0.15 mmol, 87%) as a yellow solid. $^1$H NMR (399 MHz, DMSO-d$_6$) δ ppm 13.42 (1H, s), 12.12 (1H, s), 8.52 (1H, s), 8.33 (1H, s), 7.92 (1H, dd, J=8.4, 1.5 Hz), 7.71 (1H, d, J=9.0 Hz), 7.45 (1H, d, J=9.0 Hz), 7.28 (1H, d, J=9.0 Hz), 7.00-7.03 (1H, m), 3.87 (3H, s); MS (ESI) m/z Calculated 325.06 Found 326.21 (M+H)+.

Example 25

(3,4-dichloro-5-methoxy-1H-indol-2-yl)(1H-indazol-5-yl)methanone

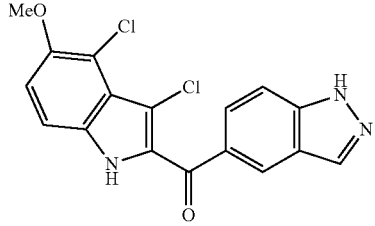 [SMILES: COc1ccc2[nH]c(C(=O)c3ccc4[nH]ncc4c3)c(Cl)c2c1Cl]

To a solution of (1H-indazol-5-yl)(5-methoxy-1H-indol-2-yl)methanone (29 mg, 0.10 mmol) in 2 mL of DMF, were added N-Chlorosuccinimide (28 mg, 0.21 mmol). The reaction mixture was stirred at RT for 18 hr, and partitioned between EtOAc and brine. The organic layer was dried (MgSO$_4$), and concentrated. Chromatography over 10 g SiO$_2$ (80% EtOAc/Hexanes) gave (3,4-dichloro-5-methoxy-1H-indol-2-yl)(1H-indazol-5-yl)methanone (18 mg, 0.050 mmol, 50%) as an off white solid. $^1$H NMR (399 MHz, DMSO-d$_6$) δ ppm 13.46 (1H, s), 12.28 (1H, s), 8.34 (1H, s), 8.29 (1H, s), 7.84 (1H, dd, J=8.8, 1.4 Hz), 7.68 (1H, d, J=9.0 Hz), 7.44 (1H, d, J=9.0 Hz), 7.30 (1H, d, J=9.0 Hz), 3.87 (3H, s); MS (ESI) m/z Calculated 359.02 Found 360.25 (M+H)+.

Example 26

(5-fluoro-1H-indol-2-yl)(3-methyl-1H-indazol-5-yl)methanone

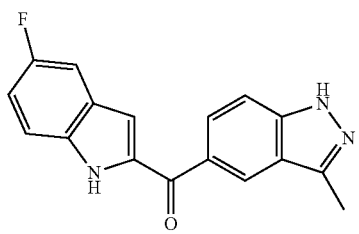 [SMILES: Cc1n[nH]c2ccc(C(=O)c3cc4cc(F)ccc4[nH]3)cc12]

1. To solution of 5-fluoro-1H-indole (600 mg, 4.44 mmol) in 20 mL of THF, was added sodium hydride (60 wt % dispersion, 267 mg, 6.67 mmol) at 0° C. After 1 hr RT, phenylsulfonylchloride (0.852 mL, 6.67 mmol) was added. After 2 hr at RT, the reaction was quenched with saturated sodium bicarbonate solution at 0° C., and extracted with EtOAc (×3). The combined organic extracts were dried (MgSO$_4$), filtered, and concentrated. The residue was trituration from MeOH to give 5-fluoro-1-(phenylsulfonyl)-1H-indole (1.21 g, quant.). $^1$H NMR (400 MHz, CDCl$_3$) δ ppm: 7.92 (dd, J=8.8, 4.4 Hz, 1H), 7.84 (d, J=7.2 Hz, 2H), 7.58 (d, J=3.6 Hz, 1H), 7.53 (t, J=7.6 Hz, 1H), 7.43 (t, J=7.6 Hz, 2H), 7.16 (dd, J=8.8, 2.4 Hz, 1H), 7.02 (td, J=9.2, 2.4 Hz, 1H), 6.61 (d, J=3.2 Hz, 1H).

2. To a solution of 5-fluoro-1-(phenylsulfonyl)-1H-indole (1.21 g, 4.4 mmol) in 17 mL of THF, was added 3.02 mL (4.8 mmol) of n-BuLi solution in hexanes (1.6 M) at −78° C. After 1 hr at −78° C., the reaction mixture was added DMF (10 mL). After 2.5 hr at RT, the reaction was quenched with saturated sodium bicarbonate, and extracted with EtOAc (×3). The combined organic extracts were dried (MgSO$_4$), filtered, and concentrated. Flash chromatography (15% EtOAc/Hexanes) gave 5-fluoro-1-(phenylsulfonyl)-1H-indole-2-carbaldehyde (0.71 g, 54%). $^1$H NMR (400 MHz, CDCl$_3$) δ ppm: 10.50 (s, 1H), 8.20 (q, J=4.0 Hz, 1H), 7.74 (d, J=7.6 Hz, 2H), 7.55 (t, J=7.2 Hz, 1H), 7.42 (t, J=8.0 Hz, 2H), 7.41 (s, 1H), 7.29-7.21 (m, 2H).

3. To a solution of 5-bromo-3-methyl-1H-indazole (336 mg, 1.56 mmol) in 8 mL of THF, was added 0.98 mL of n-BuLi solution in hexanes (1.6 M) at −78° C. After 10 min, 2.75 mL of t-BuLi solution in pentane (1.7 M) was added. After 1 hr at −78° C., a solution of 5-fluoro-1-(phenylsulfonyl)-1H-indole-2-carbaldehyde (710 mg, 2.34 mmol) in 5 mL of THF was added slowly. After 2 hr at −78° C., the reaction mixture was allowed to warm up to −30° C. slowly, and stirred for another 1 hr. The reaction mixture was quenched with saturated sodium bicarbonate, and extracted with EtOAc (×3). The combined organic extracts were dried (MgSO$_4$), filtered, and concentrated to give crude (5-fluoro-1-(phenylsulfonyl)-1H-indol-2-yl)(3-methyl-1H-indazol-5-yl)methanol. $^1$H NMR (400 MHz, CDCl$_3$) δ ppm: 8.05 (dd, J=10, 4.0 Hz, 1H), 7.73 (s, 1H), 7.69 (d, J=7.6 Hz, 2H), 7.50 (t, J=7.6 Hz, 1H), 7.39-7.28 (m, 4H), 7.05 (m, 2H), 6.49 (s, 1H), 6.19 (s, 1H), 2.53 (s, 3H).

The mixture of crude (5-fluoro-1-(phenylsulfonyl)-1H-indol-2-yl)(3-methyl-1H-indazol-5-yl)methanol and MnO$_2$ (4.07 g, 46.8 mmol) in 8 mL of THF and 8 mL of dichloromethane was stirred overnight at RT. The reaction mixture was filtered through a pad of Celite, and concentrated. Flash chromatograph (60% EtOAc/Hexanes) gave (5-fluoro-1-(phenylsulfonyl)-1H-indol-2-yl)(3-methyl-1H-indazol-5-yl)methanone (405.5 mg, 60% for two step). $^1$H NMR (400 MHz, CDCl$_3$) δ ppm: 9.92 (br.s, 1H), 8.30 (s, 1H), 8.11-8.02 (m, 4H), 7.58 (t, J=7.2 Hz, 1H), 7.50 (t, J=8.4 Hz, 3H), 7.21 (dd, J=7.6, 2.4 Hz, 1H), 7.18 (dd, J=8.8, 2.4 Hz, 1H), 6.87 (s, 1H), 2.58 (s, 3H).

4. To a solution of (5-fluoro-1-(phenylsulfonyl)-1H-indol-2-yl)(3-methyl-1H-indazol-5-yl)methanone (405 mg, 0.935 mmol) in 10 ml of THF, was added tetra-butylammonium fluoride trihydrate. (2.45 g, 9.35 mmol). The reaction mixture was stirred for overnight at 65° C. After cooled to RT, the reaction mixture was poured into water, and extracted with EtOAc (×3). The combined organic extracts were washed with water (×2), dried (MgSO$_4$), filtered, and concentrated. The solid was washed with little amount of dichloromethane to give (5-fluoro-1H-indol-2-yl)(3-methyl-1H-indazol-5-yl)methanone (237 mg, 86%). $^1$H NMR (400 MHz, DMSO-d$_6$) δ ppm: 12.99 (s, 1H), 12.01 (s, 1H), 8.37 (s, 1H), 7.90 (dd, J=8.4, 1.6 Hz, 1H), 7.59 (d, J=8.8 Hz, 1H), 7.51-7.43 (m, 2H), 7.18-7.12 (m, 2H), 2.54 (s, 3H). MS: 294.31 (M+H+).

Example 27

(5-(benzyloxy)-1H-indol-2-yl)(3-methyl-1H-indazol-5-yl)methanone

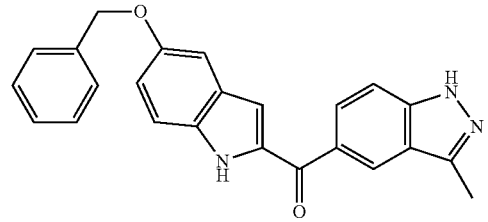 [SMILES: Cc1n[nH]c2ccc(C(=O)c3cc4cc(OCc5ccccc5)ccc4[nH]3)cc12]

1. To a cooled solution of 5-(benzyloxy)-1H-indole (2.23 g, 10.0 mmol) in 20 mL of THF, was added sodium hydride (60 wt % dispersion, 440 mg, 11.0 mmol) at 0° C. After 1 hr, phenylsulfonylchloride (1.5 mL, 12 mmol) was added. After 1 hr, the reaction was quenched with saturated ammonium chloride solution, and extracted with EtOAc. The organic layer was dried (MgSO$_4$), and concentrated. The residue was purified over 50 g SiO$_2$ (25% EtOAc/Hexanes) to give 5-(benzyloxy)-1-(phenylsulfonyl)-1H-indole (3.05 g, 8.39 mmol, 84%) as a colorless oil. $^1$H NMR (399 MHz, CHLOROFORM-d) δ ppm 7.80-7.90 (2H, m), 7.44-7.54 (2H, m), 7.26-7.44 (3H, m), 7.13-7.20 (1H, m), 6.95-7.05 (1H, m), 6.56 (1H, d, J=3.5 Hz), 5.04 (2H, s)

2. To a solution of 5-(benzyloxy)-1-(phenylsulfonyl)-1H-indole (247 mg, 0.680 mmol) in 10 mL of THF, was added 0.51 mL of n-BuLi solution in hexanes (1.6 M) at −78° C. After 1 hr, a solution of 3-methyl-1-(phenylsulfonyl)-1H-indazole-5-carbaldehyde (408 mg, 1.36 mmol) in 5 mL of THF was added slowly. After 2 hr, the reaction mixture was allowed to warm up to RT slowly, quenched with saturated sodium bicarbonate solution, and extracted with EtOAc. The organic layer was washed with brine, dried (MgSO$_4$), and concentrated. Chromatography over 25 g SiO$_2$ (60% EtOAc/Hexanes) gave (5-(benzyloxy)-1-(phenylsulfonyl)-1H-indol-2-yl)(3-methyl-1H-indazol-5-yl)methanol (200 mg, 0.301 mmol, 44%) as an brownish oil, which was dissolved in 10 mL of dichloromethane, and reacted with MnO$_2$ (1.05 g, 12.0 mmol) overnight at RT. The reaction mixture was diluted with EtOAc, filtered through a pad of Celite, and concentrated to give (5-(benzyloxy)-1-(phenylsulfonyl)-1H-indol-2-yl)(3-methyl-1H-indazol-5-yl)methanone (140 mg, 0.212 mmol, 70%) as an oil. $^1$H NMR (399 MHz, DMSO-d$_6$) δ ppm 8.36 (1H, s), 8.29 (1H, d, J=9.0 Hz), 8.20 (1H, dd, J=9.0, 1.6 Hz), 7.92-8.02 (4H, m), 7.71 (1H, d, J=7.4 Hz), 7.75 (1H, d, J=7.8 Hz), 7.56-7.67 (3H, m), 7.46 (1H, d, J=7.0 Hz), 7.39 (1H, t, J=7.2 Hz), 7.34 (1H, d, J=7.0 Hz), 7.29 (1H, d, J=2.3 Hz), 7.23 (1H, dd, J=9.2, 2.5 Hz), 5.14 (2H, s), 2.52 (3H, d, J=5.1 Hz)

3. To a solution of (5-(benzyloxy)-1-(phenylsulfonyl)-1H-indol-2-yl)(3-methyl-1H-indazol-5-yl)methanone in 10 mL of THF, was added 2.1 mL of TBAF solution in THF (1 M). The reaction mixture was stirred at 55° C. overnight, cooled to RT, diluted with EtOAc, washed with brine (×2), dried (MgSO$_4$), and concentrated. Chromatography over 10 g SiO$_2$ (80% EtOAc/Hexanes) gave (5-(benzyloxy)-1H-indol-2-yl)(3-methyl-1H-indazol-5-yl)methanone (49 mg, 0.13 mmol, 61%) as an orange solid. $^1$H NMR (399 MHz, DMSO-d$_6$) δ ppm 12.99 (1H, s), 11.81 (1H, s), 8.37 (1H, s), 7.90 (1H, dd, J=8.8, 1.4 Hz), 7.59 (1H, d, J=8.2 Hz), 7.34-7.49 (5H, m), 7.28-7.32 (1H, m), 7.25 (1H, d, J=2.3 Hz), 7.08 (1H, d, J=1.6 Hz), 7.04 (1H, dd, J=9.0, 2.3 Hz), 5.10 (2H, s), 2.55 (3H, s); MS (ESI) m/z Calculated 381.15 Found 382.29 (M+H)+.

Example 28

(7-methoxy-1H-indol-2-yl)(3-methyl-1H-indazol-5-yl)methanone

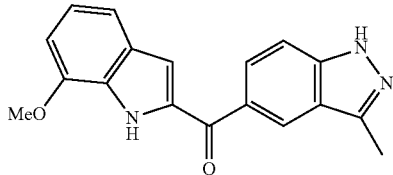 [SMILES: COc1cccc2cc(C(=O)c3ccc4[nH]nc(C)c4c3)[nH]c12]

1. To solution of 7-methoxy-1H-indole (2 g, 13.58 mmol) in 30 mL of THF, was added sodium hydride (60 wt % dispersion, 653 mg, 16.3 mmol) at 0° C. After 1.5 hr RT, phenylsulfonylchloride (2.6 mL, 20.4 mmol) was added. After overnight at RT, the reaction was quenched with saturated ammonium chloride solution at 0° C., and extracted with EtOAc (×3). The combined organic extracts were dried (MgSO$_4$), filtered, and concentrated. The residue was trituration from MeOH to give 57-methoxy-1-(phenylsulfonyl)-1H-indole (2.26 g, 58%). $^1$H NMR (400 MHz, CDCl$_3$) δ ppm: 7.84 (m, 3H), 7.55 (t, J=7.2 Hz, 1H), 7.47 (t, J=8.0 Hz, 2H), 7.18-7.10 (m, 2H), 6.68 (d, J=8.8 Hz, 1H), 6.65 (d, J=3.6 Hz, 1H), 3.64 (s, 3H).

2. To a solution of 7-methoxy-1-(phenylsulfonyl)-1H-indole (2.26 g, 7.87 mmol) in 27 mL of THF, was added 5.9 mL (9.44 mmol) of n-BuLi solution in hexanes (1.6 M) at −78° C. After 1.5 hr at −78° C., the reaction mixture was added DMF (3 mL). After 3 hr at RT, the reaction was quenched with saturated ammonium chloride solution, and extracted with EtOAc (×3). The combined organic extracts were washed with water (×2), dried (MgSO$_4$), filtered, and concentrated. Flash chromatography (30% EtOAc/Hexanes) gave 7-methoxy-1-(phenylsulfonyl)-1H-indole-2-carbaldehyde (1.85 g, 75%). $^1$H NMR (400 MHz, CDCl$_3$) δ ppm: 10.30 (s, 1H), 8.06 (d, J=7.6 Hz, 2H), 7.61 (t, J=7.2 Hz, 1H), 7.53 (t, J=7.2 Hz, 2H), 7.44 (s, 1H), 7.24 (dd, J=8.0, 1.6 Hz, 1H), 7.21 (t, J=8 Hz, 1H), 6.86 (dd, J=7.2, 1.6 Hz, 1H), 3.71 (s, 3H).

3. To a solution of 5-bromo-3-methyl-1H-indazole (500 mg, 2.37 mmol) in 15 mL of THF, was added 1.48 mL of n-BuLi solution in hexanes (1.6 M) at −78° C. After 10 min, 3.49 mL of t-BuLi solution in pentane (1.7 M) was added. After 1 hr at −78° C., a solution of 7-methoxy-1-(phenylsulfonyl)-1H-indole-2-carbaldehyde (896 mg, 2.844 mmol) in 10 mL of THF was added slowly. After 1 hr at −78° C., the reaction mixture was allowed to warm up to −30° C. slowly, and stirred for another 1 hr. The reaction mixture was quenched with saturated sodium bicarbonate solution, and extracted with EtOAc (×3). The combined organic extracts were dried (MgSO$_4$), filtered, and concentrated. Flash chromatography (EtOAc/Hexanes) gave (7-methoxy-1-(phenylsulfonyl)-1H-indol-2-yl)(3-methyl-1H-indazol-5-yl)methanol (800 mg, 75%). $^1$H NMR (400 MHz, DMSO-d$_6$) δ ppm: 12.61 (s, 1H), 7.65 (s, 1H), 7.59-7.52 (m, 3H), 7.43 (d, J=8.4 Hz, 1H), 7.35 (d, J=8.0 Hz, 1H), 7.31 (d, J=8.0 Hz, 1H), 7.29 (dd, J=8.8, 1.6 Hz, 1H), 7.11 (d, J=4.4 Hz, 2H), 6.74 (t, J=4.8 Hz, 1H), 6.57 (s, 1H), 6.54 (d, J=5.6 Hz, 1H), 6.21 (d, J=6 Hz, 1H), 3.42 (s, 3H), 2.40 (s, 3H).

4. The mixture of (7-methoxy-1-(phenylsulfonyl)-1H-indol-2-yl)(3-methyl-1H-indazol-5-yl)methanol (800 mg, 1.786 mmol) and MnO$_2$ (4.65 g, 53.5 mmol) in 20 mL of THF and 20 mL of dichloromethane was stirred overnight at RT. The reaction mixture was filtered through a pad of Celite, and concentrated to give crude (7-methoxy-1-(phenylsulfonyl)-1H-indol-2-yl)(3-methyl-1H-indazol-5-yl)methanone.

To a solution of crude (7-methoxy-1-(phenylsulfonyl)-1H-indol-2-yl)(3-methyl-1H-indazol-5-yl)methanone in 5 mL of THF, was added 8.93 mL of TBAF solution in THF (1 M). The reaction mixture was stirred for overnight at 55° C. After cooled to RT, the reaction mixture was poured into water, and extracted with EtOAc (×3). The combined organic extracts were washed with water (×2), dried (MgSO$_4$), filtered, and concentrated. Flash chromatography (65% EtOAc/Hexanes) gave (7-methoxy-1H-indol-2-yl)(3-methyl-1H-indazol-5-yl)methanone (269 mg, 49% for two step). $^1$H NMR (400 MHz, DMSO-d$_6$) δ ppm: 12.99 (s, 1H), 11.74 (s, 1H), 8.35 (s, 1H), 7.90 (dd, J=8.4, 1.6 Hz, 1H), 7.59 (d, J=8.8 Hz, 1H), 7.28 (d, J=8.4 Hz, 1H), 7.11 (d, J=2.4 Hz, 1H), 7.01 (t, J=8.0 Hz, 1H), 6.82 (d, J=7.2 Hz, 1H), 3.92 (s, 3H), 2.54 (s, 3H). MS: 306.21 (M+H+)

Example 29

(4-methoxy-1H-indol-2-yl)(3-methyl-1H-indazol-5-yl)methanone

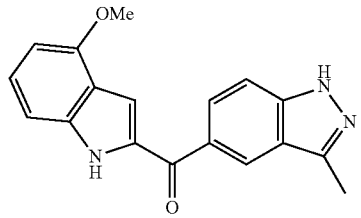 [SMILES: COc1cccc2[nH]c(C(=O)c3ccc4[nH]nc(C)c4c3)cc12]

1. To a solution of 5-bromo-3-methyl-1H-indazole (2.11 g, 10.0 mmol) in 50 mL of THF, was added 6.3 mL of n-BuLi solution in hexanes (1.7 M) at −78° C. After 10 minutes, 17.6 mL of t-BuLi solution in pentane (1.6 M) at −78° C. After 1 hr, DMF (10 mL) was added. After 10 minutes, the reaction was allowed to warm up to RT. After 10 minutes, the reaction was quenched with saturated ammonium chloride, and extracted with EtOAc. The organic layer was washed with brine (×2), dried (MgSO$_4$), and concentrated to give crude 3-methyl-1H-indazole-5-carbaldehyde (quant.) as a brownish solid. $^1$H NMR (399 MHz, DMSO-d$_6$) δ ppm 13.08 (1H, br. s.), 9.98 (1H, s), 8.36 (1H, s), 7.78 (1H, dd, J=8.6, 1.2 Hz), 7.55 (1H, d, J=8.6 Hz), 2.53 (3H, s)

2. To a solution of 3-methyl-1H-indazole-5-carbaldehyde (1.68 g, 10.0 mmol) in 50 mL of dichloromethane, were added phenylsulfonylchloride (1.4 mL, 11.0 mmol), triethylamine (7.0 mL, 50.0 mmol), and DMAP (122 mg, 1.00 mmol). The reaction mixture was stirred at RT for 18 hr, diluted with EtOAc, washed with saturated ammonium chloride, dried (MgSO$_4$), and concentrated. The residue was purified over 100 g SiO$_2$ (60% EtOAc/Hexanes) to give 3-methyl-1-(phenylsulfonyl)-1H-indazole-5-carbaldehyde (2.50 g, 8.32 mmol, 83%) as an off white solid. $^1$H NMR (399 MHz, DMSO-d$_6$) δ ppm 10.06 (1H, s), 8.43 (1H, s), 8.24 (1H, d, J=8.6 Hz), 8.12 (1H, dd, J=8.8, 1.4 Hz), 7.89-7.95 (2H, m), 7.66-7.74 (1H, m), 7.49-7.63 (2H, m), 2.53 (3H, s)

3. To a cooled solution of 4-methoxy-1H-indole (0.735 g, 5.00 mmol) in 10 mL of DMF, was added sodium hydride (60 wt % dispersion, 200 mg, 5.00 mmol) at 0° C. After 1 hr, phenylsulfonylchloride (0.64 mL, 5.00 mmol) was added. After 1 hr, the reaction was quenched with saturated sodium bicarbonate solution, and extracted with EtOAc. The organic layer was dried (MgSO$_4$), and concentrated. The residue was purified over 25 g SiO$_2$ (25% EtOAc/Hexanes) to give 4-methoxy-1-(phenylsulfonyl)-1H-indole (0.920 g, 3.20 mmol, 64%) as an off white solid. $^1$H NMR (399 MHz, CHLOROFORM-d) δ ppm 7.83-7.88 (2H, m), 7.58 (1H, d, J=8.6 Hz), 7.48-7.54 (1H, m), 7.46 (1H, d, J=3.5 Hz), 7.38-7.44 (2H, m), 7.16-7.26 (1H, m), 6.74-6.80 (1H, m), 6.63 (1H, d, J=7.8 Hz), 3.87 (3H, s)

4. To a solution of 4-methoxy-1-(phenylsulfonyl)-1H-indole (117 mg, 0.407 mmol) in 4 mL of THF, was added 0.30 mL of n-BuLi solution in hexanes (1.6 M) at −78° C. After 1 hr, a solution of 3-methyl-1-(phenylsulfonyl)-1H-indazole-5-carbaldehyde (134 mg, 0.448 mmol) in 3 mL of THF was added slowly. After 1 hr, the reaction mixture was allowed to warm up to RT slowly, quenched with saturated sodium bicarbonate solution, and extracted with EtOAc. The organic layer was washed with brine, dried (MgSO$_4$), and concentrated. Chromatography over 25 g SiO$_2$ (60% EtOAc/Hexanes) gave ((4-methoxy-1-(phenylsulfonyl)-1H-indol-2-yl)(3-methyl-1H-indazol-5-yl)methanol (90 mg, 0.15 mmol, 38%) as an oil. $^1$H NMR (399 MHz, DMSO-d$_6$) δ ppm 8.02 (1H, d, J=8.6 Hz), 7.87-7.93 (1H, m), 7.62-7.73 (4H, m), 7.51-7.62 (4H, m), 7.48 (1H, t, J=7.6 Hz), 7.27-7.34 (1H, m), 7.21 (1H, t, J=8.2 Hz), 6.75 (1H, d, J=8.2 Hz), 6.45-6.52 (2H, m), 6.28 (1H, d, J=5.5 Hz), 3.77 (3H, s), 2.39 (3H, s)

5. ((4-methoxy-1-(phenylsulfonyl)-1H-indol-2-yl)(3-methyl-1H-indazol-5-yl)methanol was dissolved in 10 mL of dichloromethane, and reacted with MnO$_2$ (532 mg, 6.12 mmol) overnight at RT. The reaction mixture was diluted with EtOAc, filtered through a pad of Celite, and concentrated to give (4-methoxy-1-(phenylsulfonyl)-1H-indol-2-yl)(3-methyl-1H-indazol-5-yl)methanone (79 mg, 0.14 mmol, 90%) as a red solid. $^1$H NMR (399 MHz, DMSO-d$_6$) δ ppm 8.32 (1H, dd, J=1.6, 0.8 Hz), 8.21-8.27 (1H, m), 8.17 (1H, dd, J=8.6, 1.6 Hz), 7.91-7.99 (4H, m), 7.65-7.74 (2H, m), 7.55-7.64 (4H, m), 7.44 (2H, t, J=8.2 Hz), 7.15-7.21 (1H, m), 6.87 (1H, d, J=8.2 Hz), 3.83 (3H, s), 2.49 (2H, s)

6. To a solution of (4-methoxy-1-(phenylsulfonyl)-1H-indol-2-yl)(3-methyl-1H-indazol-5-yl)methanone in 13 mL of THF, was added 1.3 mL of TBAF solution in THF (1 M). The reaction mixture was stirred at 55° C. overnight, cooled to RT, diluted with EtOAc, washed with brine (×2), dried (MgSO$_4$), and concentrated. Chromatography over 10 g SiO$_2$ (80% EtOAc/Hexanes) gave (4-methoxy-1H-indol-2-yl)(3-methyl-1H-indazol-5-yl)methanone (26 mg, 0.085 mmol, 64%) as an orange solid. $^1$H NMR (399 MHz, DMSO-d$_6$) δ ppm 12.97 (1H, s), 11.94 (1H, s), 8.33 (1H, s), 7.89 (1H, dd, J=8.6, 1.6 Hz), 7.58 (1H, d, J=8.6 Hz), 7.18-7.23 (1H, m), 7.03-7.07 (2H, m), 6.53 (1H, d, J=7.8 Hz), 3.86 (3H, s), 2.54 (3H, s); MS (ESI) m/z Calculated 305.12 Found 306.27 (M+H)+.

Example 30

(4-(benzyloxy)-1H-indol-2-yl)(3-methyl-1H-indazol-5-yl)methanone

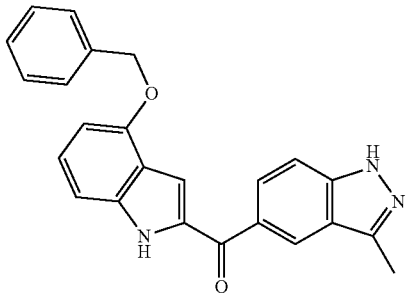 [SMILES: Cc1n[nH]c2ccc(C(=O)c3cc4c(OCc5ccccc5)cccc4[nH]3)cc12]

1. To a cooled solution of 4-(benzyloxy)-1H-indole (1.12 g, 5.00 mmol) in 10 mL of DMF, was added sodium hydride (60 wt % dispersion, 220 mg, 5.50 mmol) at 0° C. After 1 hr, phenylsulfonylchloride (0.77 mL, 6.00 mmol) was added. After 1 hr, the reaction was quenched with saturated sodium bicarbonate solution, and extracted with EtOAc. The organic layer was dried (MgSO$_4$), and concentrated The residue was purified over 25 g SiO$_2$ (25% EtOAc/Hexanes) to give 4-(benzyloxy)-1-(phenylsulfonyl)-1H-indole (0.820 g, 2.26 mmol, 45%) as an off white solid. $^1$H NMR (399 MHz, CHLOROFORM-d) δ ppm 7.79-7.89 (2H, m), 7.56-7.64 (1H, m), 7.46-7.55 (2H, m), 7.28-7.46 (5H, m), 7.15-7.28 (2H, m), 6.99-7.14 (1H, m), 6.75-6.88 (1H, m), 6.62-6.74 (1H, m), 6.58 (1H, d, J=7.8 Hz), 5.13 (2H, s)

2. To a solution of 4-(benzyloxy)-1-(phenylsulfonyl)-1H-indole (363 mg, 1.00 mmol) in 5 mL of THF, was added 0.75 mL of n-BuLi solution in hexanes (1.6 M) at −78° C. After 1 hr, a solution of 3-methyl-1-(phenylsulfonyl)-1H-indazole-5-carbaldehyde (600 mg, 2.00 mmol) in 5 mL of THF was added slowly. After 2 hr, the reaction mixture was allowed to warm up to RT slowly, quenched with saturated sodium bicarbonate solution, and extracted with EtOAc. The organic layer was washed with brine, dried (MgSO$_4$), and concentrated. Chromatography over 25 g SiO$_2$ (60% EtOAc/Hexanes) gave (4-(benzyloxy)-1-(phenylsulfonyl)-1H-indol-2-yl)(3-methyl-1H-indazol-5-yl)methanol (195 mg, 0.294 mmol, 29%) as an oil, which was dissolved in 10 mL of dichloromethane, and reacted with MnO$_2$ (1.02 g, 11.8 mmol) overnight at RT. The reaction mixture was diluted with EtOAc, filtered through a pad of Celite, and concentrated to give (4-(benzyloxy)-1-(phenylsulfonyl)-1H-indol-2-yl)(3-methyl-1H-indazol-5-yl)methanone (173 mg, 0.261 mmol, 89%) as an oil. $^1$H NMR (399 MHz, DMSO-d$_6$) δ ppm 8.33 (1H, s), 8.24 (1H, d, J=8.6 Hz), 8.17 (1H, dd, J=8.6, 1.6 Hz), 7.93-8.00 (2H, m), 7.65-7.74 (3H, m), 7.54-7.65 (3H, m), 7.38-7.47 (2H, m), 7.22-7.35 (3H, m), 6.93-7.01 (1H, m), 5.20 (2H, s), 2.49 (3H, s)

3. To a solution of (4-(benzyloxy)-1-(phenylsulfonyl)-1H-indol-2-yl)(3-methyl-1H-indazol-5-yl)methanone in 10 mL of THF, was added 2.6 mL of TBAF solution in THF (1 M). The reaction mixture was stirred at 55° C. overnight, cooled to RT, diluted with EtOAc, washed with brine (×2), dried (MgSO$_4$), and concentrated. Chromatography over 10 g SiO$_2$ (80% EtOAc/Hexanes) gave (4-(benzyloxy)-1H-indol-2-yl)(3-methyl-1H-indazol-5-yl)methanone (65 mg, 0.17 mmol, 66%) as a brown solid. $^1$H NMR (399 MHz, DMSO-d$_6$) δ ppm 12.97 (1H, s), 11.97 (1H, s), 8.33 (1H, s), 7.87-7.90 (1H, m), 7.58 (1H, d, J=8.6 Hz), 7.46 (2H, d, J=7.8 Hz), 7.32-7.37 (2H, m), 7.29 (1H, d, J=7.0 Hz), 7.16-7.21 (1H, m), 7.07 (2H, m), 6.63 (1H, d, J=7.8 Hz), 5.22 (2H, s), 2.53 (3H, s); MS (ESI) m/z Calculated 381.15 Found 382.31 (M+H)+.

Example 31

(5-methoxy-1H-pyrrolo[2,3-c]pyridin-2-yl)(3-methyl-1H-indazol-5-yl)methanone

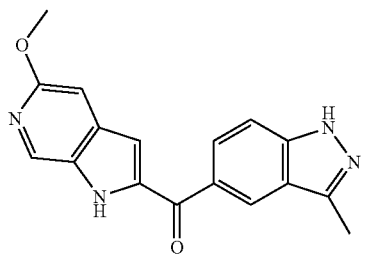 [SMILES: COc1cc2cc(C(=O)c3ccc4[nH]nc(C)c4c3)[nH]c2cn1]

1. The mixture of 2-methoxy-4-methyl-5-nitropyridine (1.68 g, 10.0 mmol) and 1,1-dimethoxy-N,N-dimethylmethanamine (14 Ml, 103 mmol) in 10 mL of DMF was heated at 130° C. overnight, cooled to RT, diluted with EtOAc, washed with water and brine, dried (MgSO$_4$), and concentrated. The residue was dissolved in 70 mL of EtOH. To this solution was added 1.06 g of 10% Pd/C. The mixture was stirred under 1 atm of hydrogen atmosphere over 4 days, filtered through a pad of Celite, and washed with EtOH. The filtrate was concentrated to give crude 5-methoxy-1H-pyrrolo[2,3-c]pyridine (quant.). $^1$H NMR (399 MHz, DMSO-d$_6$) δ ppm 11.26 (1H, br. s.), 8.33 (1H, s), 7.53 (1H, d, J=2.7 Hz), 6.73-6.88 (1H, m), 6.32 (1H, d, J=3.1 Hz), 3.30 (3H, s).

2. To a cooled solution of crude 5-methoxy-1H-pyrrolo[2,3-c]pyridine in 50 mL of THF was added NaH (520 mg, 13.0 mmol) at 0° C. After 1 hr, phenylsulfonylchloride (1.4 mL, 11.0 mmol) was added. After 2 hr, the reaction was quenched with saturated ammonium chloride solution, extracted with EtOAc, and washed with brine. The organic layer was dried (MgSO$_4$), and concentrated The residue was purified over 100 g SiO$_2$ (60% EtOAc/Hexanes) to give 5-methoxy-1-(phenylsulfonyl)-1H-pyrrolo[2,3-c]pyridine (2.17 g, 7.53 mmol, 75% for 3 steps) as a white solid. $^1$H NMR (399 MHz, CHLOROFORM-d) δ ppm 8.85 (1H, s), 7.86-7.92 (2H, m), 7.61 (1H, d, J=3.9 Hz), 7.57 (1H, t, J=7.6 Hz), 7.46 (2H, t, J=7.8 Hz), 6.80 (1H, s), 6.55 (1H, d, J=3.5 Hz), 3.94 (3H, s).

3. To a solution of 5-methoxy-1-(phenylsulfonyl)-1H-pyrrolo[2,3-c]pyridine (433 mg, 1.50 mmol) in 10 mL of THF, was added 0.69 mL of n-BuLi solution in hexanes (1.6 M) at −78° C. After 1 hr, a solution of 3-methyl-1-(phenylsulfonyl)-1H-indazole-5-carbaldehyde (300 mg, 1.00 mmol) in 5 mL of THF was added slowly. After 1 hr, the reaction mixture was allowed to warm up to RT slowly, quenched with saturated ammonium chloride solution, and extracted with EtOAc. The organic layer was washed with brine, dried (MgSO$_4$), and concentrated. Chromatography over 25 g SiO$_2$ (80% EtOAc/Hexanes) gave (5-methoxy-1-(phenylsulfonyl)-1H-pyrrolo[2,3-c]pyridin-2-yl)(3-methyl-1-(phenylsulfonyl)-1H-indazol-5-yl)methanol (200 mg, 0.340 mmol, 34%) as an oil, which was dissolved in 10 mL of dichloromethane, and reacted with MnO$_2$ (1.18 g, 13.6 mmol) overnight at RT. The reaction mixture was diluted with EtOAc, filtered through a pad of Celite, and concentrated to give (5-methoxy-1-(phenylsulfonyl)-1H-pyrrolo[2,3-c]pyridin-2-yl)(3-methyl-1-(phenylsulfonyl)-1H-indazol-5-yl)methanone (166 mg, 0.283 mmol, 83%). $^1$H NMR (399 MHz, CHLOROFORM-d) δ ppm 10.02-10.14 (1H, m), 9.00 (1H, s), 8.14-8.34 (2H, m), 7.88-8.06 (5H, m), 7.57-7.66 (2H, m), 7.43-7.55 (4H, m), 6.85 (1H, d, J=0.8 Hz), 6.77 (1H, s), 3.98 (3H, s), 2.65 (H, s)

4. To a solution of (5-methoxy-1-(phenylsulfonyl)-1H-pyrrolo[2,3-c]pyridin-2-yl)(3-methyl-1-(phenylsulfonyl)-1H-indazol-5-yl)methanone in 5 mL of THF, was added 2.8 mL of TBAF solution in THF (1 M). The reaction mixture was stirred at 50° C. overnight, cooled to RT, diluted with EtOAc, washed with brine (×2), dried (MgSO$_4$), and concentrated. Chromatography over 25 g SiO$_2$ (20 to 100% EtOAc/Hexanes) gave (5-methoxy-1H-pyrrolo[2,3-c]pyridin-2-yl)(3-methyl-1H-indazol-5-yl)methanone (45 mg, 0.147 mmol, 43%), which was recrystallized from ethyl ether. $^1$H NMR (399 MHz, DMSO-d$_6$) δ ppm 13.04 (1H, s), 12.08 (1H, s), 8.53 (1H, s), 8.42 (1H, s), 7.93 (1H, dd, J=8.8, 1.6 Hz), 7.61 (1H, d, J=8.8 Hz), 7.07 (1H, d, J=1.6 Hz), 7.02 (1H, s), 3.84 (3H, s), 2.55 (3H, s); MS (ESI) m/z Calculated 306.11 Found 307.24 (M+H)+.

Example 32

(1H-indol-5-yl)(1H-pyrrolo[2,3-b]pyridin-2-yl)methanone

1. The mixture of 1H-pyrrolo[2,3-b]pyridine (5 g, 42.3 mmol), phenylsulfonylchloride (5.81 mL, 45.3 mmol), diisopropylethylamine (36.8 mL, 211.6 mmol), and DMAP (517 mg, 4.23 mmol) in 300 mL of dichloromethane was stirred at RT for overnight, diluted with dichloromethane, washed with water, was dried (MgSO$_4$), and concentrated. The residue was purified by chromatography (30% EtOAc/Hexanes) to give 1-(phenylsulfonyl)-1H-pyrrolo[2,3-b]pyridine (10.7 g, 98%). $^1$H NMR (400 MHz, CDCl$_3$) δ ppm:

8.42 (dd, J=4.4, 1.6 Hz, 1H), 8.20 (d, J=7.2 Hz, 2H), 7.84 (dd, J=8.0, 1.6 Hz, 1H), 7.73 (d, J=4.0 Hz, 1H), 7.56 (t, J=7.6 Hz, 1H), 7.47 (t, J=8.0 Hz, 2H), 7.17 (q, J=4.8 Hz, 1H), 6.60 (d, J=4.0 Hz, 1H),

2. To a solution of 5-bromo-1H-indole (3.5 g, 17.85 mmol) in 100 mL of ethyl ether, was added 52.5 mL of t-BuLi solution in pentane (1.7 M) at −78° C. After 1 hr at −78° C., the reaction mixture was added DMF (25 mL). After 2 hr at 0° C., the reaction was quenched with saturated ammonium chloride, and extracted with EtOAc (×3). The combined organic extracts were washed with water, brine, dried (MgSO$_4$), filtered, and concentrated to give crude 1H-indole-5-carbaldehyde (quant.).

The mixture of 1H-indole-5-carbaldehyde (1 g, 6.89 mmol), Di-tert-butyl dicarbonate (2.25 g, 10.3 mmol), and DMAP (42 mg, 0.344 mmol) in 70 mL of dichloromethane was stirred at RT for overnight, The reaction mixture was poured into water, and extracted with EtOAc (×3). The combined organic extracts were washed with water, dried (MgSO$_4$), filtered, and concentrated. Flash chromatography (15% EtOAc/Hexanes) gave tert-butyl 5-formyl-1H-indole-1-carboxylate (1.63 g, 96%). $^1$H NMR (400 MHz, CDCl$_3$) δ ppm: 10.05 (s, 1H), 8.28 (d, J=8.4 Hz, 1H), 8.08 (s, 1H), 7.85 (dd, J=8.4, 1.6 Hz, 1H), 7.67 (d, J=3.6 Hz, 1H), 6.68 (d, J=3.6 Hz, 1H), 1.67 (s, 9H).

3. To a solution of 1-(phenylsulfonyl)-1H-pyrrolo[2,3-b]pyridine (516 mg, 2.0 mmol) in 10 mL of THF, was added 0.88 mL of n-BuLi solution in hexanes (2.5 M) at −78° C. After 1 hr, a solution of tert-butyl 5-formyl-1H-indole-1-carboxylate (490 mg, 2.0 mmol) in 7 mL of THF was added slowly. The reaction mixture was allowed to warm up to RT slowly, After 1 hr, The reaction was quenched with saturated ammonium chloride solution, and extracted with EtOAc (×3). The combined organic extracts were dried (MgSO$_4$), filtered, and concentrated. Flash chromatography (50% EtOAc/Hexanes) gave tert-butyl 5-(hydroxy(1-(phenylsulfonyl)-1H-pyrrolo[2,3-b]pyridin-2-yl)methyl)-1H-indole-1-carboxylate (652 mg, 65%). $^1$H NMR (400 MHz, CDCl$_3$) δ ppm: 8.38 (dd, J=4.8, 1.6 Hz, 1H), 8.15 (d, J=8.4 Hz, 1H), 7.97 (d, J=7.2 Hz, 2H), 7.69 (dd, J=8.8, 1.6 Hz, 1H), 7.64 (s, 1H), 7.62 (d, J=4.8 Hz, 1H), 7.49 (t, J=7.6 Hz, 1H), 7.40 (dd, J=8.8, 1.6 Hz, 1H), 7.33 (t, J=7.6 Hz, 2H), 7.13 (q, J=4.8 Hz, 1H), 6.64 (s, 1H), 6.54 (d, J=3.6 Hz, 1H), 6.25 (s, 1H), 3.62 (br.s, 1H), 1.67 (s, 9H).

4. The mixture of tert-butyl 5-(hydroxy(1-(phenylsulfonyl)-1H-pyrrolo[2,3-b]pyridin-2-yl)methyl)-1H-indole-1-carboxylate (650 mg, 1.29 mmol), and MnO$_2$ (1.12 g, 12.9 mmol) in 20 mL of dichloromethane was stirred over weekend at RT, diluted with dichloromethane, filtered through a pad of Celite, and concentrated to give tert-butyl 5-(1-(phenylsulfonyl)-1H-pyrrolo[2,3-b]pyridine-2-carbonyl)-1H-indole-1-carboxylate (589 mg, 90.6%). $^1$H NMR (400 MHz, CDCl$_3$) δ ppm: 8.59 (dd, J=4.8, 1.6 Hz, 1H), 8.41 (d, J=7.2 Hz, 2H), 8.27 (d, J=8.8 Hz, 1H), 8.23 (s, 1H), 8.04 (dd, J=8.8, 2.0 Hz, 1H), 7.92 (dd, J=8.0, 2.0 Hz, 1H), 7.69 (d, J=4.0 Hz, 1H), 7.61 (t, J=6.8 Hz, 1H), 7.53 (t, J=7.2 Hz, 2H), 7.27 (q, J=4.8 Hz, 1H), 6.82 (s, 1H), 6.65 (d, J=4.0 Hz, 1H) 1.70 (s, 9H).

5. The mixture of tert-butyl 5-(1-(phenylsulfonyl)-1H-pyrrolo[2,3-b]pyridine-2-carbonyl)-1H-indole-1-carboxylate (589 mg, 1.17 mmol), and 12 g of silica gel in 25 mL of Toluene was reflued for 5.5 hr. After cooled to RT, the solvent was evaporated, and flashed with chromatography (75% EtOAc/Hexanes) gave (1H-indol-5-yl)(1-(phenylsulfonyl)-1H-pyrrolo[2,3-b]pyridin-2-yl)methanone (quant.).

To a solution of (1H-indol-5-yl)(1-(phenylsulfonyl)-1H-pyrrolo[2,3-b]pyridin-2-yl)methanone (471 mg, 1.175 mmol) in 20 mL of THF, was added Tetra-butylammonium fluoride trihydrate (3.07 g. 11.75 mmol). The reaction mixture was refluxed for 5.5 hr. After cooled to RT, the reaction mixture was poured into water, and extracted with EtOAc (×3). The combined organic extracts were washed with water (×2), dried (MgSO$_4$), filtered, and concentrated. The crude product was trituration with dichloromethane gave (1H-indol-5-yl)(1H-pyrrolo[2,3-b]pyridin-2-yl)methanone (306 mg, quant.). $^1$H NMR (400 MHz, DMSO-d$_6$) δ ppm: 12.39 (s, 1H), 11.52 (s, 1H), 8.42 (dd, J=4.4, 1.2 Hz, 1H), 8.28 (s, 1H), 8.16 (d, J=8.0 Hz, 1H), 7.73 (dd, J=8.4, 1.6 Hz, 1H), 7.56 (d, J=8.4 Hz, 1H), 7.49 (t, J=3.2 Hz, 1H), 7.16 (q, J=4.8 Hz, 1H), 7.11 (d, J=2.4 Hz, 1H), 6.64 (s, 1H).

Example 33

(5-methoxy-1H-indol-2-yl)(1H-pyrrolo[2,3-b]pyridin-5-yl)methanone

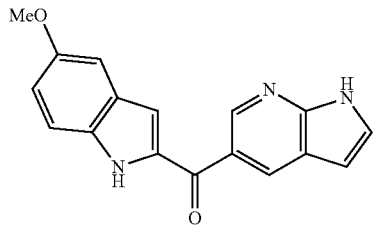 [SMILES: COc1ccc2[nH]c(C(=O)c3cnc4[nH]ccc4c3)cc2c1]

1. To a solution of 5-bromo-1H-pyrrolo[2,3-b]pyridine (600 mg, 3.045 mmol) in 20 mL of THF, was added sodium hydride (60 wt % dispersion, 146 mg, 3.65 mmol) at 0° C. After 30 min, the reaction was added 4.38 mL of n-BuLi solution in hexanes (1.6 M) at −15° C. After 1 hr at −15° C., DMF (10 mL) was added and allowed to warm to RT. After 2 hr, the reaction was quenched with water, and extracted with EtOAc (×3). The combined organic extracts were washed with water (×2), dried (MgSO$_4$), and concentrated to give crude 1H-pyrrolo[2,3-b]pyridine-5-carbaldehyde (572.8 mg).

To solution of crude 1H-pyrrolo[2,3-b]pyridine-5-carbaldehyde (572.8 mg, 3.92 mmol) in 30 mL of THF, was added sodium hydride (60 wt % dispersion, 314 mg, 7.84 mmol) at 0° C. After 1.5 hr at RT, phenylsulfonylchloride (1.0 mL, 7.84 mmol) was added. After 2 hr, the reaction was quenched with saturated ammonium chloride solution at 0° C., and extracted with EtOAc (×3). The combined organic extracts were dried (MgSO$_4$), filtered, and concentrated. Flash chromatography (35% EtOAc/Hexanes) gave 1-(phenylsulfonyl)-1H-pyrrolo[2,3-b]pyridine-5-carbaldehyde (381 mg, 34%). $^1$H NMR (400 MHz, CDCl$_3$) δ ppm: 10.13 (s, 1H), 8.90 (s, 1H), 8.36 (s, 1H), 8.24 (d, J=8.0 Hz, 2H), 7.86 (d, J=4.0 Hz, 1H), 7.62 (t, J=7.6 Hz, 1H), 7.52 (t, J=8.0 Hz, 2H), 6.73 (d, J=4.0 Hz, 1H).

2. To a solution of 5-methoxy-1-(phenylsulfonyl)-1H-indole (420 mg, 1.46 mmol) in 8 mL of THF, was added 0.92 mL of n-BuLi solution in hexanes (1.6 M) at −78° C. After 1 hr, a solution of 1-(phenylsulfonyl)-1H-pyrrolo[2,3-b]pyridine-5-carbaldehyde (381 mg, 1.33 mmol) in 10 mL of THF was added slowly. The reaction mixture was allowed to warm up to RT slowly. After 2 hr, the reaction was quenched with water, and extracted with EtOAc (×3). The combined organic extracts were dried (MgSO$_4$), filtered, and concentrated to give crude (5-methoxy-1-(phenylsulfonyl)-1H-indol-2-yl)(1-(phenylsulfonyl)-1H-pyrrolo[2,3-b]pyridin-5-yl)methanol The mixture of crude (5-methoxy-1-(phenylsulfonyl)-1H-indol-2-yl)(1-(phenylsulfonyl)-1H-pyrrolo[2,3-b]pyridin-5-yl)methanol and MnO$_2$ (1.71 g, 20 mmol) in 30 mL of dichloromethane was stirred overnight at RT. After overnight, the reaction mixture was filtered through a pad of Celite, and concentrated. Flash chromatography (40% EtOAc/Hexanes) gave (5-methoxy-1-(phenylsulfonyl)-1H-indol-2-yl)(1-(phenylsulfonyl)-1H-pyrrolo[2,3-b]pyridin-5-yl)methanone (168 mg, 23% for two step). $^1$H NMR (400 MHz, CDCl$_3$) δ ppm: 9.01 (d, J=2.0 Hz, 1H), 8.44 (d, J=2.0 Hz, 1H), 8.23 (d, J=7.2 Hz, 2H), 8.03 (d, J=9.2 Hz, 1H), 7.96 (d, J=7.6 Hz, 2H), 7.84 (d, J=4.0 Hz, 1H), 7.65-7.43 (m, 6H), 7.10 (dd, J=9.2, 2.4 Hz 1H), 6.97 (d, J=2.4 Hz, 1H), 6.90 (s, 1H), 6.70 (d, J=4.0 Hz 1H), 3.83 (s, 3H).

3. To a solution of (5-methoxy-1-(phenylsulfonyl)-1H-indol-2-yl)(1-(phenylsulfonyl)-1H-pyrrolo[2,3-b]pyridin-5-yl)methanone (168 mg, 0.295 mmol) in 2 mL of THF, added 9.23 mL of TBAF solution in THF (1 M). The reaction mixture was heated to reflux for overnight. After cooled to RT, the reaction mixture was poured into water, and extracted with EtOAc (×3). The combined organic extracts were washed with water, dried (MgSO$_4$), filtered, and concentrated. Flash chromatography (60% EtOAc/Hexanes) gave (5-methoxy-1H-indol-2-yl)(1H-pyrrolo[2,3-b]pyridin-5-yl)methanone (49 mg, 59%). $^1$H NMR (400 MHz, DMSO-d$_6$) δ ppm: 12.07 (s, 1H), 11.83 (s, 1H), 8.77 (d, J=2.0 Hz, 1H), 8.55 (d, J=2.0 Hz, 1H), 7.26 (t, J=3.2 Hz, 1H), 7.40 (d, J=8.8 Hz, 1H), 7.16 (d, J=2.4 Hz 1H), 7.08 (d, J=2.4 Hz, 1H), 6.97 (dd, J=8.8, 2.4 Hz, 1H), 6.64 (q, J=2.0 Hz 1H), 3.75 (s, 3H). MS: 292.22 (M+H+).

Example 34

(5-methoxy-1H-indol-2-yl)(2-methyl-1H-benzo[d]imidazol-5-yl)methanone

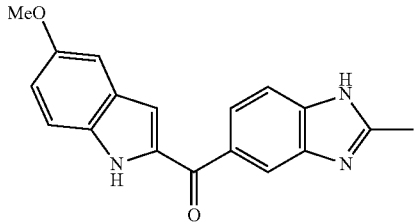 [SMILES: COc1ccc2[nH]c(C(=O)c3ccc4[nH]c(C)nc4c3)cc2c1]

1. To a solution of 5-bromo-2-methyl-1H-benzo[d]imidazole (422 mg, 2.00 mmol) in 20 mL of THF, was added 4.1 mL of t-BuLi solution in hexanes (1.6 M) at −78° C. After 1 hr, a solution of 5-methoxy-1-(phenylsulfonyl)-1H-indole-2-carbaldehyde (693 mg, 2.20 mmol) in 10 mL of THF was added slowly. After 2 hr, the reaction mixture was allowed to warm up to RT slowly, quenched with saturated ammonium chloride solution, and extracted with EtOAc. The organic layer was washed with brine, dried (MgSO$_4$), and concentrated to give impure (5-methoxy-1-(phenylsulfonyl)-1H-indol-2-yl)(2-methyl-1H-benzo[d]imidazol-5-yl)methanol, which was dissolved in 20 mL of dichloromethane and 20 mL of THF, and reacted with MnO$_2$ (3.50 g, 40.0 mmol) overnight at RT. The reaction mixture was diluted with EtOAc, filtered through a pad of Celite, and concentrated to give crude product, which was used for the next step without any further purification.

2. To a solution crude (5-methoxy-1-(phenylsulfonyl)-1H-indol-2-yl)(2-methyl-1H-benzo[d]imidazol-5-yl)methanone (475 mg, 1.07 mmol) in 10 mL of THF, was added 5.0 mL of TBAF solution in THF (1 M). The reaction mixture was heated to reflux overnight, cooled to RT, diluted with EtOAc, washed with brine (×2), dried (MgSO$_4$), and concentrated. Chromatography over 50 g SiO$_2$ (10% MeOH/DCM) gave (5-methoxy-1H-indol-2-yl)(2-methyl-1H-benzo[d]imidazol-5-yl)methanone (45 mg, 0.15 mmol, 14%) as a brownish solid. $^1$H NMR (399 MHz, DMSO-d$_6$) δ ppm 12.54 (1H, d, J=9.0 Hz), 11.77 (1H, d, J=4.7 Hz), 8.09 (1H, s), 8.00 (1H, s), 7.69-7.79 (1H, m), 7.64 (1H, d, J=8.6 Hz), 7.55 (1H, d, J=8.2 Hz), 7.39 (1H, d, J=8.2 Hz), 3.75 (3H, s); MS (ESI) m/z Calculated 305.12 Found 360.22 (M+H)+.

Example 35

(5-methoxy-1H-indol-2-yl)(2-(trifluoromethyl)-1H-benzo[d]imidazol-5-yl)methanone

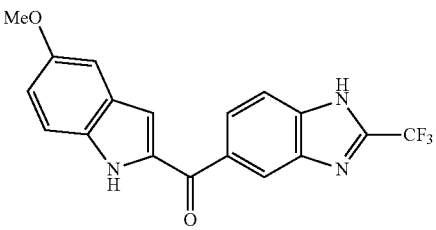 [SMILES: COc1ccc2[nH]c(C(=O)c3ccc4[nH]c(C(F)(F)F)nc4c3)cc2c1]

1. Methyl 2-(trifluoromethyl)-1H-benzo[d]imidazole-5-carboxylate was prepared by known procedure (Eur. J. Med. Chem., 2012, 52, 193-204). To a solution of ethyl 2-(trifluoromethyl)-1H-benzo[d]imidazole-5-carboxylate (0.952 g, 3.90 mmol) in 20 mL of THF, was added LAH (0.222 g, 5.85 mmol) at RT. The reaction mixture was stirred for 3 hr, and partitioned between EtOAc and iced water. The aqueous layer was acidified to pH 3 using 10% sulfuric acid, and extracted with EtOAc. The combined organic layers were dried (MgSO$_4$), and concentrated to give crude (2-(trifluoromethyl)-1H-benzo[d]imidazol-5-yl)methanol, which was dissolved in 40 mL of THF, and reacted with MnO$_2$ (3.4 g, 39.0 mmol) overnight. The reaction mixture was diluted with dichloromethane, filtered through a pad of Celite, and concentrated to give 2-(trifluoromethyl)-1H-benzo[d]imidazole-5-carbaldehyde (0.704 mg, 3.29 mmol, 84%) as an off white solid. $^1$H NMR (399 MHz, DMSO-d$_6$) δ ppm 10.10 (1H, s), 8.34 (1H, br. s.), 7.73-8.01 (2H, m)

2. To a solution of 2-(trifluoromethyl)-1H-benzo[d]imidazole-5-carbaldehyde (0.704 g, 3.29 mmol) in 17 mL of dichloromethane, were added phenylsulfonylchloride (0.46 mL, 3.62 mmol), diisopropylethylamine (2.9 mL, 16.5 mmol), and DMAP (40 mg, 0.33 mmol). The reaction mixture was stirred at RT for 18 hr, diluted with dichloromethane, washed with water and brine, dried (MgSO$_4$), and concentrated. The residue was purified over 50 g SiO$_2$ (80% EtOAc/Hexanes) to give 1-(phenylsulfonyl)-2-(trifluoromethyl)-1H-benzo[d]imidazole-5-carbaldehyde (a mixture of two regioisomers, 0.967 g, 2.73 mmol, 83%) as an off white solid. $^1$H NMR (399 MHz, CHLOROFORM-d) δ ppm 10.19-10.12 (1H, 2s), 8.68-8.72 (0.4H, m), 8.29-8.37 (1H, m), 8.16-8.15 (0.6H, m), 8.03-8.10 (2H, m), 8.01 (1H, s), 7.67-7.77 (1H, m), 7.53-7.63 (2H, m)

3. To a solution of 5-methoxy-1-(phenylsulfonyl)-1H-indole (287 mg, 1.00 mmol) in 6 mL of THF, was added 0.75 mL of n-BuLi solution in hexanes (1.6 M) at −78° C. After 1 hr, a solution of 1-(phenylsulfonyl)-2-(trifluoromethyl)-1H-benzo[d]imidazole-5-carbaldehyde (390 mg, 1.10 mmol) in 4 mL of THF was added slowly. After 4 hr, the reaction mixture was allowed to warm up to RT slowly, quenched with saturated ammonium chloride solution, and extracted with EtOAc. The organic layer was washed with brine, dried (MgSO$_4$), and concentrated. Chromatography over 25 g SiO$_2$ (50% EtOAc/Hexanes) gave (5-methoxy-1-(phenylsulfonyl)-1H-indol-2-yl)(1-(phenylsulfonyl)-2-(trifluoromethyl)-1H-benzo[d]imidazol-5-yl)methanol (298 mg, 0.491 mmol, 54%) as a brownish oil. $^1$H NMR (399 MHz, CHLOROFORM-d) δ ppm 8.13 (1H, d, J=8.6 Hz), 7.93-8.10 (3H, m), 7.81-7.86 (2H, m), 7.64-7.73 (3H, m), 7.42-7.62 (3H, m), 7.33-7.41 (2H, m), 6.93 (1H, ddd, J=9.0, 4.7, 2.3 Hz), 6.82 (1H, dd, J=13.9, 2.5 Hz), 6.39-6.51 (1H, m), 6.19 (1H, s), 6.09 (1H, s), 3.69-3.85 (3H, m)

4. The mixture of (3-chloro-1-(phenylsulfonyl)-1H-indol-5-yl)(5-methoxy-1-(phenylsulfonyl)-1H-indol-2-yl)methanol and MnO$_2$ (1.40 g, 16.0 mmol) in 20 mL of dichloromethane was stirred overnight at RT, diluted with dichloromethane, filtered through a pad of Celite, and concentrated to give (5-methoxy-1-(phenylsulfonyl)-1H-indol-2-yl)(1-(phenylsulfonyl)-2-(trifluoromethyl)-1H-benzo[d]imidazol-5-yl)methanone (0.550 g, quant.) as a dark brown solid. $^1$H NMR (399 MHz, CHLOROFORM-d) δ ppm 8.28 (1H, d, J=1.2 Hz), 7.87-8.16 (5H, m), 7.66-7.77 (1H, m), 7.50-7.66 (3H, m), 7.40-7.50 (2H, m), 7.05-7.13 (1H, m), 6.91-7.05 (2H, m), 3.73-3.87 (2H, m)

5. To a solution (5-methoxy-1-(phenylsulfonyl)-1H-indol-2-yl)(1-(phenylsulfonyl)-2-(trifluoromethyl)-1H-benzo[d]imidazol-5-yl)methanone in 10 mL of THF, was added 8.6 mL of TBAF solution in THF (1 M). The reaction mixture was heated to reflux overnight, cooled to RT, diluted with EtOAc, washed with brine (×2), dried (MgSO$_4$), and concentrated. Chromatography over 25 g SiO$_2$ (80% EtOAc/Hexanes) gave (5-methoxy-1H-indol-2-yl)(2-(trifluoromethyl)-1H-benzo[d]imidazol-5-yl)methanone (0.113 g, 0.315 mmol, 37%) as a brownish solid. $^1$H NMR (399 MHz, DMSO-d$_6$) δ ppm 11.86 (1H, br. s.), 8.30 (1H, br. s.), 7.76-7.98 (2H, m), 7.40 (1H, d, J=9.0 Hz), 7.14 (1H, d, J=2.3 Hz), 7.07 (1H, d, J=1.6 Hz), 6.97 (1H, dd, J=9.0, 2.3 Hz), 3.76 (3H, s); MS (ESI) m/z Calculated 359.09 Found 360.11 (M+H)+.

Example 36

(1H-benzo[d][1,2,3]triazol-5-yl)(5-methoxy-1H-indol-2-yl)methanone

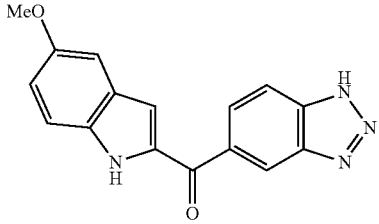 [SMILES: COc1ccc2[nH]c(C(=O)c3ccc4[nH]nnc4c3)cc2c1]

1. To a solution of 5-bromo-1H-benzo[d][1,2,3]triazole (396 mg, 2.00 mmol) in 10 mL of THF, was added 5.9 mL of t-BuLi solution in pentane (1.7 M) at −78° C. After 3 hr, a solution of 5-methoxy-1-(phenylsulfonyl)-1H-indole-2-carbaldehyde (756 mg, 2.40 mmol) in 5 mL of THF was added slowly. After 4 hr, the reaction mixture was allowed to warm up to RT slowly and stirred overnight, quenched with saturated ammonium chloride solution, and extracted with EtOAc. The organic layer was washed with water and brine, dried (MgSO$_4$), and concentrated. Chromatography over 50 g SiO$_2$ (80% EtOAc/Hexanes) (1H-benzo[d][1,2,3]triazol-5-yl)(5-methoxy-1-(phenylsulfonyl)-1H-indol-2-yl)methanol (174 mg, 0.401 mmol, 20%) as an oil. $^1$H NMR (399 MHz, CHLOROFORM-d) δ ppm 7.87-8.01 (2H, m), 7.79 (1H, d, J=5.9 Hz), 7.70 (2H, d, J=7.4 Hz), 7.43-7.63 (2H, m), 7.34 (3H, t, J=7.6 Hz), 6.86-6.98 (1H, m), 6.78 (1H, d, J=2.3 Hz), 6.51 (1H, s), 6.11 (1H, s), 3.71-3.81 (3H, s)

2. The mixture of (1H-benzo[d][1,2,3]triazol-5-yl)(5-methoxy-1-(phenylsulfonyl)-1H-indol-2-yl)methanol and MnO$_2$ (696 mg, 8.00 mmol) in 4 mL of THF and 2 mL of dichloromethane was stirred overnight at RT, diluted with EtOAc, filtered through a pad of Celite, and concentrated to give (1H-benzo[d][1,2,3]triazol-5-yl)(5-methoxy-1-(phenylsulfonyl)-1H-indol-2-yl)methanone (88 mg, 0.20 mmol, 51%) as a brown solid. $^1$H NMR (399 MHz, DMSO-d$_6$) δ ppm 8.39 (1H, s), 7.98-8.09 (3H, m), 7.81-7.91 (3H, m), 7.70 (1H, t, J=7.4 Hz), 7.58 (1H, t, J=7.8 Hz), 7.29 (1H, s), 7.12 (2H, m), 3.50-3.61 (3H, s)

3. To a solution of (1H-benzo[d][1,2,3]triazol-5-yl)(5-methoxy-1-(phenylsulfonyl)-1H-indol-2-yl)methanone in 4 mL of THF, was added 2.0 mL of TBAF solution in THF (1 M). The reaction mixture was heated to reflux overnight, cooled to RT, diluted with EtOAc, washed with brine (×2), dried (MgSO$_4$), and concentrated. Chromatography over 10 g SiO$_2$ (100% EtOAc/Hexanes) gave (1H-benzo[d][1,2,3]triazol-5-yl)(5-methoxy-1H-indol-2-yl)methanone (8 mg, 0.027 mmol, 13%) as a yellow solid. $^1$H NMR (399 MHz, DMSO-d$_6$) δ ppm 11.89 (1H, br. s.), 8.49 (1H, s), 7.85-8.16 (2H, m), 7.41 (1H, d, J=9.0 Hz), 7.15 (1H, d, J=2.3 Hz), 7.10 (2H, d, J=1.2 Hz), 6.98 (1H, dd, J=9.0, 2.3 Hz), 3.75 (3H, s); MS (ESI) m/z Calculated 292.10 Found 293.16 (M+H)+.

Example 37

(1H-indol-5-yl)(5-methoxy-1H-indol-2-yl)methanone oxime

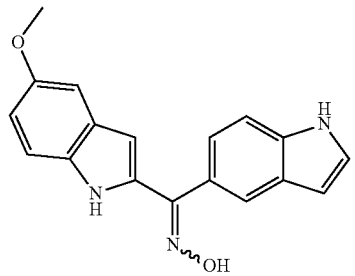 [SMILES: COc1ccc2[nH]c(C(=NO)c3ccc4[nH]ccc4c3)cc2c1]

The mixture of (1H-indol-5-yl)(5-methoxy-1H-indol-2-yl)methanone (62 mg, 0.21 mmol), NH$_2$OH HCl (89 mg, 1.28 mmol), and a solution of LiOH (1 M, 2.1 mL) in 2.1 mL of EtOH was heated at 90° C. for 18 hr, cooled to RT, concentrated, partitioned between EtOAc and saturated ammonium chloride solution. The organic layer was dried (MgSO$_4$), and concentrated. The residue was recrystallized from dichloromethane and hexanes to give (1H-indol-5-yl)(5-methoxy-1H-indol-2-yl)methanone oxime (59 mg, 90% yield) as an off white solid. A mixture of E/Z, 0.17:0.83 $^1$H NMR (399 MHz, DMSO-$d_6$) δ ppm 11.67 (1H, s), 11.24 (1H, br. s.), 11.21 (1H, br. s.), 7.65-7.67 (1H, m), 7.37-7.46 (3H, m), 7.25-7.30 (1H, m), 7.00 (1H, d, J=2.7 Hz), 6.79 (1H, dd, J=9.0, 2.7 Hz), 6.45-6.48 (1H, m), 6.39 (1H, d, J=2.7 Hz), 3.71 (3H, s); MS (ESI) m/z Calculated 305.12 Found 306.28 (M+H)+.

Example 38 benzofuran-2-yl(1-methyl-1H-indol-5-yl)methanone

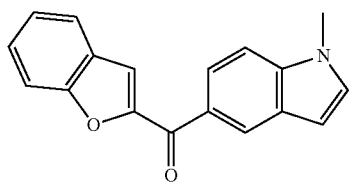 [SMILES: Cn1ccc2cc(C(=O)c3cc4ccccc4o3)ccc21]

1. To a solution of benzofuran (1.5 g, 12.69 mmol) in 60 mL of THF, was added 5.08 mL (12.69 mmol) of n-BuLi solution in hexanes (2.5 M) at −78° C. After 1 hr at −78° C., the reaction mixture was added DMF (3.43 mL). After overnight at RT, the reaction was quenched with saturated ammonium chloride, and extracted with EtOAc (×3). The combined organic extracts were dried (MgSO$_4$), filtered, and concentrated. Flash chromatography (10% EtOAc/Hexanes) gave benzofuran-2-carbaldehyde (1.48 g, 80%). $^1$H NMR (400 MHz, CDCl$_3$) δ ppm: 9.88 (s, 1H), 7.76 (d, J=8.4 Hz, 1H), 7.62 (d, J=8.4 Hz, 1H), 7.57 (s, 1H), 7.52 (td, J=7.2, 1.2 Hz 1H), 7.35 (td, J=7.2, 1.2 Hz, 1H).

2. To solution of 5-bromo-1H-indole (2.08 g, 10.6 mmol) in 35 mL of DMF, was added sodium hydride (60 wt % dispersion, 467 mg, 11.67 mmol) at 0° C. After 30 min, iodomethane (663 µL, 10.6 mmol) was added. The reaction mixture was allowed warm to RT, and stirred at RT for 10 min. The reaction was quenched with water at 0° C., and extracted with EtOAc (×3). The combined organic extracts were dried (MgSO$_4$), filtered, and concentrated. Flash chromatography (10% EtOAc/Hexanes) gave 5-bromo-1-methyl-1H-indole (2.16 g, 97%). $^1$H NMR (400 MHz, CDCl$_3$) δ ppm: 7.74 (d, J=1.6 Hz, 1H), 7.30 (dd, J=8.4, 2.0 Hz, 1H), 7.19 (d, J=8.8 Hz, 1H), 7.05 (d, J=3.2 Hz 1H), 6.42 (d, J=2.8 Hz, 1H), 3.78 (s, 3H).

3. To a solution of 5-bromo-1-methyl-1H-indole (1.44 g, 6.84 mmol) in 30 mL of ethyl ether, was added 52.5 mL of t-BuLi solution in pentane (1.7 M) at −78° C. The reaction mixture was stirred at 0° C. for 30 min. A solution of benzofuran-2-carbaldehyde (1 g, 6.85 mmol) in 10 mL of THF was added slowly at −78° C. After 30 min at 0° C., the reaction mixture was quenched with saturated sodium bicarbonate solution, and extracted with EtOAc (×3). The organic layer was dried (MgSO$_4$), and concentrated. Flash chromatography (35% EtOAc/Hexanes) gave benzofuran-2-yl(1-methyl-1H-indol-5-yl)methanol (1.13 g, 58%). %). $^1$H NMR (400 MHz, CDCl$_3$) δ ppm: 7.74 (s, 1H), 7.51 (d, J=7.6 Hz, 1H), 7.43 (d, J=8.0 Hz, 1H), 7.34 (s, 1H), 7.23 (d, J=7.2 Hz, 1H), 7.18 (t, J=7.2 Hz, 1H), 7.08 (d, J=2.8 Hz, 1H), 6.56 (s, 1H), 6.49 (d, J=2.8 Hz, 1H), 6.06 (d, J=4.4 Hz, 1H), 3.81 (s, 3H), 2.46 (d, J=4.4 Hz, 1H).

4. The mixture of (benzofuran-2-yl(1-methyl-1H-indol-5-yl)methanol (153 mg, 0.55 mmol) and MnO$_2$ (742 mg, 8.53 mmol) in 7 mL of dichloromethane was stirred overnight at RT, The reaction mixture was diluted with dichloromethane, filtered through a pad of Celite, and concentrated. Flash chromatography (35% EtOAc/Hexanes) gave benzofuran-2-yl(1-methyl-1H-indol-5-yl)methanone (143 mg, 94%). $^1$H NMR (400 MHz, CDCl$_3$) δ ppm: 8.46 (d, J=1.6 Hz, 1H), 8.00 (dd, J=8.4, 2.0 Hz, 1H), 7.74 (d, J=8.0 Hz, 1H), 7.67 (d, J=8.4 Hz, 1H), 7.53 (s, 1H), 7.49 (t, J=8.8 Hz, 1H), 7.44 (d, J=8.4 Hz, 1H), 7.33 (t, J=8.0 Hz, 1H), 7.17 (d, J=4.0 Hz, 1H), 6.66 (d, J=3.2 Hz, 1H), 3.87 (s, 3H).

Example 39 benzofuran-2-yl(1H-indol-5-yl)methanone

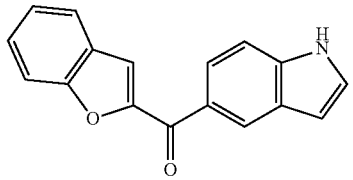 [SMILES: O=C(c1ccc2[nH]ccc2c1)c1cc2ccccc2o1]

1. To a solution of 5-bromo-1H-indole (346 mg, 1.765 mmol) in 8 mL of THF, was added sodium hydride (60 wt % dispersion, 85 mg, 2.1 mmol) at 0° C. After 30 min, the reaction was added 1.54 mL of n-BuLi solution in hexanes (2.5 M) at −10° C. After 1 hr, a solution of benzofuran-2-carbaldehyde (258 mg, 1.765 mmol) in 8 mL of THF was added slowly. The reaction mixture was allowed to warm up to RT slowly, and stirred at RT for 1.5 hr. The reaction was quenched with water, and extracted with EtOAc (×3). The combined organic extracts were dried (MgSO$_4$), filtered, and concentrated. Flash chromatography (50% EtOAc/Hexanes) gave benzofuran-2-yl(1H-indol-5-yl)methanol (150 mg, 33%). $^1$H NMR (400 MHz, CDCl$_3$) δ ppm: 8.21 (br.s, 1H), 7.75 (s, 1H), 7.49 (d, J=7.6 Hz, 1H), 7.40 (t, J=8.4 Hz, 2H), 7.32 (dd, J=8.4, 1.6 Hz, 1H), 7.22 (s, 1H), 7.20 (dd, J=4.8, 1.2 Hz 1H), 7.17 (dd, J=7.2, 1.2 Hz, 1H), 6.57-6.53 (m, 2H), 6.04 (d, J=4.0 Hz, 1H), 2.48 (d, J=4.0 Hz, 1H).

2. The mixture of benzofuran-2-yl(1H-indol-5-yl)methanol (150 mg, 0.438 mmol) and MnO$_2$ (572 mg, 6.58 mmol) in 4 mL of THF was stirred overnight at RT. After overnight, the reaction mixture was filtered through a pad of Celite, and concentrated. Flash chromatography (50% EtOAc/Hexanes) gave benzofuran-2-yl(1H-indol-5-yl)methanone (105 mg, 71%). $^1$H NMR (400 MHz, CDCl$_3$) δ ppm: 8.47 (s, 1H), 8.43 (br.s, 1H), 7.96 (dd, J=8.4, 1.2 Hz, 1H), 7.73 (d, J=7.6 Hz, 1H), 7.66 (d, J=8.4 Hz, 1H), 7.53 (s, 1H), 7.52-7.45 (m, 2H), 7.35-7.29 (m, 2H), 6.71 (s, 1H). MS: 262.09 (M+H+).

Example 40 benzofuran-5-yl(5-methoxy-1H-indol-2-yl)methanone

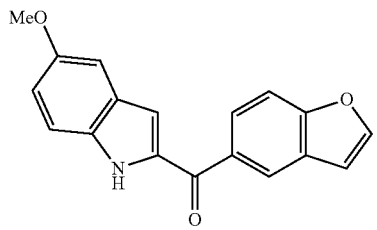 [SMILES: COc1ccc2[nH]c(C(=O)c3ccc4occc4c3)cc2c1]

1. To a solution of 5-methoxy-1-(phenylsulfonyl)-1H-indole (476 mg, 1.64 mmol) in 10 mL of THF, was added 0.69 mL of n-BuLi solution in hexanes (2.5 M) at −78° C. After 1 hr, a solution of benzofuran-5-carbaldehyde (240 mg, 1.64 mmol) in 6 mL of THF was added slowly. The reaction mixture was allowed to warm up to RT slowly. After 1 hr, the reaction was quenched with water, and extracted with EtOAc (×3). The combined organic extracts were dried (MgSO$_4$), filtered, and concentrated to give crude benzofuran-5-yl(5-methoxy-1-(phenylsulfonyl)-1H-indol-2-yl)methanol. The mixture of benzofuran-5-yl(5-methoxy-1-(phenylsulfonyl)-1H-indol-2-yl)methanol and MnO$_2$ (2.13 g, 24.6 mmol) in 25 mL of dichloromethane was stirred overnight at RT. After overnight, the reaction mixture was filtered through a pad of Celite, and concentrated. Flash chromatography (30% EtOAc/Hexanes) gave benzofuran-5-yl(5-methoxy-1-(phenylsulfonyl)-1H-indol-2-yl)methanone (398 mg, 56% for two step). $^1$H NMR (400 MHz, CDCl$_3$) δ ppm: 8.06 (d, J=9.2 Hz, 1H), 8.02 (d, J=7.2 Hz, 2H), 7.71 (d, J=7.6 Hz, 1H), 7.62 (d, J=8.8 Hz, 1H), 7.58-7.42 (m, 5H), 7.31 (t, J=7.2 Hz, 1H), 7.14 (s, 1H), 7.09 (dd, J=9.2, 2.4 Hz, 1H), 6.99 (d, J=2.4 Hz, 1H), 3.82 (s, 3H).

2. To a solution benzofuran-5-yl(5-methoxy-1-(phenylsulfonyl)-1H-indol-2-yl)methanone (398 mg, 0.923 mmol) in 5 mL of THF, was added 9.23 mL of TBAF solution in THF (1 M). The reaction mixture was heated to reflux overnight. After cooled to RT, the reaction mixture was poured into water, and extracted with EtOAc (×3). The combined organic extracts were washed with water, dried (MgSO$_4$), filtered, and concentrated. Flash chromatography (30% EtOAc/Hexanes) gave benzofuran-5-yl(5-methoxy-1H-indol-2-yl)methanone (226 mg, 84%). $^1$H NMR (400 MHz, CDCl$_3$) δ ppm: 9.23 (br.s, 1H), 7.80 (d, J=2.0 Hz, 1H), 7.79-7.74 (m, 2H), 7.69 (d, J=8.4 Hz, 1H), 7.52 (td, J=7.2, 1.6 Hz, 1H), 7.39-7.33 (m, 2H), 7.18 (d, J=2.4 Hz, 1H), 7.09 (dd, J=9.2, 2.4 Hz, 1H), 3.87 (s, 3H).

Example 41

(1H-indol-6-yl)(5-methoxy-1H-indol-2-yl)methanone

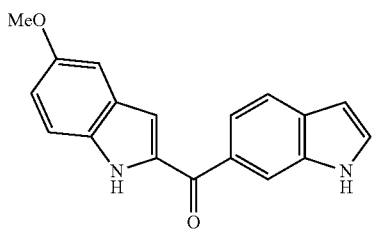 [SMILES: COc1ccc2[nH]c(C(=O)c3ccc4cc[nH]c4c3)cc2c1]

1. To a solution of 5-methoxy-1-(phenylsulfonyl)-1H-indole (217 mg, 0.756 mmol) in 5 mL of THF, was added 0.33 mL of n-BuLi solution in hexanes (2.5 M) at −78° C. After 1 hr, a solution of 1-(phenylsulfonyl)-1H-indole-6-carbaldehyde (237 mg, 0.831 mmol) in 3 mL of THF was added slowly. After 1 hr, the reaction mixture was allowed to warm up to RT slowly, quenched with saturated ammonium chloride solution, and extracted with EtOAc. The organic layer was dried (MgSO$_4$), and concentrated. Chromatography over 10 g SiO$_2$ (50% EtOAc/Hexanes) gave (5-methoxy-1-(phenylsulfonyl)-1H-indol-2-yl)(1-(phenylsulfonyl)-1H-indol-6-yl)methanol (337 mg, 0.588 mmol, 71%) as an off white foam. $^1$H NMR (399 MHz, CHLOROFORM-d) δ ppm 8.08 (1H, d, J=0.8 Hz), 7.98 (1H, d, J=9.4 Hz), 7.80 (2H, dd, J=8.6, 1.2 Hz), 7.55-7.64 (3H, m), 7.42-7.54 (3H, m), 7.27-7.34 (4H, m), 7.24 (1H, s), 6.91 (1H, dd, J=9.2, 2.5 Hz), 6.82 (1H, d, J=2.3 Hz), 6.66 (1H, dd, J=3.5, 0.8 Hz), 6.49 (1H, d, J=5.1 Hz), 6.15 (1H, s), 3.79 (3H, s), 3.43 (1H, d, J=4.7 Hz)

2. The mixture of (5-methoxy-1-(phenylsulfonyl)-1H-indol-2-yl)(1-(phenylsulfonyl)-1H-indol-6-yl)methanol and MnO$_2$ (1.5 g, 17.25 mmol) in 6 mL of dichloromethane was stirred overnight at RT, diluted with dichloromethane, filtered through a pad of Celite, and concentrated. Chromatography over 25 g SiO$_2$ (50% EtOAc/Hexanes) gave to give (5-methoxy-1-(phenylsulfonyl)-1H-indol-2-yl)(1-(phenylsulfonyl)-1H-indol-6-yl)methanone (94 mg, 0.17 mmol, 28%) as a yellow solid. $^1$H NMR (399 MHz, CHLOROFORM-d) δ ppm 8.56 (1H, s), 8.06 (1H, d, J=9.4 Hz), 7.94-7.99 (2H, m), 7.87-7.93 (3H, m), 7.76 (1H, d, J=3.5 Hz), 7.62 (1H, d, J=8.2 Hz), 7.57 (2H, q, J=7.4 Hz), 7.42-7.52 (4H, m), 7.08 (1H, dd, J=9.0, 2.7 Hz), 7.00 (1H, d, J=2.3 Hz), 6.89 (1H, s), 6.73 (1H, d, J=3.9 Hz), 3.84 (3H, s)

3. To a solution of (5-methoxy-1-(phenylsulfonyl)-1H-indol-2-yl)(1-(phenylsulfonyl)-1H-indol-6-yl)methanone (94 mg, 0.17 mmol) in 3 mL of THF, was added 0.83 mL of TBAF solution in THF (1 M). The reaction mixture was heated to reflux overnight, cooled to RT, diluted with EtOAc, washed with brine (×2), dried (MgSO$_4$), and concentrated. Chromatography over 10 g SiO$_2$ (60% EtOAc/Hexanes) gave (1H-indol-6-yl)(5-methoxy-1H-indol-2-yl)methanone (31 mg, 0.11 mmol, 65%). $^1$H NMR (399 MHz, DMSO-d$_6$) δ ppm 9.18 (1H, br. s.), 8.47 (1H, br. s.), 8.13 (1H, s), 7.83 (1H, dd, J=8.4, 1.4 Hz), 7.76 (1H, d, J=8.4 Hz), 7.35-7.46 (2H, m), 7.02-7.15 (3H, m), 6.67 (1H, td, J=2.1, 1.0 Hz), 3.86 (3H, s); MS (ESI) m/z Calculated 290.11 Found 291.27 (M+H)+.

What is claimed is:
1. A compound having the structure:

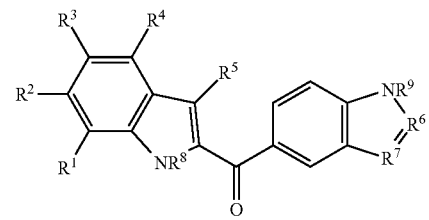

wherein:
R1-R5 and R10 are independently H, halo, OH, C1-C9 alkyl, C1-C9 alkyl amine, or C1-C9 alkyl ether, and each of C1-C9 alkyl, C1-C9 alkyl amine, and C1-C9 alkyl ether is substituted with 0-3 groups selected from OR', =O, =NR', =N—OR', NR'R", —SR', halogen, —SiR'R"R'", —OC(O)R', —C(O)R', —CO$_2$R', —CONR'R", —OC(O)NR'R", NR' C(O)R', —NR' C(O)NR"R'", —NR' SO$_2$NR'", —NR" CO$_2$R', —NHC(NH$_2$)=NH, —NR'C(NH$_2$)=NH, —NHC(NH$_2$)=NR', —S(O)R', —SO$_2$R', —SO$_2$NR'R", —NR"SO$_2$R, —CN, and NO$_2$ and comprises 0-3 heteroatoms selected from N, O, S, and P;
R6-R7 are independently N or CR10;
R8 is H or Me;
R9 is H;
R', R", and R'" are each independently hydrogen, unsubstituted (C1-C8)alkyl, unsubstituted (C1-C8)heteroalkyl, unsubstituted aryl, aryl substituted with 1-3 halogens, unsubstituted alkyl, unsubstituted alkoxy, unsubstituted thioalkoxy, or aryl-(C1-C4)alkyl, or a pharmaceutically acceptable salt thereof.

2. The compound of claim 1, wherein R1, R2, R4, and R5 are H, or a pharmaceutically acceptable salt thereof.

3. The compound of claim 1, wherein R3 is OH or C1-C6 alkyl ether, or a pharmaceutically acceptable salt thereof.

4. The compound of claim 1, wherein R7 is CR10, or a pharmaceutically acceptable salt thereof.

5. The compound of claim 1, wherein R8 or R9 are H, or a pharmaceutically acceptable salt thereof.

6. The compound of claim 1, wherein R1, R2, R4, and R5 are H; and R3 is OH or C1-C6 alkyl ether, or a pharmaceutically acceptable salt thereof.

7. The compound of claim 1, wherein R1, R2, R4, and R5 are H; and R7 is CR10, or a pharmaceutically acceptable salt thereof.

8. The compound of claim 1, wherein R1, R2, R4, and R5 are H; and R8 and R9 are H, or a pharmaceutically acceptable salt thereof.

9. The compound of claim 1, wherein R3 is OH or C1-C6 alkyl ether; and R7 is CR10, or a pharmaceutically acceptable salt thereof.

10. The compound of claim 1, wherein R3 is OH or C1-C6 alkyl ether; and R8 and R9 are H, or a pharmaceutically acceptable salt thereof.

11. The compound of claim 1, wherein R7 is CR10; and R8 and R9 are H, or a pharmaceutically acceptable salt thereof.

12. The compound of claim 1, wherein R1, R2, R4, and R4 are H; R3 is OH, or C1-C6 alkyl ether; and R7 is CR10, or a pharmaceutically acceptable salt thereof.

13. The compound of claim 1, wherein R1, R2, R4, and R4 are H; R3 is OH or C1-C6 alkyl ether; R8 and R9 are H, or a pharmaceutically acceptable salt thereof.

14. The compound of claim 1, wherein R3 is OH or C1-C6 alkyl ether; R7 is CR10; and R8 and R9 are H, or a pharmaceutically acceptable salt thereof.

15. The compound of claim 1, wherein R1, R2, R4, and R4 are H; R3 is OH or C1-C6 alkyl ether; R7 is CR10; and R8 and R9 are H, or a pharmaceutically acceptable salt thereof.

16. The compound of claim 1, wherein the compound is a diindolylmethanone or indol-2-yl, indol-6-yl-methanone, or a pharmaceutically acceptable salt thereof.

17. The compound of claim 1, wherein the compound has a structure selected from:

| # | Structure |
|---|---|
| 1 | MeO-indole-C(=O)-indole |
| 4 | MeO-indole-C(=O)-(3-methyl-indole) |
| 5 | MeO-(3-methyl-indole)-C(=O)-indole |
| 6 | MeO-(3-methyl-indole)-C(=O)-(3-methyl-indole) |
| 7 | MeO-(3-chloro-indole)-C(=O)-(3-methyl-indole) |
| 8 | MeO-indole-C(=O)-(3-(CH2-NMe2)-indole) |
| 9 | MeO-indole-C(=O)-(3-chloro-indole) |
| 10a | MeO-(4-Cl,3-Cl-indole)-C(=O)-(3-Cl-indole) |
| 10b | MeO-(3-Cl-indole)-C(=O)-(3-Cl-indole) |

| # | Structure |
|---|---|
| 11 | 5-hydroxy-1H-indol-2-yl)(1H-indol-5-yl)methanone |
| 12 | (5-hydroxy-1H-indol-2-yl)(3-methyl-1H-indol-5-yl)methanone |
| 13 | (5-(2-(dimethylamino)ethoxy)-1H-indol-2-yl)(3-methyl-1H-indol-5-yl)methanone hydrochloride |
| 14 | (5-morpholino-1H-indol-2-yl)(1H-indol-5-yl)methanone |
| 15 | (5,6-dimethoxy-1H-indol-2-yl)(1H-indol-5-yl)methanone |
| 16 | (5-chloro-1H-indol-2-yl)(1H-indol-5-yl)methanone |
| 17 | (5-fluoro-1H-indol-2-yl)(3-methyl-1H-indazol-5-yl)methanone |
| 18 | (5-methoxy-1H-indol-2-yl)(3-methyl-1H-indazol-5-yl)methanone |
| 19 | (3-ethyl-1H-indazol-5-yl)(5-methoxy-1H-indol-2-yl)methanone |
| 20 | (3-chloro-1H-indazol-5-yl)(5-methoxy-1H-indol-2-yl)methanone |
| 21 | (3-fluoro-1H-indazol-5-yl)(5-methoxy-1H-indol-2-yl)methanone |
| 22 | (5-methoxy-1H-indol-2-yl)(3-(morpholinomethyl)-1H-indazol-5-yl)methanone |
| 23 | (3-chloro-5-methoxy-1H-indol-2-yl)(1H-indazol-5-yl)methanone |

-continued

| # | Structure |
|---|---|
| 24 | 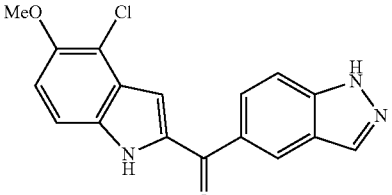 |
| 25 | 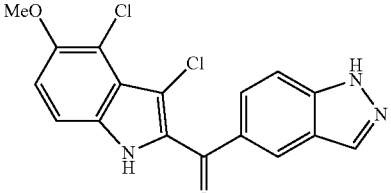 |
| 26 | 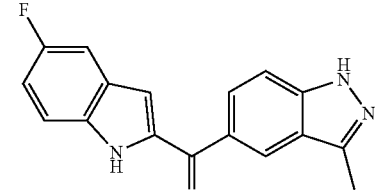 |
| 27 | 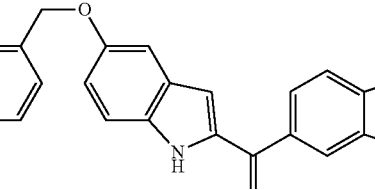 |
| 28 | 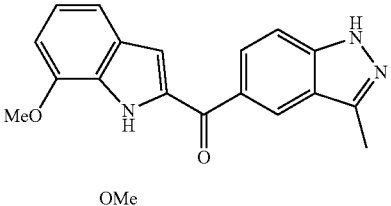 |
| 29 | 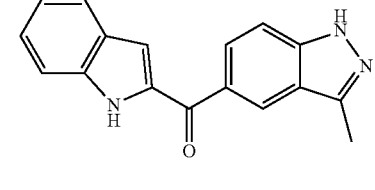 |

-continued

| # | Structure |
|---|---|
| 30 | 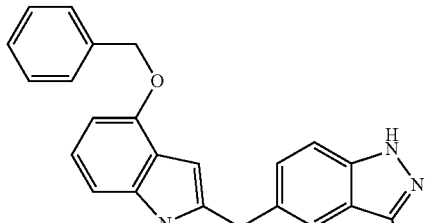 |
| 34 | 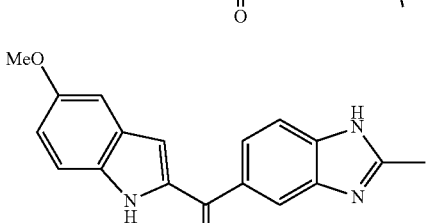 |
| 35 | 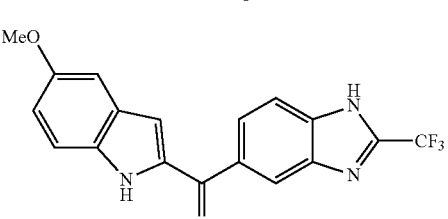 and |
| 36 | 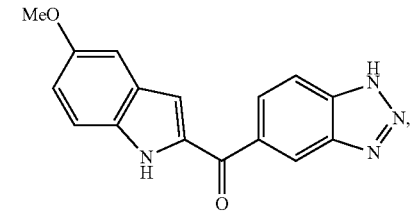 [SMILES: COc1ccc2[nH]c(C(=O)c3ccc4[nH]nnc4c3)cc2c1] | or a pharmaceutically acceptable salt thereof.

18. A pharmaceutical composition suitable for administration to a human and comprising a compound of claim 1, or a pharmaceutically acceptable salt thereof.

19. A composition comprising a compound of claim 1, or a pharmaceutically acceptable salt thereof, copackaged or coformulated with a second, different medicament for inhibiting tumor cell growth, treating cancer, or inhibiting metastasis.

20. A method of treating a cancer in a person in need thereof, the method comprising administering to the person an effective amount of a compound of claim 1, or a pharmaceutically acceptable salt thereof.

* * * * *